US006268391B1

(12) United States Patent
Dickerson et al.

(10) Patent No.: US 6,268,391 B1
(45) Date of Patent: Jul. 31, 2001

(54) BENZYLIDENE-1,3-DIHYDRO-INDOL-2-ONE DERIVATIVES A RECEPTOR TYROSINE KINASE INHIBITORS, PARTICULARLY OF RAF KINASES

(75) Inventors: Scott Howard Dickerson, Chapel Hill; Philip Anthony Harris; Robert Neil Hunter, III, both of Raleigh; David Kendall Jung, Durham; Karen Elizabeth Lackey, Hillsborough; Robert Walton McNutt, Jr., Durham; Michael Robert Peel, Chapel Hill; James Marvin Veal, Apex, all of NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/446,586

(22) PCT Filed: Aug. 4, 1998

(86) PCT No.: PCT/EP98/04844

§ 371 Date: Apr. 7, 2000

§ 102(e) Date: Apr. 7, 2000

(87) PCT Pub. No.: WO99/10325

PCT Pub. Date: Mar. 4, 1999

(30) Foreign Application Priority Data

Aug. 6, 1997 (GB) .................................................. 9716557

(51) Int. Cl.⁷ ..................... A61K 31/404; C07D 209/34
(52) U.S. Cl. .................... 514/418; 548/486; 548/466; 548/433; 548/235; 548/181; 548/151; 546/84; 546/277.7; 514/292; 514/339; 514/365; 514/366; 514/374; 514/381

(58) Field of Search ..................................... 514/418, 379, 514/381, 366, 365, 339, 292; 548/486, 151, 181, 235, 252, 433, 466; 546/84, 277.7

(56) References Cited

U.S. PATENT DOCUMENTS 5,834,504 * 11/1998 Tang et al. ........................... 514/418

FOREIGN PATENT DOCUMENTS

| 2 306 108 | 4/1997 | (GB) . |
| WO 96 40116 | 12/1996 | (WO) . |
| WO 97 25986 | 7/1997 | (WO) . |
| WO 98 07695 | 2/1998 | (WO) . |

* cited by examiner

*Primary Examiner*—C. S. Aulakh
(74) *Attorney, Agent, or Firm*—John L. Lemanowicz

(57) ABSTRACT

Compounds of general formula (I) wherein: $R^1$ is H or optionally joined with $R^2$ to form a fused ring selected from the group consisting of five to ten membered aryl, heteroaryl or heterocyclyl rings, $R^2$ and $R^3$ are independently H, HET, aryl, $C_{1-12}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NO^{12}SO_2R^{11}$, $-NR^{12}C(NR^{\ 12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^{11}$, $R^6$ and $R^7$ are independently halogen, CN, $NO_2$, $-CONR^{10}R^{11}$, $-SO_2NR^{10}R^{11}$, $-NR^{10}R^{11}$, or $-OR^{11}$, where $R^{10}$ and $R^{11}$ are as defined below; $R^8$ is OH, $NHSO_2R^{12}$ or $NHCOCF_3$; and their use in therapy, especially in the treatment of disorders mediated by cRaf1 kinase.

26 Claims, No Drawings

BENZYLIDENE-1,3-DIHYDRO-INDOL-2-ONE DERIVATIVES A RECEPTOR TYROSINE KINASE INHIBITORS, PARTICULARLY OF RAF KINASES

FIELD OF THE INVENTION

The present invention provides novel compounds, novel compositions, methods of their use and methods of their manufacture, such compounds generally pharmacologically useful as agents in those disease states alleviated by the alteration of mitogen activated signalling pathways in general, and in particular the inhibition or antagonism of protein kinases, which pathologically involve aberrant cellular proliferation, such disease states including tumor growth. The aforementioned pharmacologic activities are useful in the treatment of mammals. In particular, the invention relates to benzylidene oxindole derivatives which exhibit cRaf-1 kinase inhibition for the treatment of disorders related to cell proliferation.

More specifically, the compounds of the present invention can be used in the treatment of certain forms of cancer, can be used to provide additive or synergistic effects with certain existing cancer chemotherapies, and/or used to restore effectiveness of certain existing cancer chemotherapies and radiation. At the present time, there is a need in the areas of diseases characterized by cell proliferation for such therapeutic agents.

BACKGROUND OF THE INVENTION

Cancer results from the deregulation of the normal processes that control cell division, differentiation and apoptotic cell death. Protein kinases play a critical role in this regulatory process. A partial non-limiting list of such kinases includes ab1, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK4, flt-1, Fps, Frk, Fyn, Hck, IGF-1R, INS-R, Jak, KDR, Lck, Lyn, MEK, p38, PDGFR, PIK, PKC, PYK2, ros, tie$_1$, tie$_2$, TRK, Yes and Zap70. In mammalian biology, such protein kinases comprise mitogen activated protein kinase (MAPK) signalling pathways. MAPK signalling pathways are inappropriately activated by a variety of common disease-associated mechanisms such as mutation of ras genes and deregulation of growth factor receptors (Magnuson et al, Seminars in Cancer Biology; 1994 (5), 247–252). Therefore the inhibition of protein kinases is an object of the present invention.

Additionally, protein kinases have been implicated as targets in central nervous system disorders (such as Alzheimer's), inflammatory disorders (such as psoriasis), bone diseases (such as osteoporosis), atheroscleroses, restenosis, thrombosis, metabolic disorders (such as diabetes) and infectious diseases (such as viral and fungal infections).

One of the most commonly studied pathways involving kinase regulation is cellular signalling from receptors at the cell surface to the nucleus (Crews and Erikson, 1993). One example of this pathway includes a cascade of kinases in which members of the Growth Factor receptor Tyrosine Kinases (such as EGF-R, PDGF-R, VEGF-R, IGF1-R, the Insulin receptor), deliver signals through phosphorylation to other kinases such as Src Tyrosine kinase, and the Raf, Mek and Erk serine/threonine kinase families (Crews and Erikson, 1993; Ihle et al., 1994). Each of these kinases is represented by several family members (Pelech and Sanghera, 1992) which play related, but functionally distinct roles. The loss of regulation of the growth factor signalling pathway is a frequent occurrence in cancer as well as other disease states.

The signals mediated by kinases have also been shown to control growth, death and differentiation in the cell by regulating the processes of the cell cycle (Massague and Roberts, 1995). Progression through the eukaryotic cell cycle is controlled by a family of kinases called cyclin dependent kinases (CDKs) (Myerson et al., 1992). The regulation of CDK activation is complex, but requires the association of the CDK with a member of the cyclin family of regulatory subunits (Draetta, 1993; Murray and Kirschner, 1989; Solomon et al., 1992). A further level of regulation occurs through both activating and inactivating phosphorylations of the CDK subunit (Draetta, 1993; Ducommun et al., 1991; Gautier et al., 1989; Gould and Nurse, 1989; Krek and Nigg, 1991; Murray and Kirschner, 1989; Solomon et al., 1992; Solomon et al., 1990). The coordinate activation and inactivation of different cyclin/CDK complexes is necessary for normal progression through the cell cycle (Pines, 1993; Sherr, 1993). Both the critical G1-S and G2-M transitions are controlled by the activation of different cyclin/CDK activities. In G1, both cyclin D/CDK4 and cyclin E/CDK2 are thought to mediate the onset of S-phase (Matsushime et al., 1994; Ohtsubo and Roberts, 1993; Quelle et al., 1993; Resnitzky et al., 1994). Progression through S-phase requires the activity of cyclin A/CDK2 (Girard et al., 1991; Pagano et al., 1992; Rosenblatt et al., 1992; Walker and Maller, 1991; Zindy et al., 1992) whereas the activation of cyclin A/cdc2 (CDK1) and cyclin B/cdc2 are required for the onset of metaphase (Draetta, 1993; Girard et al., 1991; Murray and Kirschner, 1989; Pagano et al., 1992; Rosenblatt et al., 1992; Solomon et al., 1992; Walker and Maller, 1991; Zindy et al., 1992). It is not surprising, therefore, that the loss of control of CDK regulation is a frequent event in hyperproliferative diseases and cancer. (Hunter and Pines, 1994; Lees, 1995; Pines, 1992)

The kinase cRaf1 regulates cellular proliferation in two ways. The enzyme positively regulates cell division through the Raf/MEK/ERK protein kinase cascade. This activation is the result of cRaf1 catalyzed phosphorylation of the protein kinase, MEK1. MEK1 phosphorylates and activates the protein kinase ERK. ERK phosphorylates and regulates transcription factors required for cell division (Avruch et al, TIBS; 1994 (19) 279–283). cRaf1 negatively regulates cell death by modulation of the activity of Bcl-2, a critical regulator of apoptosis. This regulation involves direct phosphorylation of Bcl-2 family members (Gajewski and Thompson, Cell: 1996 (87) 619–628). Both of these aspects of cRaf1 mediated regulation of cellular proliferation require the kinase activity of cRaf1.

cRaf1 is deregulated by events that are common in human cancer. For example ras genes are mutated with the following frequencies in the following representative primary human tumors: lung (adenocarcinoma), 30%; colon (adenocarcinoma), 50%; pancreatic carcinoma, 90%; seminoma, 40%; thyroid, 50% (McCormick, *Ras oncogenes* in Oncogenes and the molecular origins of cancer: 1989, 125–146). cRaf1 is also activated by deregulation of tyrosine kinases including, cSrc, ErbB2, EGFR, and bcr/abl. These events are associated with breast, colon and lung carcinomas and chronic myelogenous leukemia (Fearon, *Genetic lesions in human cancer,* in Molecular oncology; 1996, 143–178). In addition, Raf anti-sense literature teaches that the reduction of Raf protein levels correlates with a reduction in tumor growth rate in in vivo tumor mouse models. Inhibitors of the kinase activity of cRaf1 should therefore provide effective treatment for a wide variety of common human cancers.

Inhibitors of kinases involved in mediating or maintaining these disease states represent novel therapies for these disorders. Examples of such kinases include, but are not limited to: (1) inhibition of Src (Brickell, 1992; Courtneidge, 1994), raf (Powis, 1994) and the cyclin-dependent kinases (CDKs) 1, 2 and 4 in cancer (Hunter and Pines, 1994; Lees, 1995; Pines, 1992), (2) inhibition of CDK2 or PDGF-R kinase in restenosis (Buchdunger et al., 1995), (3) inhibition of CDK5 and GSK3 kinases in Alzheimers (Aplin et al., 1996; Hosoi et al., 1995), (4) inhibition of c-Src kinase in osteoporosis (Tanaka et al., 1996), (5) inhibition of GSK-3 kinase in type-2 diabetes (Borthwick et al., 1995); (6) inhibition of the p38 kinase in inflammation (Badger et al., 1996); (7) inhibition of VEGF-R 1-3 and TIE-1 and -2 kinases in angiogenesis (Shawver et al., 1997); (8) inhibition of UL97 kinase in viral infections (He et al., 1997); (9) inhibition of CSF-1R kinase in bone and hematopoetic diseases (Myers et al., 1997), and (10) inhibition of Lck kinase in autoimmune diseases and transplant rejection (Myers et al., 1997)

The present invention relates to certain benzylidene oxindole derivatives which not only have anti-cancer properties but also are selective and potent inhibitors of the serine/threonine kinase cRaf1 thereby allowing selective reduction or elimination of particular disease tissues. Some of the compounds of the present invention may selectively inhibit another therapeutically relevent kinase.

It is an object of the present invention to provide potent specific, orally, intravenously, or subcutaneously active small molecule inhibitors of the signal transduction activity of Raf kinases for the treatment of human malignancies, for example, one or more of breast, stomach, ovary, colon, lung, brain, larynx, lymphatic system, genitourinary tract (including bladder and prostate), ovarian, gastric, bone, or pancreatic tumors, preferably those which signal through cRaf-1, using the compounds of the present invention, methods of their administration, methods of their formulation, and methods of their synthesis.

The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation and neurodegenerative diseases.

SUMMARY OF THE INVENTION

In summary, the invention includes a family of compounds having the general structural formula (I):

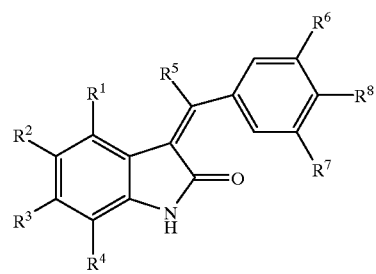

wherein:
$R^1$ is H or optionally joined with $R^2$ to form a fused ring selected from the group consisting of five to ten membered aryl, heteroaryl or heterocyclyl rings, said heteroaryl or said heterocyclyl rings having one to three heteroatoms where zero to three of said heteroatoms are N and zero to 1 of said heteroatoms are O or S and where said fused ring is optionally substituted by one to three of $R^9$, where $R^2$ and $R^9$ are as defined below;

$R^2$ and $R^3$ are independently H, HET, aryl, $C_{1-2}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^{11}$ where said $C_{1-12}$ aliphatic optionally bears one or two insertions of one to two groups selected from C(O), O, S, S(O), $SO_2$ or $NR^{12}$; with said HET, aryl or $C_{1-12}$ aliphatic being optionally substituted by one to three of $R^{10}$; and where $R^2$ is optionally joined with $R^3$ to form a fused ring selected from the group consisting of five to ten membered aryl, heteroaryl or heterocyclyl rings, said heteroaryl or said heterocyclyl rings having zero to three heteroatoms where zero to three of said heteroatoms are N and zero to one of said heteroatoms are O or S and where said fused ring is optionally substituted by one to three of $R^9$, where HET, $R^9$, $R^{10}$, $R^{11}$ and $R^{12}$ are as defined below;

$R^4$ is H, halogen, $NO_2$ or CN;

$R^5$ is H or $C_{1-12}$ aliphatic optionally substituted by one to three of halo, hydroxyl, heteroaryl, or aryl;

$R^6$ and $R^7$ are independently halogen, CN, $NO_2$, $-CONR^{10}R^{11}$, $-SO_2NR^{10}R^{11}$, $-NR^{10}R^{11}$, or $-OR^{11}$, where $R^{10}$ and $R^{11}$ are as defined below;

$R^8$ is OH, $NHSO_2R^{12}$ or $NHCOCF_3$;

$R^9$ is each independently halogen, $C_{1-12}$ aliphatic, CN, $-NO_2$, $R^{10}$, $-OR^{11}$, $-SR^{11}$, $-S(O)R^{10}$, $-SO_2R^{10}$, $-NR^{10}R^{11}$, $-N^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-CO_2R^{11}$, $-CONR^{12}R^{11}$, $-SO_2NR^{12}R^{11}$, $-OCONR^{12}R^{11}$ or $C(NR^{12})NR^{12}R^{11}$, where $R^{10}$, $R^{11}$ and $R^{12}$ are as defined below;

$R^{10}$ is each independently H, halogen, $C_{1-12}$ aliphatic, aryl or HET, where said $C_{1-12}$ aliphatic optionally bears an inserted one to two groups selected from O, S, S(O), $SO_2$ or $NR^{12}$, where said $C_{1-12}$ aliphatic, aryl or HET is optionally substituted by one to three of halo, another HET, aryl, CN, $-SR^{12}$, $-OR^{12}$, $-N(R^{12})_2$, $-S(O)R^{12}$, $-SO_2R_{12}$, $-SO_2N(R^{12})_2$, $-NR^{12}COR^{12}$, $-NR^{12}CO_2R^{12}$, $-NR^{12}CON(R^{12})_2$, $-NR^{12}(NR^{12})NHR^{12}$, $-CO_2R^{12}$, $-CON(R^{12})_2$, $-NR^{12}SO_2R^{12}$, $-OCON(R^{12})_2$, where HET and $R^{12}$ are as defined below;

$R^{11}$ is H or $R^{10}$;

$R^{12}$ is H, $C_{1-12}$ aliphatic or HET, said $C_{1-12}$ aliphatic optionally substituted by one to three of halogen or OH where HET is as defined below; and HET is a five to ten—membered saturated or unsaturated heterocyclic ring selected from the group consisting of benzofuran, benzoxazole, dioxin, dioxane, dioxolane, dithiane, dithiazine, dithiazoie, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

A preferred group of compounds of the present invention are those of the general formula (I)

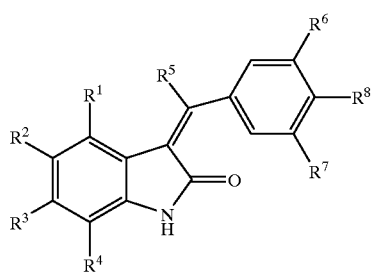

(I)

wherein $R^1$ is H or optionally joined with $R^2$ to form a fused ring selected from the group as defined for HET below, and where said fused ring is optionally substituted by one to three of $R^9$, where $R^2$ and $R^9$ are as defined below;

$R^2$ and $R^3$ are independently H, HET, aryl, $C_{1-6}$ aliphatic, CN, $NO_2$, halogen, $R^{10}$, —$OR^{10}$, —$SR^{10}$, —$S(O)R^{10}$, —$SO_2R^{10}$, —$NR^{10}R^{11}$, —$NR^{11}R^{12}$, —$NR^{12}COR^{11}$, —$NR^{12}CO_2R^{11}$, —$NR^{12}CONR^{11}R^{12}$, —$NR^{12}SO_2R^{11}$, —$NR^{12}C(NR^{12})NHR^{11}$, —$COR^{11}$, —$CO_2R^{11}$, —$CONR^{12}R^{11}$, —$SO_2NR^{12}R^{11}$, —$OCONR^{12}R^{11}$, $C(NR^{12})NR^{12}R^{11}$ where said $C_{1-6}$ aliphatic optionally bears one or two insertions of one to two groups selected from C(O), O, S, S(O), $SO_2$ or $NR^{12}$; with said HET, aryl or $C_{1-6}$ aliphatic being optionally substituted by one to three of $R^{10}$; and where $R^2$ is optionally joined with $R^3$ to form a fused ring selected from the group as defined below and where said fused ring is optionally substituted by one to three of $R^9$, where HET, $R^9$, $R^{10}$, $R^{11}$ and $R^{12}$ are as defined below;

$R^4$ is H, halogen, $NO_2$ or CN;

$R^5$ is H or $C_{1-6}$ aliphatic optionally substituted by one to three of halo, OH, or aryl;

$R^6$ and $R^7$ are independently halogen, CN, $NO_2$, —$CONR^{10}R^{11}$, —$SO_2NR^{10}R^{11}$, —$NR^{10}R^{11}$, or —$OR^{11}$, where $R^{10}$ and $R^{11}$ are as defined below;

$R^8$ is OH, $NHSO_2R^{12}$ or $NHCOCF_3$;

$R^9$ is each independently halo, $C_{1-6}$ aliphatic, CN, —$NO_2$, $R^{10}$, —$OR^{11}$, —$SR^{11}$, —$S(O)R^{10}$, —$SO_2R^{10}$, —$NR^{10}R^{11}$, —$N^{11}R^{12}$, —$NR^{12}COR^{11}$, —$NR^{12}CO_2R^{11}$, —$NR^{12}CONR^{11}R^{12}$, —$NR^{12}SO_2R^{11}$, —$NR^{12}C(NR^{12})NHR^{11}$, —$CO_2R^{11}$, —$CONR^{12}R^{11}$, —$SO_2NR^{12}R^{11}$, —$OCONR^{12}R^{11}$ or $C(NR^{12})NR^{12}R^{11}$, where $R^{10}$, $R^{11}$ and $R^{12}$ are as defined below;

$R^{10}$ is each independently H, halogen, $C_{1-6}$ aliphatic, aryl or HET, where said $C_{1-6}$ aliphatic optionally bears an inserted one to two groups selected from O, S, S(O), $SO_2$ or $NR^{12}$, where said $C_{1-6}$ aliphatic, aryl or HET is optionally substituted by one to three of halo, another HET, aryl, CN, —$SR^{12}$, —$OR^{12}$, —$N(R^{12})_2$, —$S(O)R^{12}$, —$SO_2R^{12}$, —$SO_2N(R^{12})_2$, —$NR^{12}COR^{12}$, —$NR^{12}CO_2R^{12}$, —$NR^{12}CON(R^{12})_2$, —$NR(NR^{12})NHR^{12}$, —$CO_2R^{12}$, —$CON(R^{12})_2$, —$NR^{12}SO_2R^{12}$, —$OCON(R^{12})_2$, where HET and $R^{12}$ are as defined below;

$R^{11}$ is H or $R^{10}$;

$R^{12}$ is H, $C_{1-6}$ aliphatic or HET, said $C_{1-6}$ aliphatic optionally substituted by one to three of halogen or OH where HET is as defined below; and HET is a five to ten—membered saturated or unsaturated heterocyclic ring selected from the group consisting of benzofuran, benzoxazole, dioxin, dioxane dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

A highly preferred group of compounds of the present invention are those of the general formula (I)

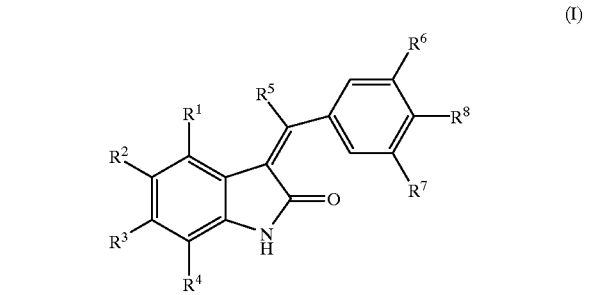

(I)

wherein $R^1$ is H or optionally joined with $R^2$ to form a fused ring selected from the group consisting of fused pyridine, fused triazole, fused thiazole or fused amino-substituted thiazole;

$R^2$ and $R^3$ are independently H, HET, aryl, $C_{1-6}$ aliphatic, —$R^{12}NH_2$, —$R^{12}$-halogen, CN, $NO_2$, halogen, $R^{10}$, —$OR^{10}$, —$SR^{10}$, —$S(O)R^{10}$, —$SO_2R^{10}$, —$NR^{10}R^{11}$, —$NR^{11}R^{12}$, —$NR^{12}COR^{11}$, —$NR^{12}CO_2R^{11}$, —$NR^{12}CONR^{11}R^{12}$, —$NR^{12}SO_2R^{11}$, —$NR^{12}C(NR^{12})NHR^{11}$, —$COR^{11}$, —$COR^{11}NR^{12}R^{11}$—$CO_2R^{11}$, —$CONR^{12}R^{11}$, —$SO_2NR^{12}R^{11}$, —$OCONR^{12}R^{11}$, —$C(NH)R^{11}$, —$C(NR^{12})NR^{12}R^{11}$ where said $C_{1-6}$ aliphatic optionally bears an insertion of a C(O) group; with said HET, aryl or $C_{1-6}$ aliphatic being optionally substituted by one to three of $R^{10}$; and where $R^2$ is optionally joined with $R^3$ to form a fused ring selected from the group as defined for HET below and where said fused ring is optionally substituted by one to three of $R^9$, where HET, $R^9$, $R^{10}$, $R^{11}$ and $R^{12}$ are as defined below;

$R^4$ is H, halogen, $NO_2$ or CN;

$R^5$ is H or $C_{1-6}$ aliphatic optionally substituted by one to three of halogen, OH, or aryl;

$R^6$ and $R^7$ are independently halogen, CN, $NO_2$, —$CONR^{10}R^{11}$, —$SO_2NR^{10}R^{11}$, —$NR^{10}R^{11}$, or —$OR^{11}$, where $R^{10}$ and $R^{11}$ are as defined below;

$R^8$ is OH, $NHSO_2R^{12}$ or $NHCOCF_3$;

$R^9$ is each independently halo, $C_{1-6}$ aliphatic, CN, $-NO_2$, $R^{10}$, $-OR^{11}$, $-SR^{11}$, $-S(O)R^{10}$, $-SO_2R^{10}$, $-NR^{10}R^{11}$, $-N^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-CO_2R^{11}$, $-CONR^{12}R^{11}$, $-SO_2NR^{12}R^{11}$, $-OCONR^{12}R^{11}$ or $C(NR^{12})NR^{12}R^{11}$, where $R^{10}$, $R^{11}$ and $R^{12}$ are as defined below;

$R^{10}$ is each independently H, halogen, $C_{1-6}$ aliphatic, aryl or HET, where said $C_{1-6}$ aliphatic optionally bears an inserted one to two groups selected from O, S, S(O), $SO_2$ or $NR^{12}$, where said $C_{1-6}$ aliphatic, aryl or HET is optionally substituted by one to three of halo, another HET, aryl, CN, $NO_2-R^{12}$, $-SR^{12}$, $-OR^{12}$, $-N(R^{12})_2$, $-R^{12}N(R^{12})_2-S(O)R^{12}$, $-SO_2R^{12}$, $-SO_2N(R^{12})_2$, $-NR^{12}COR^{12}$, $-NR^{12}CO_2R^{12}$, $-NR^{12}CON(R^{12})_2$, $-NR^{12}(NR^{12})NHR^{12}$, $-CO_2R^{12}$, $-CON(R^{12})_2$, $-NR^{12}SO_2R^{12}$, $-OCON(R^{12})_2$, or trifluoro, where HET and $R^{12}$ are as defined below;

$R^{11}$ is H or $R^{10}$;

$R^{12}$ is H, $C_{1-6}$ aliphatic, $NO_2$, $C_{1-6}$ alkoxy, halogen, aryl or HET, said $C_{1-6}$ aliphatic optionally substituted by one to three of halogen or OH where HET is as defined below;

HET is a five or six-membered saturated or unsaturated heteroaryl ring selected from the group consisting of dioxin, dioxane, dioxolane, dithiane, dithiazine, dithiazole, dithiolane, furan, imidazole, imidazopyridinyl, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, tetrahydrofuran, tetrazine, thiophene, thiadiazine, thiadiazole, thiatriazole, thiazine, thiazole, thiomorpholine, thiopyran, thioxotriazine, triazine, and triazole;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

Also highly preferred is a compound of formula (I) in which $R^1$ and $R^2$ additionally comprise a fused ring which is methyl substituted fused pyridine.

A group of compounds that are preferred with respect to their substituents at positions $R^6$, $R^7$ and $R^8$ are compounds of the formula:

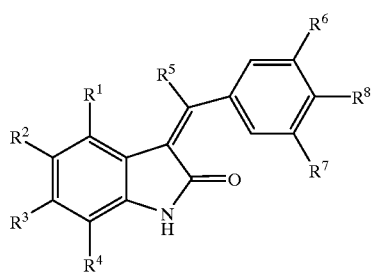

(I)

wherein:

$R^1$ is H or optionally joined with $R^2$ to form a fused ring selected from the group consisting of five to ten membered aryl, heteroaryl or heterocyclyl rings, said heteroaryl or said heterocyclyl rings having zero to three heteroatoms where zero to three of said heteroatoms are N and zero to 1 of said heteroatoms are O or S and where said fused ring is optionally substituted by one to three of $R^9$, where $R^2$ and $R^9$ are as defined below;

$R^2$ and $R^3$ are independently H, HET, aryl, $C_{1-12}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^1$ where said $C_{1-12}$ aliphatic optionally bears one or two insertions of one to two groups selected from C(O), O, S, S(O), $SO_2$ or $NR^{12}$; with said HET, aryl or $C_{1-12}$ aliphatic being optionally substituted by one to three of $R^{10}$; and where $R^2$ is optionally joined with $R^3$ to form a fused ring selected from the group consisting of five to ten membered aryl, heteroaryl or heterocyclyl rings, said heteroaryl or said heterocyclyl rings having zero to three heteroatoms where zero to three of said heteroatoms are N and zero to one of said heteroatoms are O or S and where said fused ring is optionally substituted by one to three of $R^9$, where HET, $R^9$, $R^{10}$, $R^{11}$ and $R^{12}$ are as defined below;

$R^4$ is H, halogen, $NO_2$ or CN;

$R^5$ is H or $C_{1-12}$ aliphatic optionally substituted by one to three of halo, hydroxyl, or aryl;

$R^6$ and $R^7$ are halogen;

$R^8$ is OH;

$R^9$ is each independently halogen, $C_{1-12}$ aliphatic, CN, $-NO_2$, $R^{10}$, $-OR^{11}$, $-SR^{11}$, $-S(O)R^{10}$, $-SO_2R^{10}$, $-NR^{10}R^{11}$, $-N^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-CO_2R^{11}$, $-CONR^{12}R^{11}$, $-SO_2NR^{12}R^{11}$, $-OCONR^{12}R^{11}$ or $C(NR^{12})NR^{12}R^{11}$, where $R^{10}$, $R^{11}$ and $R^{12}$ are as defined below;

$R^{10}$ is each independently H, halogen, $C_{1-12}$ aliphatic, aryl or HET, where said $C_{1-12}$ aliphatic optionally bears an inserted one to two groups selected from O, S, S(O), $SO_2$ or $NR^{12}$, where said $C_{1-12}$ aliphatic, aryl or HET is optionally substituted by one to three of halo, another HET, aryl, CN, $-SR^{12}$, $-OR^{12}$, $-N(R^{12})_2$, $-S(O)R^{12}$, $-SO_2R^{12}$, $-SO_2N(R^{12})_2$, $-NR^{12}COR^{12}$, $-NR^{12}CO_2R^{12}$, $-NR^{12}CON(R^{12})_2$, $-NR^{12}(NR^{12})NHR^{12}$, $-CO_2R^{12}$, $-CON(R^{12})_2$, $-NR^{12}SO_2R^{12}$, $-OCON(R^{12})_2$, where HET and $R^{12}$ are as defined below;

$R^{11}$ is H or $R^{10}$;

$R^{12}$ is H, $C_{1-12}$ aliphatic or HET, said $C_{1-12}$ aliphatic optionally substituted by one to three of halogen or OH where HET is as defined below; and HET is a five to ten-membered saturated or unsaturated heterocyclic ring selected from the group consisting of benzofuran, benzoxazole, dioxin, dioxane dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

Another group of compounds that are preferred with respect to their substituents at positions $R^6$ $R^7$ and $R^8$ are compounds of the formula:

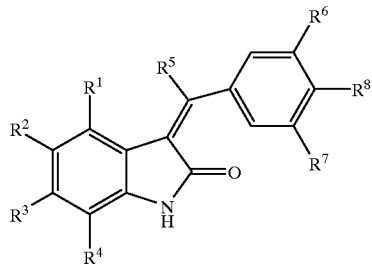

(I)

wherein:

$R^1$ is H or optionally joined with $R^2$ to form a fused ring selected from the group consisting of five to ten membered aryl, heteroaryl or heterocyclyl rings, said heteroaryl or said heterocyclyl rings having one to three heteroatoms where zero to three of said heteroatoms are N and zero to 1 of said heteroatoms are O or S and where said fused ring is optionally substituted by one to three of $R^9$, where $R^2$ and $R^9$ are as defined below;

$R^2$ and $R^3$ are independently H, HET, aryl, $C_{1-12}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^{11}$ where said $C_{1-12}$ aliphatic optionally bears one or two insertions of one to two groups selected from C(O), O, S, S(O), $SO_2$ or $NR^{12}$; with said HET, aryl or $C_{1-12}$ aliphatic being optionally substituted by one to three of $R^{10}$; and where $R^2$ is optionally joined with $R^3$ to form a fused ring selected from the group consisting of five to ten membered aryl, heteroaryl or heterocyclyl rings, said heteroaryl or said heterocyclyl rings having zero to three heteroatoms where zero to three of said heteroatoms are N and zero to one of said heteroatoms are O or S and where said fused ring is optionally substituted by one to three of $R^9$, where HET, $R^9$, $R^{10}$, $R^{11}$ and $R^{12}$ are as defined below;

$R^4$ is H, halogen, $NO_2$ or CN;

$R^5$ is H or $C_{1-12}$ aliphatic optionally substituted by one to three of halo, hydroxyl, or aryl;

$R^6$ and $R^7$ are independently bromo or chloro;

$R^8$ is OH;

$R^9$ is each independently halogen, $C_{1-12}$ aliphatic, CN, $-NO_2$, $R^{10}$, $-OR^{11}$, $-SR^{11}$, $-S(O)R^{10}$, $-SO_2R^{10}$, $-NR^{10}R^{11}$, $-N^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-CO_2R^{11}$, $-CONR^{12}R^{11}$, $-SO_2NR^{12}R^{11}$, $-OCONR^{12}R^{11}$ or $C(NR^{12})NR^{12}R^{11}$, where $R^{10}$, $R^{11}$ and $R^{12}$ are as defined below;

$R^{10}$ is each independently H, halogen, $C_{1-12}$ aliphatic, aryl or HET, where said $C_{1-12}$ aliphatic optionally bears an inserted one to two groups selected from O, S, S(O), $SO_2$ or $NR^{12}$, where said $C_{1-12}$ aliphatic, aryl or HET is optionally substituted by one to three of halo, another HET, aryl, CN, $-SR^{12}$, $-OR^{12}$, $-N(R^{12})_2$, $-S(O)R^{12}$, $-SO_2R^{12}$, $-SO_2N(R^{12})_2$, $-NR^{12}COR^{12}$, $-NR^{12}CO_2R^{12}$, $-NR^{12}CON(R^{12})_2$, $-NR^{12}(NR^{12})NHR^{12}$, $-CO_2R^{12}$, $-CON(R^{12})_2$, $-NR^{12}SO_2R^{12}$, $-OCON(R^{12})_2$, where HET and $R^{12}$ are as defined below;

$R^{11}$ is H or $R^{10}$;

$R^{12}$ is H, $C_{1-12}$ aliphatic or HET, said $C_{1-12}$ aliphatic optionally substituted by one to three of halogen or OH where HET is as defined below; and HET is a five to ten-membered saturated or unsaturated heterocyclic ring selected from the group consisting of benzofuran, benzoxazole, dioxin, dioxane dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

Yet another group of compounds that are preferred with respect to their substituents at positions $R^6$, $R^7$ and $R^8$ are compounds of the formula:

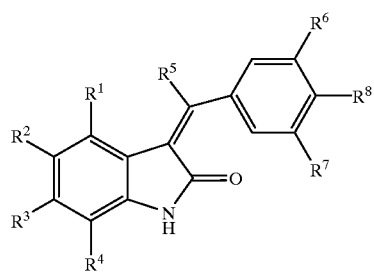

(I)

wherein $R^1$ is H or optionally joined with $R^2$ to form a fused ring selected from the group consisting of five to six membered heteroaryl rings, said heteroaryl ring having one to two heteroatoms where zero to two of said heteroatoms are N and zero to two of said heteroatoms are O or S and where said fused ring is optionally substituted by one to three of $R^9$, where $R^2$ and $R^9$ are as defined below;

$R^2$ and $R^3$ are independently H, HET, phenyl, $C_{1-6}$ aliphatic, $-NR^{10}OR^{11}$, $-COR^{11}$, $-CO_2R^{11}$, $-CONR^{12}R^{11}$, $-SO_2NR^{12}R^{11}$, with said HET, phenyl or $C_{1-6}$ aliphatic being optionally substituted by $R^{10}$; and where $R^2$ is optionally joined with $R^3$ to form a fused five membered heterocyclyl ring, said heterocyclyl ring having zero to 1 heteroatoms where said heteroatom is N and zero to 1 heteroatoms where said heteroatoms are O or S and where said fused ring is optionally substituted by $R^9$, where HET, $R^9$, $R^{10}$, $R^{11}$ and $R^{12}$ are as defined below;

$R^4$ is H;

$R^5$ is H;

$R^6$ and $R^7$ are independently bromo or chloro;

$R^8$ is OH;

$R^9$ is H, $C_{1-6}$ aliphatic, or $-COR^{10}$, where $R^{10}$ is as defined below;

$R^{10}$ is H, $C_{1-6}$ aliphatic or amino;

$R^{11}$ is H, $C_{1-6}$ aliphatic, hydroxy-$C_{1-6}$ aliphatic, phenyl, phenyl-$C_{1-6}$ aliphatic or HET;

$R^{12}$ is H, $C_{1-6}$ aliphatic, hydroxy-$C_{1-6}$ aliphatic or $(R^{11})_2$ N—$C_{1-6}$ aliphatic; and HET is a heterocyclic ring selected from the group consisting of oxazole, pyridine, tetrazole and thiazole;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

Still another group of compounds that are preferred with respect to their substituents at positions $R^6$, $R^7$ and $R^8$ are compounds of the formula:

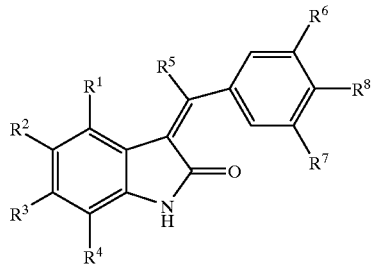
(I)

wherein $R^1$ is H;

$R^2$ and $R^3$ are independently H, HET, phenyl, $C_{1-6}$ aliphatic, cyano, halogen, —$COR^{11}$, or —$CONR^{12}R^{11}$, with said HET, phenyl or $C_{1-6}$ aliphatic being optionally substituted by $R^{10}$, where HET, $R^{10}$, $R^{11}$ and $R^{12}$ are as defined below;

$R^4$ is H;

$R^5$ is H;

$R^6$ and $R^7$ are independently bromo or chloro;

$R^8$ is OH;

$R^{10}$ is H, $C_{1-6}$ aliphatic, oxo or cyano;

$R^{11}$ is H, $C_{1-6}$ aliphatic, trihalo-$C_{1-6}$ aliphatic, phenyl or nitro-substituted phenyl;

$R^{12}$ is H, $C_{1-6}$ aliphatic, hydroxy-$C_{1-6}$ aliphatic; and

HET is thiophene or pyridine;

and the pharmaceutically acceptable salts, biohydrolyzable esters, biohydolyzable amides, biohydrolyzable carbamates, biohydrolyzable carbonates, biohydrolyzable ureides, solvates, hydrates, affinity reagents or prodrugs of (I) as defined above.

Certain compounds of formula (I) above may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

Due to the presence of a double bond, also included in the compounds of the invention are their respective pure E and Z geometric isomers as well as mixtures of E and Z isomers.

Z-isomer

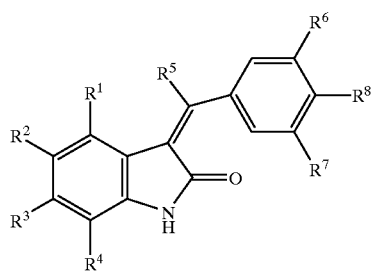

E-isomer

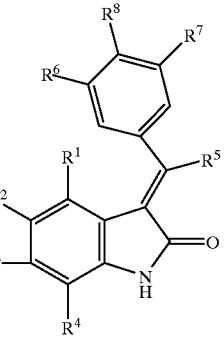

E/Z mixture

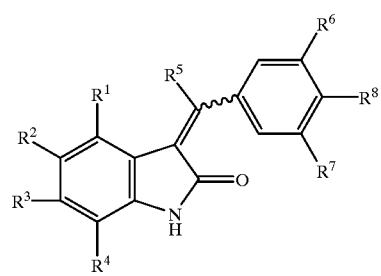

E/Z Mixture

The invention as described and claimed does not set any limiting ratios on prevalence of Z to E isomers.

Thus, compound 3-(3,5-Dibromo-4-hydroxybenzylidene)-5-pyrid-3-yl-1,3-dihydro-indol-2-one, compound number 138 in the tables below, is disclosed and claimed as the E geometric isomer thereof, the Z geometric isomer and a mixture of the E and Z geometric isomers thereof, but not limited by any given ratio(s).

Certain of the compounds as described will contain one or more chiral carbons and will therefore be either dextrorotatory or levorotatory. Also included in the compounds of the invention are the respective dextrorotatory or levorotatory pure preparations, and racemic mixtures thereof.

Salts of the compounds of the present invention may comprise acid addition salts derived from a nitrogen on a substituent in the compound of formula (I). The therapeutic activity resides in the moiety derived from the compound of the invention as defined herein and the identity of another component is of less importance although for therapeutic and prophylactic purposes it is, preferably, pharmaceutically acceptable to the patient.

Highly preferred biohydrolyzable carbamates comprise compounds of formula (i), wherein $R^8$ is OH and said OH is conjugated with a carbamoyl conjugate to yield a biohydrolyzable carbamate wherein said carbamoyl conjugate is selected from the group consisting of diethylaminocarbonyl, N-(2-hydroxyethyl)aminocarbonyl, N,N,-bis(2-hydroxyethyl)aminocarbonyl, hydroxyethyloxyethylaminocarbonyl, 4-morpholinocarbonyl and 4-methyl-1-piperazinylcarbonyl.

Highly preferred biohydrolyzable carbonates comprise compounds of formula (I), wherein $R^8$ is OH and said OH is conjugated with a carbonate conjugate to yield a biohydrolyzable carbonate wherein said carbonyl conjugate is selected from the group consisting of phenylmethyloyxcarbonyl, ethyloxycarbonyl, isobutyloxycarbonyl, and pyridinemethyloxycarbonyl.

Highly preferred biohydrolyzable esters comprise compounds of formula (I), wherein $R^8$ is OH and said OH is conjugated with an ester conjugate to yield a biohydrolyzable ester wherein said ester conjugate is selected from the group consisting of t-butylcarbonyloxymethyl.

The invention further includes a compound of formula (I) or one of its pharmaceutically acceptable salts, prodrugs, biohydrolyzable esters, amides, carbonates, amines, ureides or carbamates for use in the preparation of a medicament for the treatment of disorders mediated by protein kinase activity.

The invention further includes a compound of formula (I) or one of its pharmaceutically acceptable salts, prodrugs, biohydrolyzable esters, amides, carbonates, amines, ureides or carbamates for use in the preparation of a medicament for the treatment of disorders mediated by disorders caused by a mutated ras gene.

The invention further includes a compound of formula (I) or one of its pharmaceutically acceptable salts, prodrugs, biohydrolyzable esters, amides, carbonates, amines, ureides or carbamates for use in the preparation of a medicament for the treatment of disorders mediated by an upregulated tyrosine kinase signalling pathway.

The invention further includes a compound of formula (I) or one of its pharmaceutically acceptable salts, prodrugs, biohydrolyzable esters, amides, carbonates, amines, ureides or carbamates for use in the preparation of a medicament for the treatment of disorders mediated by a mitogen activated protein kinase.

The invention further includes a compound of formula (I) or one of its pharmaceutically acceptable salts, prodrugs, biohydrolyzable esters, amides, carbonates, amines, ureides or carbamates for use in the preparation of a medicament for the treatment of disorders mediated by cRaf kinase.

A group of preferred species of compounds of the present invention comprises the group:

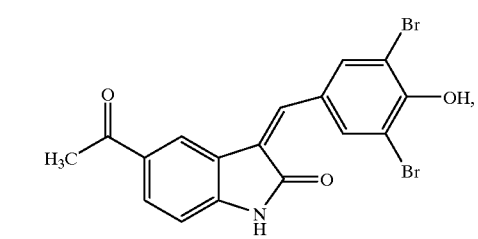

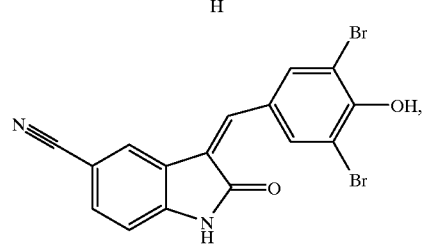

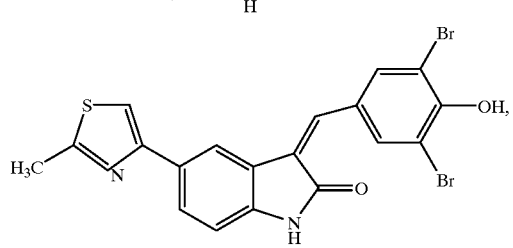

-continued

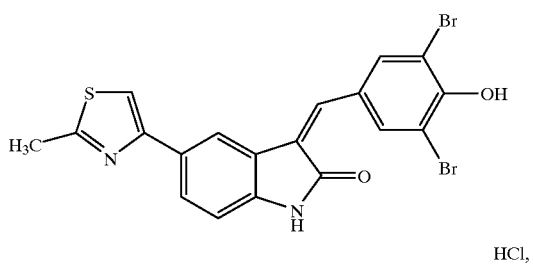

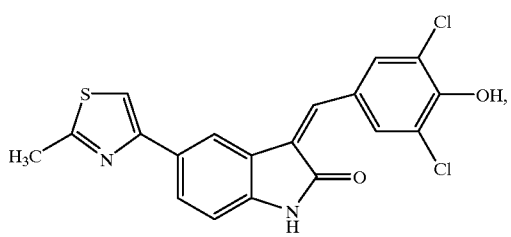

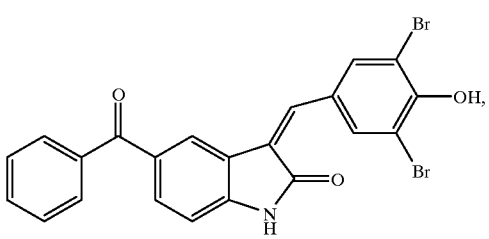

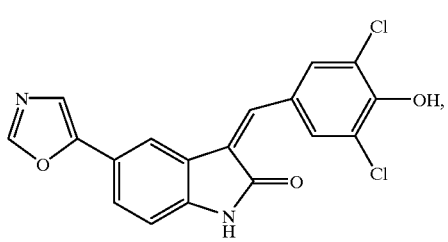

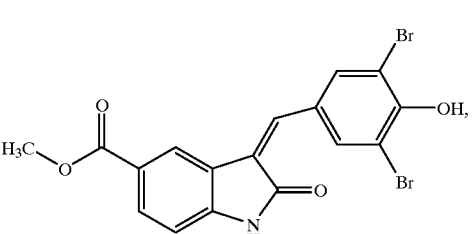

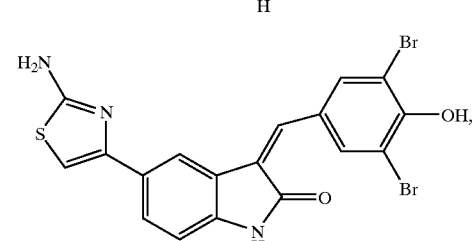

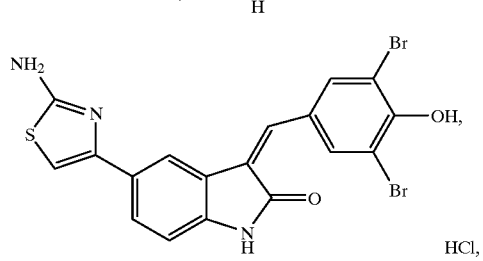

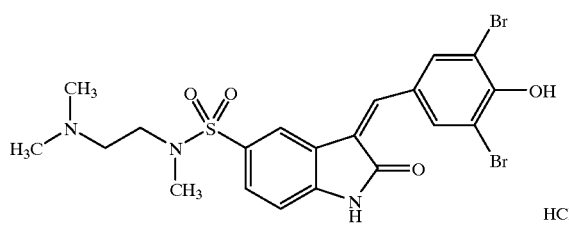
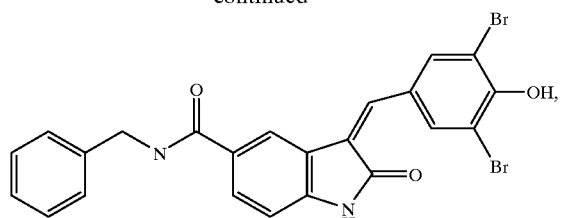
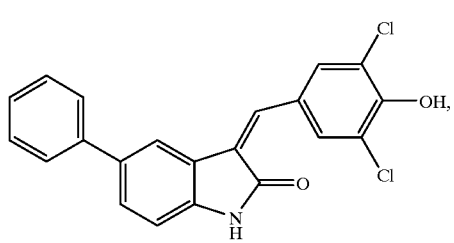
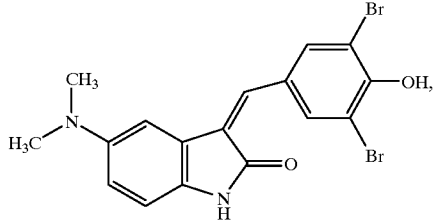
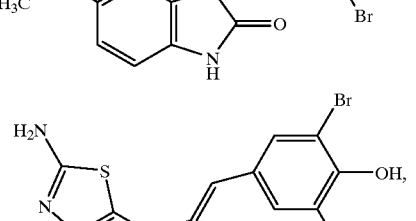
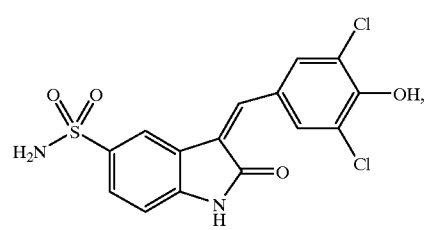
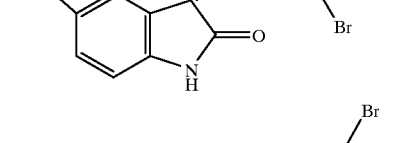
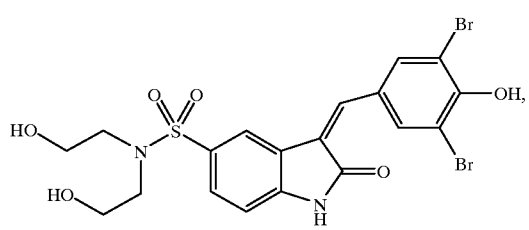
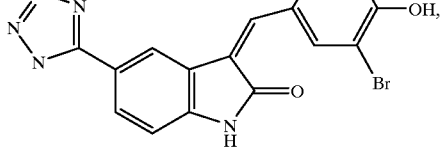
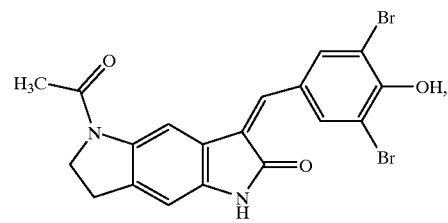
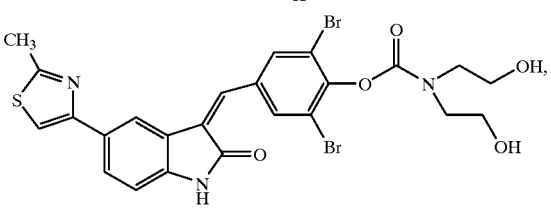
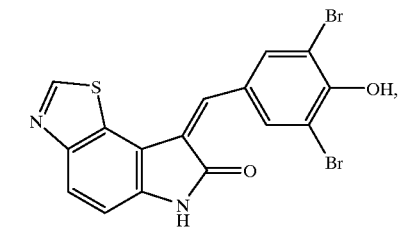
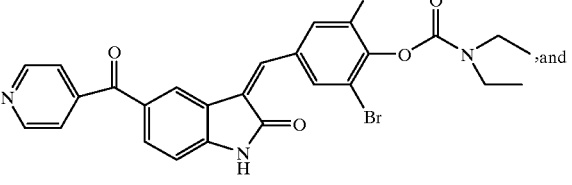
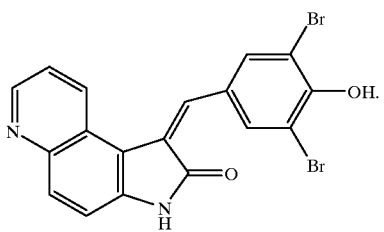
Another group of preferred compounds of the invention comprises the group.

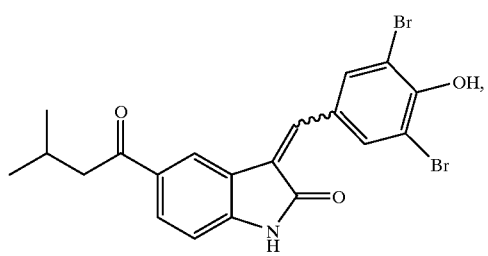
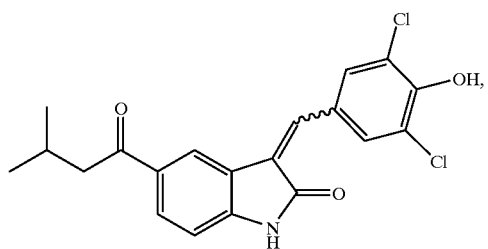
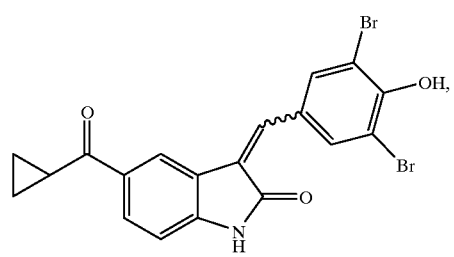
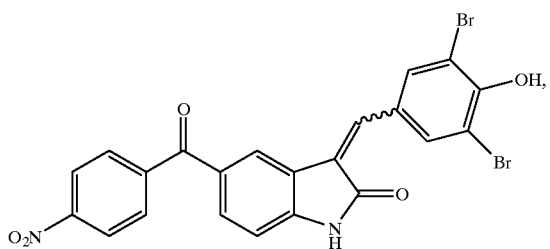
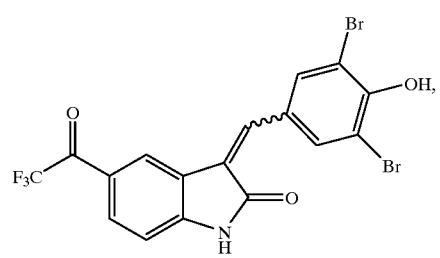
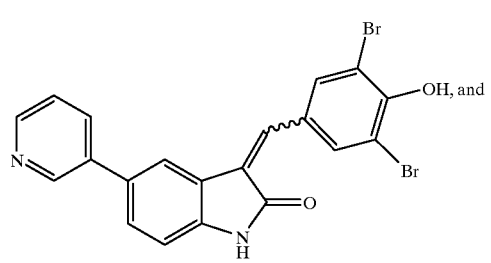
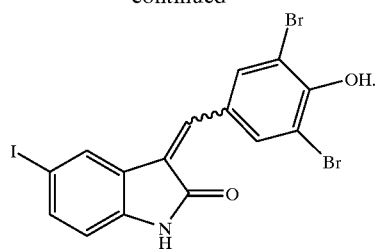
Still another group of preferred compounds comprises the group:
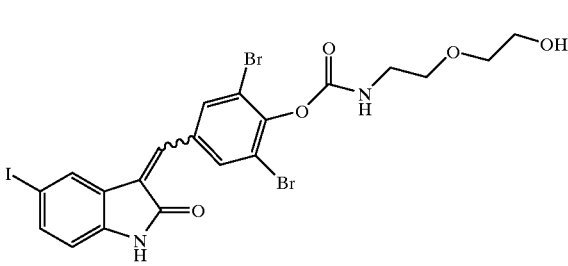
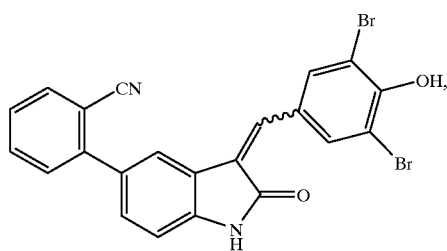
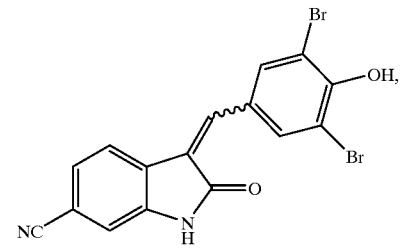
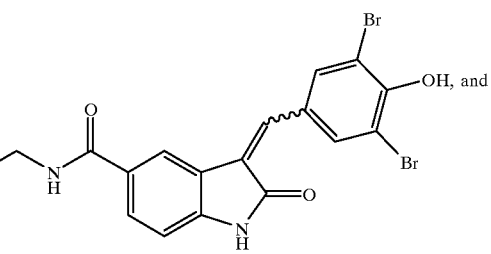
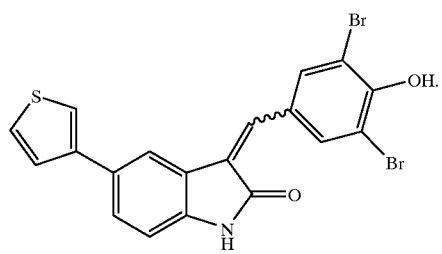
An especially preferred group of compounds comprises the group:

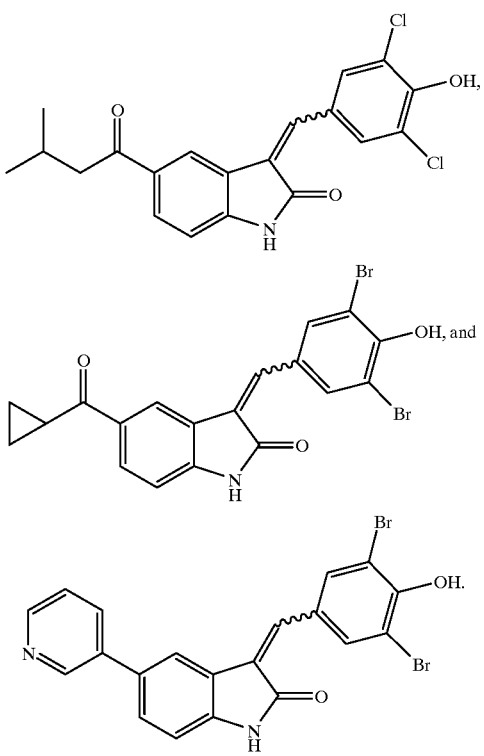

Independent Substituents

The invention discloses eight different points of substitution on structural formula (I). Each of these points of substitution bears a substituent whose selection and synthesis as part of this invention was independent of all other points of substitution on formula (I). Thus, each point of substitution is now further described individually.

$R^1$ is hydrogen. Optionally, $R^1$ can be joined with an $R^2$ substituent to form a fused ring. Such fused rings can be five to ten membered aryl, heteroaryl, or heterocyclyl rings or ring systems, having 1 to 3 heteroatoms. These heteroatoms can be nitrogen, oxygen or sulfur. Such fused rings can be optionally substituted by one to three groups of halogen, cyano, nitro, substituted amide, substituted sulfonamide, substituted amine, substituted ether or hydroxyl. Substitutents for am ides, sulfonamides, amines, or ethers include hydrogen, halogen, 1 to 12 carbon aliphatic (which can bear an insertede group anywhere along its chain length of an oxygen, a sulfur, a sulfoxide, a sulfone, a sulfine, or a secondary amine), aryl rings, heterocyclic ring. Substituents on these aliphatic aryl or heterocyclic groups include 1 to 3 substitutions by a halogen, another heterocyclic ring, another aryl ring, cyano, substituted sulfo, substituted oxy, substituted amine, substituted sulfoxide, substituted sulfine, substituted sulfone, substituted sulfonamide, substituted amide, substituted ureide, substituted ester, substituted carbamate. These substituents in turn can be 1 to 12 carbon aliphatic or a heterocyclic ring, where the 1 to 12 carbon aliphatic itself can be substituted by 1 to 3 occurences of a halogen, or hydroxyl.

Alternatively, $R^1$ can be hydrogen or optionally, $R^1$ can be joined with an $R^2$ substituent to form a fused ring. Such fused rings can be from the group comprising benzofuran, benzoxazole, dioxin, dioxane, dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole. Any of these rings can in turn be substituted by a group from the substituents comprising 1 to 3 substitutions by a halogen, another heterocyclic ring, another aryl ring, cyano, substituted sulfo, substituted oxy, substituted amine, substituted sulfoxide, substituted sulfine, substituted sulfone, substituted sulfonamide, substituted amide, substituted ureide, substituted ester, or substituted carbamate. These substituents in turn can be 1 to 12 carbon aliphatic or a heterocyclic ring, where the 1 to 12 carbon aliphatic itself can be substituted by 1 to 3 occurences of a halogen, or hydroxyl.

Preferably, $R^1$ is hydrogen or fused with $R^2$ to form fused pyridine, fused triazole, fused thiazole or fused amino-substituted thiazole.

Most preferably, $R^1$ is hydrogen.

$R^2$ is hydrogen, an aryl ring, a heterocyclic ring, a 1 to 12 carbon aliphatic, cyano, nitro, halogen, substituted ether, substituted thioether, substituted sulfine, substituted sulfone, substituted amine, disubstituted amine, substituted amide, substituted carbamate, substituted sulfonamide, substituted carbonyl, or substituted ester. These substituents can be hydrogen, halogen, 1 to 12 carbon aliphatic (which can bear an inserted group anywhere along its chain length of an oxygen, a sulfur, a sulfoxide, a sulfone, a sulfine, or a secondary amine), aryl rings, heterocyclic rings. Substituents on these aliphatic, aryl or heterocyclic groups include 1 to 3 substitutions by a halogen, another heterocyclic ring, another aryl ring, cyano, substituted sulfo, substituted oxy, substituted amine, substituted sulfoxide, substituted sulfine, substituted sulfone, substituted sulfonamide, substituted amide, substituted ureide, substituted ester, substituted carbamate. These substituents in turn can be 1 to 12 carbon aliphatic or a heterocyclic ring, where the 1 to 12 carbon aliphatic itself can be substituted by 1 to 3 occurences of a halogen, or hydroxyl.

$R^2$ can be joined with $R^3$ to form a fused ring selected from the group comprising benzofuran, benzoxazole, dioxin, dioxane, dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole.

$R^2$ can more preferably be hydrogen, a heterocyclic ring, phenyl, a 1 to 6 carbon aliphatic, a substituted amine, a substituted carbonyl, a substituted ester, a substituted amide, or a substituted sulfonamide. Said heterocyclic ring, phenyl or aliphatic group are optionally substituted by amino or 1 to 6 carbon aliphatic. Said amine, carbonyl, ester amide or sulfonamide are optionally substituted by 1 to 6 carbon aliphatic, amino, hydroxy-aliphatic of 1 to 6 carbons, phenyl, phenyl-aliphatic of 1 to 6 carbons, amino-aliphatic of 1 to 12 carbons or heterocyclic rings such as oxazole, pyridine, tetrazole or thiazole.

$R^2$ can more preferably be joined with $R^3$ to form a five membered fused ring having a heteroatom of either nitrogen, oxygen or sulfur. These fused rings can be substituted by 1 to 6 carbon aliphatic, or a 1 to 6 carbon acyl group.

$R^2$ can also more preferably be hydrogen, thiophene, pyridine, phenyl, 1 to 6 carbon aliphatic, cyano, halogen, substituted acyl, or substituted amide. These substituents can be 1 to 6 carbon aliphatic, tri-halogen 1 to 6 carbon aliphatic, phenyl, nitro-substituted phenyl, or hydroxy-aliphatic of 1 to 6 carbons.

$R^2$ is hydrogen, an aryl ring, a heterocyclic ring, a 1 to 12 carbon aliphatic, cyano, nitro, halogen, substituted ether, substituted thioether, substituted sulfine, substituted sulfone, substituted amine, disubstituted amine, substituted amide, substituted carbamate, substituted sulfonamide, substituted carbonyl, or substituted ester. These substituents can be hydrogen, halogen, 1 to 12 carbon aliphatic (which can bear an inserted group anywhere along its chain length of an oxygen, a sulfur, a sulfoxide, a sulfone, a sulfine, or a secondary amine), aryl rings, heterocyclic rings. Substituents on these aliphatic, aryl or heterocyclic groups include 1 to 3 substitutions by a halogen, another heterocyclic ring, another aryl ring, cyano, substituted sulfo, substituted oxy, substituted amine, substituted sulfoxide, substituted sulfine, substituted sulfone, substituted sulfonamide, substituted amide, substituted ureide, substituted ester, substituted carbamate. These substituents in turn can be 1 to 12 carbon aliphatic or a heterocyclic ring, where the 1 to 12 carbon aliphatic itself can be substituted by 1 to 3 occurences of a halogen, or hydroxyl.

$R^3$ can be joined with $R^2$ to form a fused ring selected from the group comprising benzofuran, benzoxazole, dioxin, dioxane, dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole.

$R^3$ can more preferably be hydrogen, a heterocyclic ring, phenyl, a 1 to 6 carbon aliphatic, a substituted amine, a substituted carbonyl, a substituted ester, a substituted amide, or a substituted sulfonamide. Said heterocyclic ring, phenyl or aliphatic group are optionally substituted by amino or 1 to 6 carbon aliphatic. Said amine, carbonyl, ester amide or sulfonamide are optionally substituted by 1 to 6 carbon aliphatic, amino, hydroxy-aliphatic of 1 to 6 carbons, phenyl, phenyl-aliphatic of 1 to 6 carbons, amino-aliphatic of 1 to 12 carbons or heterocyclic rings such as oxazole, pyridine, tetrazole or thiazole.

$R^3$ can more preferably be joined with $R^2$ to form a five membered fused ring having a heteroatom of either nitrogen, oxygen or sulfur. These fused rings can be substituted by 1 to 6 carbon aliphatic, or a 1 to 6 carbon acyl group.

$R^3$ can also more preferably be hydrogen, thiophene, pyridine, phenyl, 1 to 6 carbon aliphatic, cyano, halogen, substituted acyl, or substituted amide. These substituents can be 1 to 6 carbon aliphatic, tri-halogen 1 to 6 carbon aliphatic, phenyl, nitro-substituted phenyl, or hydroxy-aliphatic of 1 to 6 carbons.

$R^4$ is hydrogen, nitro, cyano, or halogen.

Preferably, $R^4$ is hydrogen.

$R^5$ is hydrogen or 1 to 12 carbon aliphatic, which is optionally substituted at 1 to 3 positions by a halogen, hydroxyl, or an aryl ring.

$R^5$ is alternatively hydrogen or 1 to 6 carbon aliphatic, which is optionally substituted at 1 to 3 positions by a halogen, hydroxyl or an aryl ring.

Preferably, $R^5$ is hydrogen.

$R^6$ is halogen, cyano, nitro, substituted amide, substituted sulfonamide, substituted amine, substituted ether or hydroxyl. Substitutents for amides, sulfonamides, amines, or ethers include hydrogen, halogen, 1 to 12 carbon aliphatic (which can bear an inserted group anywhere along its chain length of an oxygen, a sulfur, a sulfoxide, a sulfone, a sulfine, or a secondary amine), aryl rings, heterocyclic rings. Substituents on these aliphatic, aryl or heterocyclic groups include 1 to 3 substitutions by a halogen, another heterocyclic ring, another aryl ring, cyano, substituted sulfo, substituted oxy, substituted amine, substituted sulfoxide, substituted sulfine, substituted sulfone, substituted sulfonamide, substituted amide, substituted ureide, substituted ester, substituted carbamate. These substituents in turn can be 1 to 12 carbon aliphatic or a heterocyclic ring, where the 1 to 12 carbon aliphatic itself can be substituted by 1 to 3 occurences of a halogen, or hydroxyl.

$R^6$ is more preferably a halogen.

$R^6$ is most preferably a bromine.

Alternatively, $R^6$ is most preferably a chlorine.

$R^7$ is halogen, cyano, nitro, substituted amide, substituted sulfonamide, substituted amine, substituted ether or hydroxyl. Substitutents for amides, sulfonamides, amines, or ethers include hydrogen, halogen, 1 to 12 carbon aliphatic (which can bear a n inserted group anywhere along its chain length of an oxygen, a sulfur, a sulfoxide, a sulfone, a sulfine, or a secondary amine), aryl rings, heterocyclic rings. Substituents on these aliphatic, aryl or heterocyclic groups include 1 to 3 substitutions by a halogen, another heterocyclic ring, another aryl ring, cyano, substituted sulfo, substituted oxy, substituted amine, substituted sulfoxide, substituted sulfine, substituted sulfone, substituted sulfonamide, substituted amide, substituted ureide, substituted ester, substituted carbamate. These substituents in t urn can be 1 to 12 carbon aliphatic or a heterocyclic ring, where the 1 to 12 carbon aliphatic itself can be substituted by 1 to 3 occurences of a halogen, or hydroxyl.

$R^7$ is more preferably a halogen.

$R^7$ is most preferably a bromine.

Alternatively, $R^7$ is most preferably a chlorine.

$R^8$ is hydroxy or sulfonamide optionally substituted by a 1 to 12 carbon aliphatic, or substituted by a heterocyclic ring. This aliphatic group itself can be substituted by 1 to 3 halogens or hydroxy.

Alternatively, $R^8$ is hydroxy or $NHCOCF_3$, or sulfonamide optionally substituted by a 1 to 6 carbon aliphatic, or substituted by a heterocyclic ring.

Or, $R^8$ is hydroxy or NHCOCF3, or sulfonamide optionally substituted by a 1 to 6 carbon aliphatic, a nitro, a 1 to 6 carbon alkoxy, a halogen, an aryl or a hetercyclic ring. This aliphatic group itself be substituted by 1 to 3 halogens or hydroxy.

Preferably, $R^8$ is hydroxy.

In further aspect, the present invention provides a process for the preparation of a compound of the formula (I), which process comprises the reaction of a compound of the formula (II)

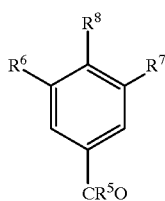

with a compound of the formula (III)

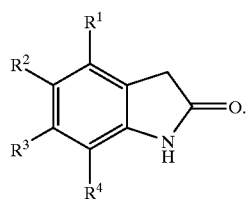

The reaction is conveniently carried out in the presence of a catalytic acid in the presence of a suitable inert solvent, for example an aromatic hydrocarbon or a halogenated hydrocarbon at a non-extreme temperature, for example from 0° C. to 150°C., preferably 80°C. to 110°C. Optionally the reaction is carried out in the presence of a strong acid, for example hydrochloric acid or sulfuric acid, in acetic acid as the solvent.

The preparation of compounds (II) and (III) is well known to those skilled in the art and many compounds having formula (II) are commercially available. (P. G. Gassman; T. J. vanBergen, Oxindoles. A New General Method of Synthesis. Journal of the American Chemical Society, 96 (17), 1974, 5508–5512.) ( Jutz, Adv. Org. Chem., 9, 225–342, 1975; Truce, Org. React., 9, 37–72. 1957).

In addition to the above, one compound of formula (I) may be converted to another compound of formula (I) by chemical transformation of the appropriate substituent or substituents.

The present invention also provides compounds of formula (I) and pharmaceutically acceptable salts, prodrugs, biohydrolyzable esters, amides, carbonates, amines, ureides or carbamates thereof (hereinafter identified as the 'active compounds') for use in medical therapy, and particularly in the treatment of disorders mediated by protein kinase activity such as human malignancies. The compounds are especially useful for the treatment of disorders which are caused by mutated ras and upregulated tyrosine kinase signalling pathways such as breast, colon, lung, pancreatic, prostate, and gastric cancers.

The present invention also provides a method of treating a disease mediated by a kinase selected from the group consisting of ab1, ATK , bcr-ab1, Blk, Brk, Btk, c-kit, c-met, c-src, CDK1, CDK2, CDK4, CDK6, CSF1R, CSK, EGFR, ErbB2, ErbB3, ErbB4, ERK, Fak, fes, FGFR1, FGFR2, FGFR3, FGFR4, FGFR5, Fgr, FLK4, flt-1, Fps, Frk, Fyn, Hck, IGF-1R, INS-R, Jak, KDR, Lck, Lyn, MEK, cRaf1, p38, PDGFR, PIK, PKC, PYK2, ros, $tie_1$, $tie_2$, TRK, Yes, and Zap70, said method comprising the step of administering to a mammal in need thereof a pharmacologically effective amount of an active compound as defined above.

A further aspect of the invention provides a method of treatment of the human or animal body suffering from a disorder mediated by a mitogen activated protein kinase which comprises administering an effective amount of an active compound as defined above to the human or animal patient.

The present invention particularly provides a method of treating a disease meditated by cRaf1 kinase, said method comprising the step of administering to a mammal in need thereof a pharmacologically effective amount of an active compound as defined above.

The present invention also provides a method of inhibiting tumor growth, preventing organ transplant rejection, healing a chronic wound, or of treating a disease state selected from the group consisting of restenosis, rheumatoid arthritis, angiogenesis, hepatic cirrhosis, atherosclerosis, glomerulonephritis, diabetic nephropathy, malignant nephrosclerosis, thrombotic microangiopathy syndromes, glomerulopathy, psoriasis, diabetes mellitus, inflammation, and neurodegenerative disease, comprising the step of administering to a patient in need thereof a pharmacologically effective amount of an active compound as defined above.

Another aspect of the present invention provides the use of an active compound of formula (I), in the preparation of a medicament for the treatment of malignant tumors.

Another aspect of the present invention provides the use of an active compound of formula (I), in coadministration with previously known anti-tumor therapies for more effective treatment of such tumors.

The active compounds of the formula (I) have anticancer activity as demonstrated hereinafter by their inhibition of the protein serine/threonine kinase c-Raf1 enzyme. It has thus been established that compounds of the present invention are of use in medicine and, in particular in the treatment of certain human malignancies, for example breast, ovarian, non-small cell lung, pancreatic, gastric and colon cancers. Accordingly, the present invention provides a method for the treatment of susceptible malignancies in an animal, e.g. a human, which comprises administering to the animal a therapeutically effective amount of an active compound as defined above.

Compounds we have synthesized as part of the present invention which are currently preferred are listed in Tables 1A, 1B and 1C below. Compounds are identified by the numbers shown in the first column; variables below in the rest of the columns are with reference to the generic structure (I). Corresponding IUPAC nomenclature are disclosed in Tables 2A, 2B and 2C, respectively, below. Since all substituents at each point of substitution are capable of independent synthesis of each other, Tables 1A, 1B and 1C are also to be read as a matrix in which any combination of substituents is within the scope of the disclosure and claims of the invention.

TABLE 1A
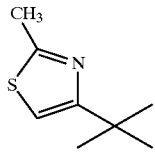
| # | R¹ | R² | R³ | R⁴ | R⁵ | R⁶ | R⁷ | R⁸ |
|---|----|----|----|----|----|----|----|----|
| 1 | H | CN | H | H | H | Br | Br | OH |
| 2 | H | 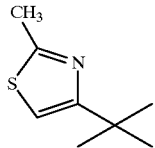 | H | H | H | Br | Br | OH |
| 3 | H | 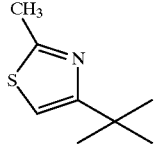 | H | H | H | Br | OEt | OH |
| 4 | H | 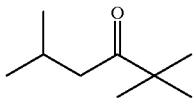 | H | H | H | Cl | Cl | OH |
| 5 | H | 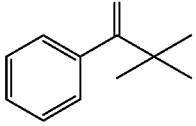 | H | H | H | Br | Br | OH |
| 6 | H | 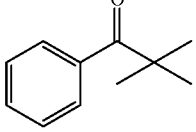 | H | H | H | Br | Br | OH |
| 7 | H | 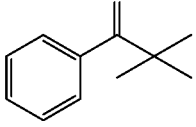 | H | H | H | Cl | Cl | OH |
| 8 | H |  | H | H | H | Br | OEt | OH |

TABLE 1A-continued

| # | R¹ | R² | R³ | R⁴ | R⁵ | R⁶ | R⁷ | R⁸ |
|---|---|---|---|---|---|---|---|---|
| 9 | H | 4-methyl-2,2-dimethylpentan-3-one-yl | H | H | H | Cl | Cl | OH |
| 10 | H | 4-methyl-2,2-dimethylpentan-3-one-yl | H | H | H | Br | OEt | OH |
| 11 | H | 3-pyridyl-C(O)- | H | H | H | Br | Br | OH |
| 12 | H | 3-pyridyl-C(O)- | H | H | H | Cl | Cl | OH |
| 13 | H | 4-pyridyl-C(O)- | H | H | H | Br | Br | OH |
| 14 | H | 4-pyridyl-C(O)- | H | H | H | Br | OEt | OH |
| 15 | H | 4-pyridyl-C(O)- | H | H | H | Cl | Cl | OH |
| 16 | H | 3-pyridyl-C(O)- | H | H | H | Br | OEt | OH |

TABLE 1A-continued
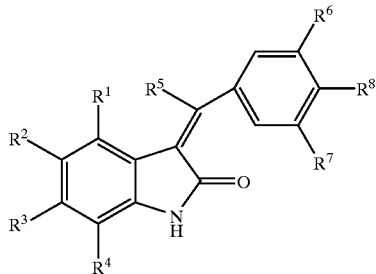
| # | R¹ | R² | R³ | R⁴ | R⁵ | R⁶ | R⁷ | R⁸ |
|---|----|----|----|----|----|----|----|----|
| 17 | H | 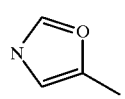 | H | H | H | Cl | Cl | OH |
| 18 | H | 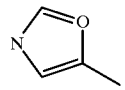 | H | H | H | Br | Br | OH |
| 19 | H | 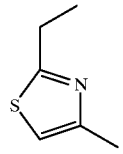 | H | H | H | Br | Br | OH |
| 20 | H | CO₂Me | H | H | H | Br | Br | OH |
| 21 | H | 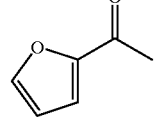 | H | H | H | Br | Br | OH |
| 22 | H | 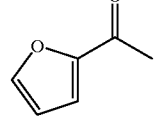 | H | H | H | Cl | Cl | OH |
| 23 | H | 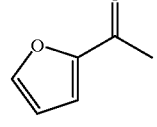 | H | H | H | Br | OEt | OH |
| 24 | H | 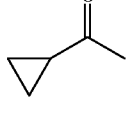 | H | H | H | Br | Br | OH |
| 25 | H |  | H | H | H | Br | Br | OH |
| 26 | H | 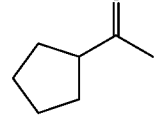 | H | H | H | Br | Br | OH |

TABLE 1A-continued

| # | R¹ | R² | R³ | R⁴ | R⁵ | R⁶ | R⁷ | R⁸ |
|---|----|----|----|----|----|----|----|-----|
| 27 | H | CO₂Me | H | H | H | Cl | Cl | OH |
| 28 | H | H | H | H | H | Br | Br | OH |
| 29 | H | 2-acetylthiophene | H | H | H | Br | Br | OH |
| 30 | H | 2-amino-4-methylthiazolyl | H | H | H | Br | Br | OH |
| 31 | H | 2-methylimidazo[1,2-a]pyridinyl | H | H | H | Br | Br | OH |
| 32 | H | 2-methyl-1-oxobutyl | H | H | H | Br | Br | OH |
| 33 | H | H₂N-SO₂- | H | H | H | Br | Br | OH |
| 34 | H | Et₂N-SO₂-Me | H | H | H | Br | Br | OH |
| 35 | H | pyrrolidinyl-SO₂-Me | H | H | H | Br | Br | OH |
| 36 | H | Me₂N-CH₂CH₂-N(Me)-SO₂-Me | H | H | H | Br | Br | OH |

TABLE 1A-continued

| # | R¹ | R² | R³ | R⁴ | R⁵ | R⁶ | R⁷ | R⁸ |
|---|----|----|----|----|----|----|----|-----|
| 37 | H | ![5-acetylisoxazole group] | H | H | H | Br | Br | OH |
| 38 | H | Cl | H | H | H | Br | Br | OH |
| 39 | H | Cl | H | H | H | Cl | Cl | OH |
| 40 | H | CF₃O | H | H | H | Br | Br | OH |
| 41 | H | Br | H | H | H | Cl | Cl | OH |
| 42 | H | I | H | H | H | Br | OEt | OH |
| 43 | H | I | H | H | H | Br | OMe | OH |
| 44 | H | Br | H | H | H | I | I | OH |
| 45 | H | CF₃O | H | H | H | I | I | OH |
| 46 | H | H | H | H | H | Br | OMe | OH |
| 47 | H | H | H | H | H | NO₂ | NO₂ | OH |
| 48 | H | H | H | H | H | Cl | Cl | OH |
| 49 | H | H | H | H | H | Cl | OMe | OH |
| 50 | H | H | H | H | H | I | I | OH |
| 51 | H | Cl | H | H | H | Br | OMe | OH |
| 52 | H | Cl | H | H | H | NO₂ | NO₂ | OH |
| 53 | H | Cl | H | H | H | OMe | NO₂ | OH |
| 54 | H | Cl | H | H | H | Cl | OMe | OH |
| 55 | H | Cl | H | H | H | I | I | OH |
| 56 | H | Br | H | H | H | Br | OEt | OH |
| 57 | H | Br | H | H | H | Br | OMe | OH |
| 58 | H | F | F | H | H | Br | OMe | OH |
| 59 | H | CF₃O | H | H | H | Br | OEt | OH |
| 60 | H | CF₃O | H | H | H | Cl | Cl | OH |
| 61 | H | CF₃O | H | H | H | Br | OMe | OH |
| 62 | H | NO₂ | H | NO₂ | H | Br | Br | OH |
| 63 | H | NO₂ | H | H | H | Br | Br | OH |
| 64 | H | H | H | I | H | Br | Br | OH |
| 65 | H | NO₂ | H | H | H | Cl | Cl | OH |
| 66 | H | H | H | I | H | Br | Br | OH |
| 67 | H | H | H | Br | H | Cl | Cl | OH |
| 68 | H | NO₂ | H | H | H | Br | OEt | OH |
| 69 | H | (H₂N-C(O)-CH₂-N(CH₃)-CH₂-C(O)-) | H | H | H | Br | Br | OH |
| 70 | H | (HO-C(CH₃)₉-C(O)-N(CH₂CH₂-NO)-CH₂-C(O)-) | H | H | H | Br | Br | OH |
| 71 | H | (1-methylimidazol-3-yl-CH₂-C(O)-) | H | H | H | Br | Br | OH |

TABLE 1A-continued
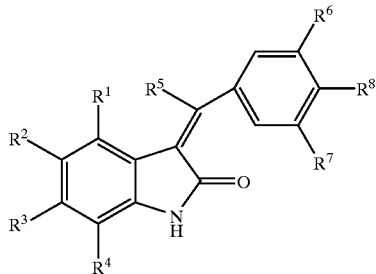
| # | R¹ | R² | R³ | R⁴ | R⁵ | R⁶ | R⁷ | R⁸ |
|---|----|----|----|----|----|----|----|----|
| 72 | H | 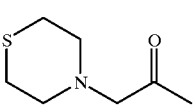 | H | H | H | Br | Br | OH |
| 73 | H | 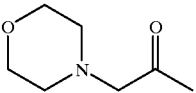 | H | H | H | Br | Br | OH |
| 74 | H | 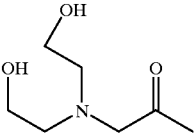 | H | H | H | Br | Br | OH |
| 75 | H | 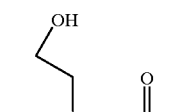 | H | H | H | Br | Br | OH |
| 76 | H | 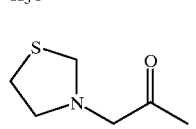 | H | H | H | Br | Br | OH |
| 77 | H | 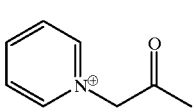 | H | H | H | Br | Br | OH |
| 78 | H | 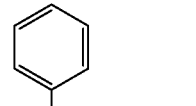 | H | H | H | Br | Br | OH |
| 79 | H | I | H | H | H | Br | Br | OH |
| 80 | H | I | H | H | H | Br | Br | 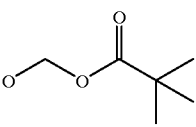 |
| 81 | H | Br | H | H | H | Br | Br | OH |

TABLE 1A-continued

| # | R¹ | R² | R³ | R⁴ | R⁵ | R⁶ | R⁷ | R⁸ |
|---|----|----|----|----|----|----|----|----|
| 82 | H | Br | H | H | H | Cl | OMe | OH |
| 83 | H | CH₃CH₂-N(CH₂CH₃)-CH₂-C(=O)- | H | H | H | Br | Br | OH |
| 84 | H | Cl-CH₂-C(=O)- | H | H | H | Br | Br | OH |
| 85 | H | CH₃CH₂-N(CH₂CH₃)-CH₂-C(=O)- | H | H | H | Cl | Cl | OH |
| 86 | H | Cl-CH₂-C(=O)- | H | I | H | Br | Br | OH |
| 87 | H | I | H | H | H | Br | Br | methyl N,N-bis(2-hydroxyethyl)carbamate |
| 88 | H | Cl-CH₂-C(=O)- | H | H | H | Cl | Cl | OH |
| 89 | H | H₃C-C(=O)- | H | H | H | Br | Br | OH |
| 90 | H | H₃C-C(=O)- | H | H | H | Cl | Cl | OH |
| 91 | H | 3-MeO-C₆H₄-C(=O)- | H | H | H | Br | Br | OH |

TABLE 1A-continued
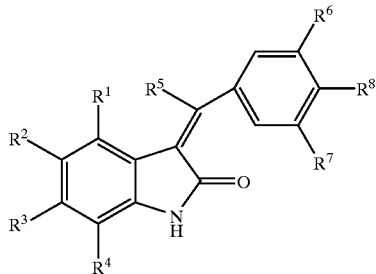
| # | R¹ | R² | R³ | R⁴ | R⁵ | R⁶ | R⁷ | R⁸ |
|---|----|----|----|----|----|----|----|----|
| 92 | H | 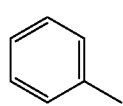 | H | H | H | Br | Br | OH |
| 93 | H | 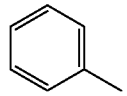 | H | H | H | Cl | Cl | OH |
| 94 | H | 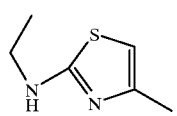 | H | H | H | Br | Br | OH |
| 95 | H | 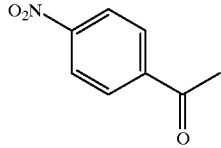 | H | H | H | Br | Br | OH |
| 96 | H | 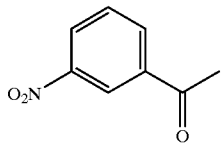 | H | H | H | Br | Br | OH |
| 97 | H | 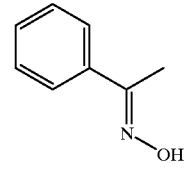 | H | H | H | Br | Br | OH |
| 98 | H | 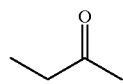 | H | H | H | Cl | Cl | OH |
| 99 | H | 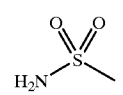 | H | H | H | Cl | Cl | OH |
| 100 | H | 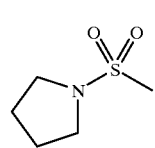 | H | H | H | Cl | Cl | OH |

TABLE 1A-continued
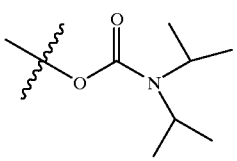
| # | R¹ | R² | R³ | R⁴ | R⁵ | R⁶ | R⁷ | R⁸ |
|---|----|----|----|----|----|----|----|----|
| 101 | H | H | H | H | H | NO₂ | OMe | OH |
| 102 | H | H | H | H | H | OMe | I | OH |
| 103 | H | Cl | H | H | H | Br | Br | OAc |
| 104 | H | I | H | H | H | OMe | NO₂ | OH |
| 105 | H | NO₂ | H | H | H | Cl | OH | OH |
| 106 | H | Cl | H | H | H | Br | Br | 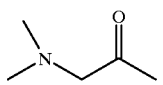 |
| 107 | H | 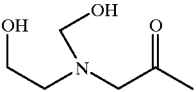 | H | H | H | Br | Br | OH |
| 108 | H | 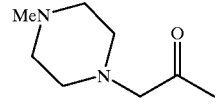 | H | H | H | Br | Br | OH |
| 109 | H | H | H | F | H | Br | Br | OH |
| 110 | H | 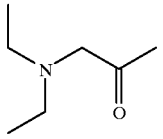 | H | H | H | Br | Br | OH |
| 111 | H | 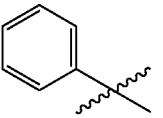 | H | H | H | Br | OEt | OH |
| 112 | H | H | 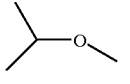 | H | H | Br | Br | OH |
| 113 | H | H | 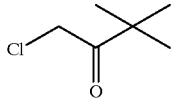 | H | H | Br | Br | OH |
| 114 | H |  | H | H | H | I | I | OH |

TABLE 1A-continued
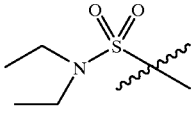
| # | R¹ | R² | R³ | R⁴ | R⁵ | R⁶ | R⁷ | R⁸ |
|---|----|----|----|----|----|----|----|----|
| 115 | H | 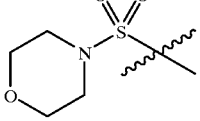 | H | H | H | Cl | Cl | OH |
| 116 | H | 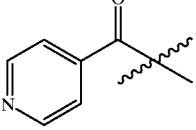 | H | H | H | Cl | Cl | OH |
| 117 | H | 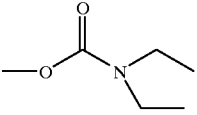 | H | H | H | Br | Br | 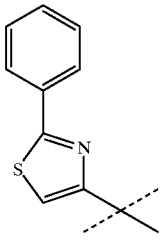 |
| 118 | H | —N(Ac)CH2CH2— | | H | H | Br | Br | OH |
| 119 | | —CH=CH—CH=N— | H | H | H | Br | Br | OH |
| 120 | H | Et | H | H | H | Br | Br | OH |
| 121 | | —S—CH=N— | H | H | H | Br | Br | OH |
| 122 | H | CF₃CO | H | H | H | Br | Br | OH |
| 123 | H | H | Br | H | H | Br | Br | OH |
| 124 | H | 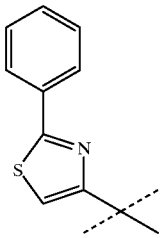 | H | H | H | Cl | Cl | OH |
| 125 | H |  | H | H | H | Br | Br | OH |

TABLE 1A-continued
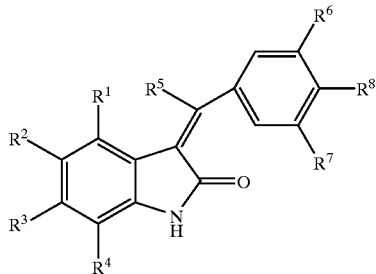
| # | R¹ | R² | R³ | R⁴ | R⁵ | R⁶ | R⁷ | R⁸ |
|---|---|---|---|---|---|---|---|---|
| 126 | H | 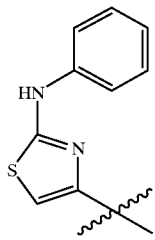 | H | H | H | Br | Br | OH |
| 127 | H | 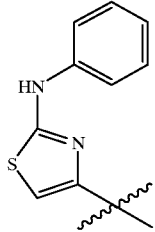 | H | H | H | Cl | Cl | OH |
| 128 | H | 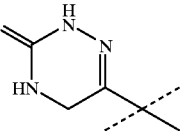 | H | H | H | Cl | Cl | OH |
| 129 | H | 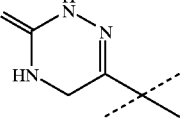 | H | H | H | Br | Br | OH |
| 130 | H | 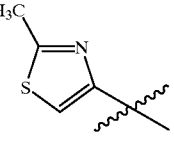 | H | H | H | NO₂ | NO₂ | OH |
| 131 | H | H | H | H | H | NO₂ | NO₂ | OH |
| 132 | —N=N—N— | | H | H | H | Br | Br | OH |
| 133 | H | H | Br | H | H | Cl | Cl | OH |
| 134 | H | 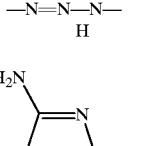 | H | H | H | Cl | Cl | OH |
| 135 | —N=C(NH₂)—S— | | H | H | H | Br | Br | OH |

TABLE 1A-continued
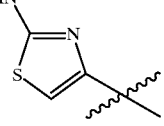
| # | R¹ | R² | R³ | R⁴ | R⁵ | R⁶ | R⁷ | R⁸ |
|---|----|----|----|----|----|----|----|----|
| 136 | H | 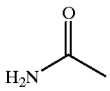 | H | H | H | Br | Br | OH |
| 137 | H | 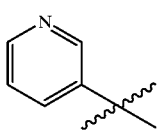 | H | H | H | Br | Br | OH |
| 138 | H | 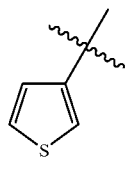 | H | H | H | Br | Br | OH |
| 139 | H | 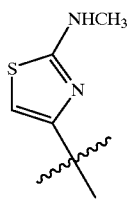 | H | H | H | Br | Br | OH |
| 140 | H | 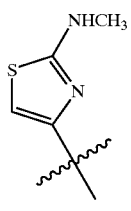 | H | H | H | Br | Br | OH |
| 141 | H | 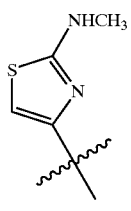 | H | H | H | Cl | Cl | OH |
| 142 | H | 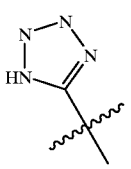 | H | H | H | Br | Br | OH |

TABLE 1A-continued
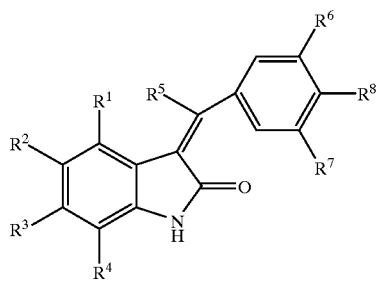
| # | R¹ | R² | R³ | R⁴ | R⁵ | R⁶ | R⁷ | R⁸ |
|---|----|----|----|----|----|----|----|----|
| 143 | H | H₃CN=N–N=N–C(CH₃)(–) (methyl-tetrazolyl-C(CH₃)–) | H | H | H | Br | Br | OH |
| 144 | H | 2-methyl-4-tert-butyl-thiazolyl | H | H | H | Br | Br | OH |
| 145 | H | 2-methyl-5-tert-butyl-1,3,4-oxadiazolyl | H | H | H | Br | Br | OH |
TABLE 1B
| # | R¹ | R² | R³ | R⁴ | R⁵ | R⁶ | R⁷ | R⁸ |
|---|----|----|----|----|----|----|----|----|
| 157 | H | (HOH₂CH₂C)₂N–SO₂–C(CH₃)(–) | H | H | H | Br | Br | OH |
| 162 | H | PhCH₂NH–C(O)–C(CH₃)(–) | H | H | H | Br | Br | OH |
| 163 | H | (CH₃)₂N | H | H | H | Br | Br | OH |
TABLE 1C
| # | R¹ | R² | R³ | R⁴ | R⁵ | R⁶ | R⁷ | R⁸ |
|---|----|----|----|----|----|----|----|----|
| 146 | H | Cl | H | H | H | Br | Br |  |

TABLE 1C-continued
| # | R¹ | R² | R³ | R⁴ | R⁵ | R⁶ | R⁷ | R⁸ |
|---|---|---|---|---|---|---|---|---|
| 147 | H | Cl | H | H | H | Br | Br | 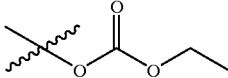 |
| 148 | H | Cl | H | H | H | Br | Br | 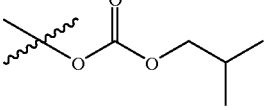 |
| 149 | H | Cl | H | H | H | Br | Br | 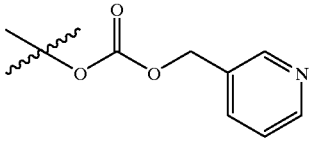 |
| 150 | H | Cl | H | H | H | Br | Br | 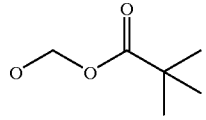 |
| 151 | H | I | H | H | H | Br | Br | 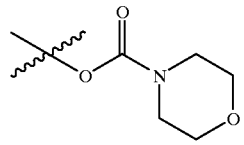 |
| 152 | H | I | H | H | H | Br | Br | 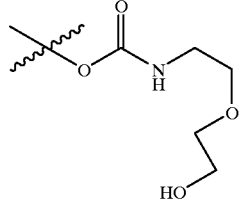 |
| 153 | H | I | H | H | H | Br | Br | 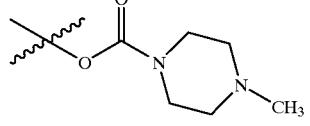 |
| 154 | H | I | H | H | H | Br | Br | 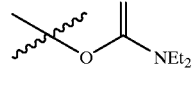 |
| 155 | H | 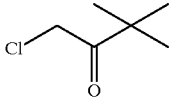 | H | H | H | Br | Br | 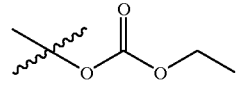 |
| 156 | H | CO₂H | H | H | H | Br | Br | OH |
| 158 | H | 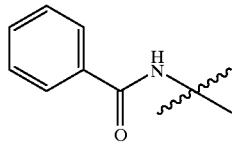 | H | H | H | Br | Br | OH |

TABLE 1C-continued
| # | R¹ | R² | R³ | R⁴ | R⁵ | R⁶ | R⁷ | R⁸ |
|---|---|---|---|---|---|---|---|---|
| 159 | H | 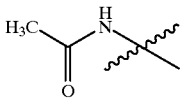 | H | H | H | Br | Br | OH |
| 160 | H | 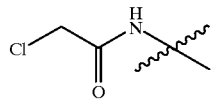 | H | H | H | Br | Br | OH |
| 161 | H | 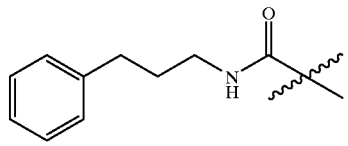 | H | H | H | Br | Br | OH |
| 164 | H | —SO₂NH₂ | H | H | H | Br | Br | 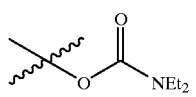 |
| 165 | H | —CH=CH—C(Me)=N— | H | H | H | Br | Br | OH |
| 166 | H | NH₂ | H | H | H | Br | Br | OH |
| 167 | H | 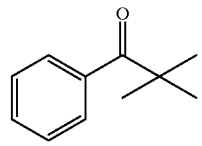 | H | H | H | Br | Br | 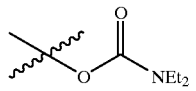 |
| 168 | H | 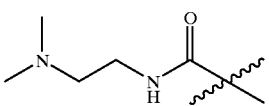 | H | H | H | Br | Br | OH |
| 169 | H | 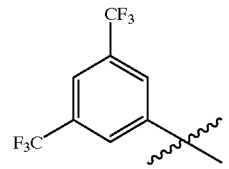 | H | H | H | Br | Br | OH |
| 170 | H | 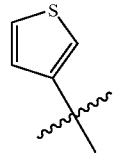 | H | H | H | Br | Br | OH |
| 171 | H | 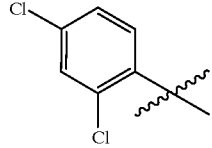 | H | H | H | Br | Br | OH |
| 172 | H | 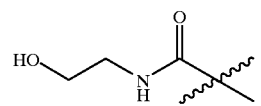 | H | H | H | Br | Br | OH |

TABLE 1C-continued

| # | R¹ | R² | R³ | R⁴ | R⁵ | R⁶ | R⁷ | R⁸ |
|---|---|---|---|---|---|---|---|---|
| 173 | H | 2-(dimethylamino)thiazol-4-yl-C(CH₃)- | H | H | H | Br | Br | OH |
| 174 | H | CH₃SO₂⁻ | H | H | H | Br | Br | OH |
| 175 | H | 4-(H₂NO₂S)phenyl-C(CH₃)- | H | H | H | Br | Br | OH |
| 176 | H | H | —CH=CH₂ | H | H | Br | Br | OH |
| 177 | H | 2-(CO₂Me)thien-3-yl-C(CH₃)- | H | H | H | Br | Br | OH |
| 178 | H | 2-(CN)phenyl-C(CH₃)- | H | H | H | Br | Br | OH |
| 179 | H | H | CN | H | H | Br | Br | OH |
| 180 | H | 2-[3-(dimethylamino)propylamino]thiazol-4-yl-C(CH₃)- | H | H | H | Br | Br | OH |
| 181 | H | N-(pyridin-4-ylmethyl)carbamoyl-C(CH₃)₂- | H | H | H | Br | Br | OH |

TABLE 2

| # | Chemical Name |
|---|---|
| 1 | 3-(3,5-Dibromo-4-hydroxy-benzylidine-2-oxo-2,3-dihydro-1H-indole-5-carbonitrile |
| 2 | 3-(3,5-Dibromo-4-hydroxy-benzylidene)-5-(2-methyl-thiazol-4-yl)-1,3-dihydro-indol-2-one |
| 3 | 3-(3-Bromo-5-ethoxy-4-hydroxy-benzylidene)-5-(2-methyl-thiazol-4-yl)-1,3-dihydro-indol-2-one |
| 4 | 3-(3,5-Dichloro-4-hydroxy-benzylidene-5-(2-methyl-thiazol-4-yl)-1,3-dihydro-indol-2-one (butanoyl)-1 ,3-dihydro-indol-2-one |

TABLE 2-continued

| # | Chemical Name |
|---|---|
| 5 | 3-(3,5-Dibromo-4-hydroxy-benzylidene-5-(3-methyl-butanoyl-1,3-dihydro-indol-2-one |
| 6 | 5-Benzoyl-3-(3,5-dibromo-4-hydroxy-benzylidene)-1,3 dihydro-indol-2-one |
| 7 | 5-Benzoyl-3-(3,5-dichloro-4-hydroxy-benzylidene)-1,3-dihydro-indol-2-one |
| 8 | 5-Benzoyl-3-(3-bromo-5-ethoxy-4-hydroxy-benzylidene)-1,3-dihydro-indol-2-one |
| 9 | 3-(3,5-Dichloro-4-hydroxy-benzylidene)-5-(3-methyl-butanoyl)-1,3-dihydro-indol-2-one |
| 10 | 3-(3-Bromo-5-ethoxy-4-hydroxy-benzylidene)-5-(3-methyl-butanoyl)-1,3-dihydro-indol-2-one |
| 11 | 3-(3,5-Dibromo-4-hydroxy-benzylidene-5-(pyridine-3-carbonyl)-1,3-dihydro-indol-2-one |
| 12 | 3-(3,5-Dichloro-4-hydroxy-benzylidiene)-5-(pyridine-3-carbonyl)-1,3-dihydro-indol-2-one |
| 13 | 3-(3,5-Dibromo-4-hydroxy-benzylidene)-5-(pyridine-4-carbonyl)-1,3-dihydro-indol-2-one |
| 14 | 3-(3-Bromo-5-ethoxy-4-hydroxy-benzylidene)-5-(pyridine-4-carbonyl)-1,3-dihydro-indol-2-one |
| 15 | 3-(3,5-Dichloro-4-hydroxy-benzylidene)-5-(pyridine-4-carbonyl)-1,3-dihydro-indol-2-one |
| 16 | 3-(3-Bromo-5-ethoxy-4-hydroxy-benzylidene)-5-(pyridine-3-carbonyl)-1,3-dihydro-indol-2-one |
| 17 | 3-(3,5-Dichloro-4-hydroxy-benzylidene-5-(oxazol-5-yl)-1,3-dihydro-indol-2-one |
| 18 | 3-(3,4-Dibromo-4-hydroxy-benzylidene)-5-(oxazol-5-yl)-1,3-dihydro-indol-2-one |
| 19 | 3-(3,5-Dibromo-4-hydroxy-benzylidene)-5-(2-ethyl-thiazol-4-yl)-1,3-dihydro-indol-2-one |
| 20 | 3-(3,5-Dibromo-4-hydroxy-benzylidene)-2-oxo-2,3-dihydro-1H-indol-5-carboxylic acid methyl ester |
| 21 | 3-(3,5-Dibromo-4-hydroxy-benzylidene)-5-(furan-2-carbonyl)-1,3-dihydro-indol-2-one |
| 22 | 3-(3,5-Dichloro-4-hydroxy-benzylidene)-5-(furan-2-carbonyl)-1,3-dihydro-indol-2-one |
| 23 | 3-(3-Bromo-5-ethoxy-4-hydroxy-benzylidene)-5-(furan-2-carbonyl)-1,3-dihydro-indol-2-one |
| 24 | 5-Cyclopropanecarbonyl-3-(3,5-dibromo-4-hydroxy-benzylidene)-1,3-dihydro-indol-2-one |
| 25 | 5-Aminomethyl-3-(3,5-dibromo-4-hydroxy-benzylidene)-1,3-dihydro-indol-2-one |
| 26 | 5-Cyclopentanecarbonyl-3-(3,5-dibromo-4-hydroxy-benzylidene)-1,3-dihydro-indol-2-one |
| 27 | 3-(3,5-Dichloro-4-hydroxy-benzylidene)-2-oxo-2,3-dihydro-1H-indole-5-carboxylic acid methyl ester |
| 28 | 3-(3,5-Dibromo-4-hydroxy-benzylidene)-1,3-dihydro-indol-2-one |
| 29 | 3-(3,5-Dibromo-4-hydroxy-benzylidene)-5-(thiophene-2-carbonyl)-1,3-dihydro-indol-2-one |
| 30 | 5-(2-Amino-thiazol-4-yl)-3-(3,5-dibromo-4-hydroxy-benzylidene)-1,3-dihydro-indol-2-one |
| 31 | 3-(3,5-Dibromo-4-hydroxy-benzylidene)-5-(imidazo[1,2a]pyridin-2-yl)-1,3-dihydro-indol-2-one |
| 32 | 3-(3,5-Dibromo-4-hydroxy-benzylidene)-5-propionyl-1,3-dihydro-indol-2-one |
| 33 | 3-(3,5-Dibromo-4-hydroxy-benzylidene)-2-oxo-2,3-dihydro-1H-indole-5-sulfonic acid amide |
| 34 | 3-(3,5-Dibromo-4-hydroxy-benzylidene)-2-oxo-2,3 dihydro-1H-indole-5-sulfonic acid N,N-diethylamide |
| 35 | 3-(3,5-Dibromo-4-hydroxy-benzylidene)-5-(pyrrolidine-1-sulfonyl)-1,3-dihydro-indol-2-one |
| 36 | 3-(3,5-Dibromo-4-hydroxy-benzylidene)-2-oxo-2,3-dihydro-1H-indol-5-sulfonic acid (N-2-dimethylamino-ethyl)-N-methyl-amide |
| 37 | 3-(3,5-Dibromo-4-hydroxy-benzylidene)-5-(isoxazole-5-carbonyl)-1,3-dihydro-indol-2-one |
| 38 | 5-Chloro-3-(3,5-dibromo-4-hydroxy-benzylidene)-1,3-dihydro-indol-2-one |
| 39 | 5-Chloro-3-(3,5-dichloro-4-hydroxy-benzylidene)-1,3-dihydro-indol-2-one |
| 40 | 3-(3,5-Dibromo-4-hydroxy-benzylidene)-5-trifluoromethoxy-1,3-dihydro-indol-2-one |
| 41 | 5-Bromo-3-(3,5-dichloro-4-hydroxy-benzylidene)-1,3-dihydro-indol-2-one |
| 42 | 3-(3-Bromo-5-ethoxy-4-hydroxy-benzylidene)-5-iodo-1,3-dihydro-indol-2-one |
| 43 | 3-(3-Bromo-4-hydroxy-5-methoxy-benzylidene)-5-iodo-1,3-dihydro-indol-2-one |
| 44 | 5-Bromo-3-(3,5-diiodo-4-hydroxy-benzylidene)-1,3-dihydro-indol-2-one |
| 45 | 3-(3,5-diiodo-4-Hydroxy-benzylidene)-5-trifluoromethoxy-1,3-dihydro-indol-2-one |
| 46 | 3-(3-Bromo-4-hydroxy-5-methoxy-benzylidene)-1,3-dihydro-indol-2-one |
| 47 | 3-(3,5-dinitro-4-Hydroxy-benzylidene)-1,3-dihydro-indol-2-one |
| 48 | 3-(3,5-dichloro-4-Hydroxy-benzylidene)-1,3-dihydro-indol-2-one |
| 49 | 3-(3-Chloro-4-hydroxy-5-methoxy-benzylidene)-1,3-dihydro-indol-2-one |
| 50 | 3-(3,5-diiodo-4-Hydroxy-benzylidene)-1,3-dihydro-indol-2-one |
| 51 | 3-(3-Bromo-4-hydroxy-5-methoxy-benzylidene)-5-chloro-1,3-dihydro-indol-2-one |
| 52 | 5-Chloro-3-(3,5-dinitro-4-hydroxy-benzylidene)-1,3-dihydro-indol-2-one |
| 53 | 5-Chloro-3-(4-hydroxy-3-methoxy-5-nitro-benzylidene)-1,3-dihydro-indol-2-one |
| 54 | 5-Chloro-3-(3-chloro-4-hydroxy-5-methoxy-benzylidene)-1,3-dihydro-indol-2-one |
| 55 | 5-Chloro-3-(3,5-diiodo-4-hydroxy-benzylidene)-1,3-dihydro-indol-2-one |
| 56 | 5-Bromo-3-(3-bromo-5-ethoxy-4-hydroxy-benzylidene)-1,3-dihydro-indol-2-one |
| 57 | 5-Bromo-3-(3-bromo-4-hydroxy-5-methoxy-benzylidene)-1,3-dihydro-indol-2-one |
| 58 | 3-(3-Bromo-4-hydroxy-5-methoxy-benzylidene)-5,6-difluoro-1,3-dihydro-indol-2-one |
| 59 | 3-(3-Bromo-5-ethoxy-4-hydroxy-benzylidene)-5-trifluoromethoxy-1,3-dihydro-indol-2-one |
| 60 | 3-(3,5-Dichloro-4-hydroxy-benzylidene)-5-trifluoromethoxy-1,3-dihydro-indol-2-one |
| 61 | 3-(3-Bromo-4-hydroxy-5-methoxy-benzylidene)-5-trifluoromethoxy-1,3-dihydro-indol-2-one |
| 62 | 3-(3,5-Dibromo-4-hydroxy-benzylidene)-5,7-dinitro-1,3-dihydro-indol-2-one |
| 63 | 3-(3,5-Dibromo-4-hydroxy-benzylidene)-5-nitro-1,3-dihydro-indol-2-one |
| 64 | 3-(3,5-Dibromo-4-hydroxy-benzylidene)-7-iodo-1,3-dihydro-indol-2-one |
| 65 | 3-(3,5-Dichloro-4-hydroxy-benzylidene)-5-nitro-1,3-dihydro-indol-2-one |
| 66 | 3-(3,5-dibromo-4-hydroxy-benzylidene)-7-iodo-1,3-dihydro-indol-2-one |
| 67 | 7-Bromo-3-(3,5-dichloro-4-hydroxy-benzylidene)-1,3-dihydro-indol-2-one |
| 68 | 3-(3-Bromo-5-ethoxy-4-hydroxy-benzylidene)-5-nitro-1,3-dihydro-indol-2-one |
| 69 | 2-(N-{3-[3-(3,5 Dibromo-4-hydroxy-benzylidene)-2-oxo-2,3-dihydro-1H-indol-5-yl]-2-oxo-ethyl}-N-methyl-amino)-acetamide |
| 70 | 3-(3,5-Dibromo-4-hydroxy-benzylidene)-5-{2-[(N-2-hydroxy-ethyl)-N-(3-hydroxy-propyl)-amino]-acetyl}-1,3-dihydro-indol-2-one |
| 71 | 3-(3,5-Dibromo-4-hydroxy-benzylidene)-5-(3-methylimidazol-1-yl-acetyl)-1,3-dihydro-indol-2-one |
| 72 | 3-(3,5-Dibromo-4-hydroxy-benzylidene-5-(2-(thiomorpholin-4-yl)-acetyl)-1,3-dihydro-indol-2-one |
| 73 | 3-(3,5-Dibromo-4-hydroxy-benzylidene-5-(2-morpholin-4-yl-acetyl)-1,3-dihydro-indol-2-one |
| 74 | 5-{2-[Bis-(2-hydroxy-ethyl)-amino]-acetyl}-3-(3,5-dibromo-4-hydroxy-benzylidene)-1,3-dihydro-indol-2-one |
| 75 | 3-(3,5-Dibromo-4-hydroxy-benzylidene)-5-{2-[N-(2-hydroxy-ethyl)-N-methyl-amino]-acetyl-1,3-dihydro-indol-2-one |
| 76 | 3-(3,5-Dibromo-4-hydroxy-benzylidene)-5-(2-(thiazolidin-3-yl)-acetyl)-1,3-dihydro-indol-2-one |
| 77 | 3-(3,5-Dibromo-4-hydroxy-benzylidene)-5-(2-(N-pyridinium)-acetyl)-1,3-dihydro-indol-2-one chloride |
| 78 | 5-{2-[N-Benzyl-N-(2-hydroxy-acetyl)-amino]-ethyl}-3-(3,5-dibromo-4-hydroxy-benzylidene)-1,3-dihydro-indol-2-one |
| 79 | 3-(3,5-Dibromo-4-hydroxy-benzylidene)-5-iodo-1,3-dihydro-indol-2-one |

TABLE 2-continued

| # | Chemical Name |
|---|---|
| 80 | 2,2-Dimethyl-propionic acid,2,6-dibromo-4-(5-iodo-2-oxo-1,3-dihydro-indol-3-ylidenemethyl)-phenoxymethyl ester |
| 81 | 5-Bromo-3-(3,5-dibromo-4-hydroxy-benzylidene)-1,3-dihydro-indol-2-one |
| 82 | 5-Bromo-3-(3-chloro-4-hydroxy-5-methoxy-benzylidene)-1,3-dihydro-indol-2-one |
| 83 | 3-(3,5-Dibromo-4-hydroxy-benzylidene)-5-(2-diethylamino-acetyl)-1,3-dihydro-indol-2-one |
| 84 | 5-(2-Chloro-acetyl)-3-(3,5-dibromo-4-hydroxy-benzylidene)-1,3-dihydro-indol-2-one |
| 85 | 3-(3,5-Dichloro-4-hydroxy-benzylidene)-5-(2-diethylamino-acetyl)-1,3-dihydro-indol-2-one |
| 86 | 5-(2-Chloro-acetyl)-3-(3,5-dibromo-4-hydroxy-benzylidene)-7-iodo-1,3-dihydro-indol-2-one |
| 87 | N-[bis-(2-hydroxy-ethyl)]carbamic acid, 2,6-dibromo-4-(5-iodo-2-oxo-1,3-dihydro-indol-3-ylidenemethyl) phenyl ester |
| 88 | 5-(2-Chloro-acetyl)-3-(3,5-dichloro-4-hydroxy-benzylidene)-1,3-dihydro-indol-2-one |
| 89 | 5-Acetyl-3-(3,5-dibromo-4-hydroxy-benzylidene)-1,3-dihydro-indol-2-one |
| 90 | 5-Acetyl-3-(3,5-dichloro-4-hydroxy-benzylidene)-1,3-dihydro-indol-2-one |
| 91 | 3-(3,5-Dibromo-4-hydroxy-benzylidene)-5-(3-methoxy-benzoyl)-1,3-dihydro-indol-2-one |
| 92 | 3-(3,5-Dibromo-4-hydroxy-benzylidene)-5-phenyl-1,3-dihydro-indol-2-one |
| 93 | 3-(3,5-Dichloro-4-hydroxy-benzylidene)-5-phenyl-1,3-dihydro-indol-2-one |
| 94 | 3-(3,5-Dibromo-4-hydroxy-benzylidene)-5-(2-(ethylamino)-4H-thiazol-4-yl)-1,3-dihydro-indol-2-one |
| 95 | 3-(3,5-Dibromo-4-hydroxy-benzylidene)-5-(4-nitro-benzoyl)-1,3-dihydro-indol-2-one |
| 96 | 3-(3,5-Dibromo-4-hydroxy-benzylidene)-5-(3-nitro-benzoyl)-1,3-dihydro-indol-2-one |
| 97 | 3-(3,5-Dibromo-4-hydroxy-benzylidene)-5-((hydroxyimino)-phenyl-methyl)-1,3-dihydro-indol-2-one |
| 98 | 3-(3,5-Dibromo-4-hydroxy-benzylidene)-5-propionyl-1,3-dihydro-indol-2-one |
| 99 | 3-(3,5-Dichloro-4-hydroxy-benzylidene)-2-oxo-2,3-dihydro-1H-indole-5-sulfonic acid amide |
| 100 | 3-(3,5-Dichloro-4-hydroxy-benzylidene)-5-(pyrrolidine-1-sulfonyl)-1,3-dihydro-indol-2-one |
| 101 | 3-(4-Hydroxy-3-methoxy-5-nitro-benzylidene)-1,3-dihydro-indol-2-one |
| 102 | 3-(4-Hydroxy-3-iodo-5-methoxy-benzylidene)-1,3-dihydro-indol-2-one |
| 103 | 2,6-Dibromo-4-[(5-chloro-2-oxo-1,2-dihydro-3H-indol-3-ylidene)methyl]phenyl acetate |
| 104 | 3-(4-Hydroxy-3-methoxy-5-nitro-benzylidene)-5-iodo-1,3-dihydro-indol-2-one |
| 105 | 3-(3-Chloro-4,5-dihydroxy-benzylidene)-5-nitro-1,3-dihydro-indol-2-one |
| 106 | 2,6-Dibromo-4-[(5-chloro-2-oxo-1,2-dihydro-3H-indol-3-ylidene)methyl]phenyl N,N-diisopropylcarbamate |
| 107 | 3-(3,5-Dibromo-4-hydroxy-benzylidene)-5-(2-dimethylamino-acetyl)-1,3-dihydro-indol-2-one |
| 108 | 3-(3,5-Dibromo-4-hydroxy-benzylidene)-5-{2-[N-ethyl-N-(2-hydroxy-ethyl)-amino]-acetyl}-1,3-dihydro-indol-2-one |
| 109 | 3-(3,5-Dibromo-4-hydroxy-benzylidene)-7-fluoro-1,3-dihydro-indol-2-one |
| 110 | 3-(3,5-Dibromo-4-hydroxy-benzylidene)-5-[2-(4-methyl-piperazin-1-yl)-acetyl]-1,3-dihydro-indol-2-one (hydrochloride salt) |
| 111 | 3-(3-Bromo-4-hydroxy-5-ethoxy-benzylidene)-5-(2-dimethylamino-acetyl)-1,3-dihydro-indol-2-one |
| 112 | 3-(3,5-Dibromo-4-hydroxy-benzylidene)-6-phenyl-1,3-dihydro-indol-2-one |
| 113 | 3-(3,5-Dibromo-4-hydroxy-benzylidene)-6-isopropoxy-1,3-dihydro-indol-2-one |
| 114 | 5-(2-Chloro-acetyl)-3-(3,5-diiodo-4-hydroxy-benzylidene)-1,3-dihydro-indol-2-one |
| 115 | 3-(3,5-Dichloro-4-hydroxy-benzylidene)-2-oxo-2,3-dihydro-1H-indol-5-sulfonic acid diethylamide |
| 116 | 3-(3,5-Dichloro-4-hydroxy-benzylidene)-5-(morpholine-4-sulfonyl)-1,3-dihydro-indol-2-one |

TABLE 2-continued

| # | Chemical Name |
|---|---|
| 117 | N-diethyl-2,6-dibromo-4-[(5-pyridine-3-carbonyl)-2-oxo-1,3-dihydro-indol-3-ylidenemethyl]phenyl ester |
| 118 | 5-Acetyl-3-(3,5-dibromo-4-hydroxy-benzylidene)-3,5,6,7-tetrahydro-1H-pyrrolo[2,3-f]indol-2-one |
| 119 | 1-(3,5-Dibromo-4-hydroxy-benzylidene)-1,3-dihydro-pyrrolo[3,2-f]quinolin-2-one |
| 120 | 3-(3,5-Dibromo-4-hydroxy-benzylidine)-5-ethyl-1,3-dihydro-indol-2-one |
| 121 | 8-(3,5-Dibromo-4-hydroxy-benzylidine)-6,8-dihydro-1-thia-3,6-diaza-as-indacen-7-one |
| 122 | (3,5-Dibromo-4-hydroxy-benzylidene)-5-trifluoromethoxy-1,3-dihydro-indol-2-one |
| 123 | 6-Bromo-3-(3,5-dibromo-4-hydroxy-benzylidene)-1,3-dihydro-indol-2-one |
| 124 | 3-(3,5-Dichloro-4-hydroxy-benzylidene)-5-(2-phenyl-thiazol-4-yl)-1,3-dihydro-indol-2-one |
| 125 | 3-(3,5-Dibromo-4-hydroxy-benzylidene)-5-(2-phenyl-thiazol-4-yl)-1,3-dihydro-indol-2-one |
| 126 | 3-(3,5-Dibromo-4-hydroxy-benzylidene)-5-(2-phenylamino-thiazol-4-yl)-1,3-dihydro-indol-2-one |
| 127 | 3-(3,5-Dichloro-4-hydroxy-benzylidene)-5-(2-phenylamino-thiazol-4-yl)-1,3-dihydro-indol-2-one |
| 128 | 3-(3,5-Dichloro-4-hydroxy-benzylidene)-5-(3-thioxo-2,3,4,5-tetrahydro-[1,2,4]-triazine-6-yl)-1,3-dihydro-indol-2-one |
| 129 | 3-(3,5-Dibromo-4-hydroxy-benzylidene)-5-(3-thioxo-2,3,4,5-tetrahydro-[1,2,4]-triazine-6-yl)-1,3-dihydro-indol-2-one |
| 130 | 3-(3,5-Dinitro-4-hydroxy-benzylidene)-5-(2-methyl-thiazol-4-yl)-1,3-dihydro-indol-2-one |
| 131 | 3-(3,5-Dinitro-4-hydroxy-benzylidene)-1,3-dihydro-indol-2-one |
| 132 | 8-(3,5-Dibromo-4-hydroxy-benzylidene)-6,8-dihydro-3H-1,2,3,6-tetraaza-as-indacen-7-one |
| 133 | 6-Bromo-3-(3,5-dichloro-4-hydroxy-benzylidene)-1,3-dihydro-indol-2-one |
| 134 | 5-(2-Amino-thiazol-4-yl)-3-(3,5-dichloro-4-hydroxy-benzylidene)-1,3-dihydro-indol-2-one |
| 135 | 2-Amino-8-(3,5-dibromo-4-hydroxy-benzylidene)-6,8-dihydro-1-thia-3,6-diaza-as-indacen-7-one |
| 136 | 5-(N-Acetyl-2-amino-thiazol-4-yl)-3-(3,5-dibromo-4-hydroxy-benzylidene)-1,3-dihydro-indol-2-one |
| 137 | 3-(3,5-Dibromo-4-hydroxy-benzylidene)-2-oxo-2,3-dihydro-1H-indol-5-carboxylic acid amide |
| 138 | 3-(3,5-Dibromo-4-hydroxy-benzylidene)-5-pyrid-3-yl-1,3-dihydro-indol-2-one |
| 139 | 3-(3,5-Dibromo-4-hydroxy-benzylidene)-5-thiophen-3-yl-1,3-dihydro-indol-2-one |
| 140 | 3-(3,5-Dibromo-4-hydroxy-benzylidene)-5-(2-methylamino-thiazol-4-yl)-1,3-dihydro-indol-2-one |
| 141 | 3-(3,5-Chloro-4-hydroxy-benzylidene)-5-(2-methylamino-thiazol-4-yl)-1,3-dihydro-indol-2-one |
| 142 | 3-(3,5-Dibromo-4-hydroxy-benzylidene)-5-(1H-tetrazol-5-yl)-1,3-dihydro-indol-2-one |
| 143 | 3-(3,5-Dibromo-4-hydroxy-benzylidene)-5-(2-methyl-2H-tetrazol-5-yl)-1,3-dihydro-indol-2-one |
| 144 | N[bis(2-Hydroxyethyl)]-carbamic acid 2,6 dibromo-4-[5-(2-methyl-thiazol-4-yl)-2-oxo-1,2-dihydro-indol-3-ylidenemethyl]-phenyl ester |
| 145 | 3-(3,5-Dibromo-4-hydroxy-benzylidene)-5-(5-methyl-[1,3,4]oxadiazol-2-yl)-1,3-dihydro-indol-2-one |
| 157 | 3-[(3,5-Dibromo-4-hydroxyphenyl)methylidene]-N,N-bis(2-hydroxyethyl)-2-oxo-5-indolinesulfonamide |
| 162 | N-Benzyl-3-[(3,5-dibromo-4-hydroxyphenyl)methylidene]-2-oxo-5-indolinecarboxamide |
| 163 | 3-[(3,5-Dibromo-4-hydroxyphenyl)methylidene]-5-(dimethylamino)-1,3-dihydro-2H-indol-2-one |
| 146 | Benzyl 2,6-dibromo-4-[(5-chloro-2-oxo-1,2-dihydro-3H-indol-3-ylidene)methyl]phenyl carbonate |
| 147 | 2,6-Dibromo-4-[(5-chloro-2-oxo-1,2-dihydro-3H-indol-3-ylidene)methyl]phenyl ethyl carbonate |
| 148 | 2,6-Dibromo-4-[(5-chloro-2-oxo-1,2-dihydro-3H-indol-3-ylidene)methyl]phenyl isobutyl carbonate |
| 149 | 2,6-Dibromo-4-[(5-chloro-2-oxo-1,2-dihydro-3H-indol-3-ylidene)methyl]phenyl 3-pyridinylmethyl carbonate |
| 150 | 2,6-Dibromo-4-[(5-chloro-2-oxo-1,2-dihydro-3H-indol-3-ylidene)methyl]phenoxymethyl pivalate |

TABLE 2-continued

| # | Chemical Name |
|---|---|
| 151 | 2,6-Dibromo-4-[(5-iodo-2-oxo-1,2-dihydro-3H-indol-3-ylidene)methyl]phenyl 4-morpholinecarboxylate |
| 152 | 2,6-Dibromo-4-[(5-iodo-2-oxo-1,2-dihydro-3H-indol-3-ylidene)methyl]phenyl N-[2-(2-hydroxyethoxy)ethyl]carbamate |
| 153 | 2,6-Dibromo-4-[(5-iodo-2-oxo-1,2-dihydro-3H-indol-3-ylidene)methyl]phenyl 4-methyltetrahydro-1(2H)-pyrazinecarboxylate |
| 154 | 2,6-Dibromo-4-[(5-iodo-2-oxo-1,2-dihydro-3H-indol-3-ylidene)methyl]phenyl N,N-diethylcarbamate |
| 155 | 2,6-Dibromo-4-[(5-glycoloyl-2-oxo-1,2-dihydro-3H-indol-3-ylidene)methyl]phenyl ethyl carbonate |
| 156 | 3-(3,5-Dibromo-4-hydroxy-benzylidene)-2-oxo-2,3-dihydro-1H-indol-5-carboxylic acid |
| 158 | N-3-[(3,5-Dibromo-4-hydroxyphenyl)methylidene]-2-oxo-2,3-dihydro-1H-indol-5-ylbenzamide |
| 159 | N-3-[(3,5-Dibromo-4-hydroxyphenyl)methylidene]-2-oxo-2,3-dihydro-1H-indol-5-ylbenzamide |
| 160 | N-3-[(3,5-Dibromo-4-hydroxyphenyl)methylidene]-2-oxo-2,3-dihydro-1H-indol-5-yl-2-hydroxyacetamide |
| 161 | 3-[(3,5-Dibromo-4-hydroxyphenyl)methylidene]-2-oxo-N-(3-phenylpropyl)-5-indolinecarboxamide |
| 164 | 4-[5-(Aminosulfonyl)-2-oxo-1,2-dihydro-3H-indol-3-ylidene]methyl-2,6-dibromophenyl N,N-diethylcarbamate |
| 165 | 1-[(3,5-Dibromo-4-hydroxyphenyl)methylidene]-7-methyl-1,3-dihydro-2H-pyrrolo[3,2-f]quinolin-2-one |
| 166 | 5-Amino-3-[(3,5-dibromo-4-hydroxyphenyl)methylidene]-1,3-dihydro-2H-indol-2-one |
| 167 | 4-[(5-Benzoyl-2-oxo-1,2-dihydro-3H-indol-3-ylidene)methyl]-2,6-dibromophenyl N,N-diethylcarbamate |
| 168 | 3-[(3,5-Dibromo-4-hydroxyphenyl)methylidene]-N-(2-(dimethylamino)ethyl]-2-oxo-5-indolinecarboxamide |
| 169 | 5-[3,5-bis(Trifluoromethyl)phenyl]-3-[(3,5-dibromo-4-hydroxyphenyl)methylidene]-1,3-dihydro-2H-indol-2-one |
| 170 | 3-[(3,5-Dibromo-4-hydroxyphenyl)methylidene]-5-(3-thienyl)-1,3-dihydro-2H-indol-2-one |
| 171 | 3-[(3,5-Dibromo-4-hydroxyphenyl)methylidene]-5-(2,4-dichlorophenyl)-1,3-dihydro-2H-indol-2-one |
| 172 | 3-[(3,5-Dibromo-4-hydroxyphenyl)methylidene]-N-(2-hydroxyethyl)-2-oxo-5-indolinecarboxamide |
| 173 | 3-[(3,5-Dibromo-4-hydroxyphenyl)methylidene]-5-[2-(dimethylamino)-1,3-thiazol-4-yl]-1,3-dihydro-2H-indol-2-one |
| 174 | 3-[(3,5-Dibromo-4-hydroxyphenyl)methylidene]-5-(methylsulfonyl)-1,3-dihydro-2H-indol-2-one |
| 175 | 4-3-[(3,5-Dibromo-4-hydroxyphenyl)methylidene]-2-oxo 2,3-dihydro-1H-indol-5-ylbenzenesulfonamide |
| 176 | 3-[(3,5-Dibromo-4-hydroxyphenyl)methylidene]-6-vinyl-1,3-dihydro-2H-indol-2-one |
| 177 | Methyl 3-3-[(3,5 dibromo-4-hydroxyphenyl)methylidene]-2-oxo-2,3-dihydro-1H-indol-5-yl-2-thiophenecarboxylate |
| 178 | 2-3-[(3,5 Dibromo-4-hydroxyphenyl)methylidene]-2-oxo-2,3-dihydro-1H-indol-5-ylbenzonitrile |
| 179 | 3-[(3,5-Dibromo-4-hydroxyphenyl)methylidene]-2-oxo-6-indolinecarbonitrile |
| 180 | 3-[(3,5-Dibromo-4-hydroxyphenyl)methylidene]-5-(2-[3-(dimethylamino)propyl]amino-1,3-thiazol-4-yl)-1,3-dihydro-2H-indol-2-one |
| 181 | 3-[(3,5-dibromo-4-hydroxyphenyl)methylidene]-2-oxo-N-(4-pyridinylmethyl)-1,2-dihydro-3H-indole-5-carboxamide |

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Aluminum, Benzenesulfonate, Benzoate, Bicarbonate, Bisulfate, Bitartrate, Borate, Bromide, Calcium, Calcium Edetate, Camsylate, Carbonate, Chloride, Chloroprocaine, Choline, Clavulanate, Citrate, Dibenzylethylenediamine, Diethanolamine, Dihydrochloride, Edetate, Edisylate, Estolate, Esylate, Ethylenediamine, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lithium, Lactobionate, Laurate, Malate, Maleate, Magnesium, Mandelate, Mesylate, Methylbromide, Methyinitrate, Methylsulfate, Monopotassium Maleate, Mucate, Napsylate, Nitrate, N-methylglucamine, Oxalate, Pamoate (Embonate), Palmitate, Pantothenate, Phosphateldiphosphate, Polygalacturonate, Potassium, Procaine, Salicyiate, Sodium, Stearate, Subacetate, Succinate, Sulfate, Tannate, Tartrate, Teoclate, Tosylate, Triethanolamine, Triethiodide, Trimethylammonium and Valerate.

Salts which are not pharmaceutically acceptable may be useful in the preparation of compounds of formula (I) and these form a further aspect of the invention.

Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted.

For the following defined terms, these definitions shall be applied, unless a different definition is given in the claims or elsewhere in this specification.

As used herein, the term "aliphatic" refers to the terms alkyl, alkyiene, alkenyl, alkenylene, alkynyl, and alkynylene.

As used herein, the term "lower" refers to a group having between one and six carbons.

As used herein, the term "alkyl" refers to a straight or branched chain hydrocarbon having a specified number of carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, and isopropyl, and the like. The term "alkyl" as used herein also generically refers to the below-defined terms, "alkylene", "alkenyl", "alkenylene", "alkynyl" and "alkynylene".

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

Examples of "alkylene" as used herein include, but are not limited to, methylene, ethylene, and the like.

As used herein, the term "alkenyl" refers to a hydrocarbon radical having from two to ten carbons and at least one carbon—carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to an straight or branched chain divalent hydrocarbon radical having from two to ten carbon atoms and one or more carbon—carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-diyl, and the like.

As used herein, the term "alkynyl" refers to a hydrocarbon radical having from two to ten carbons and at least one carbon—carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon—carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, "cycloalkyl" refers to a alicyclic hydrocarbon group with one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like. The term "cycloalkyl" as used herein also generically refers to the below defined terms "cycloalkylene", "cycloalkenyl", and "cycloalkenylene".

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-11-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, or others as identified throughout this specification and claims. multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like. A more comprehensive listing of such rings is found in the Summary of the Invention. The term "heterocyclic" also generically refers to the below-defined term "heterocyclylene".

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, or others as identified throughout this specification and claims, multiple degrees of substitution being allowed. Such a ring may be optionally fused to one or more benzene rings or to one or more of another "heterocyclic" rings or cycloalkyl rings. Examples of "heterocyclyiene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like. A more comprehensive listing of such rings is found in the Summary of the Invention.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkyisulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five—to seven—membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or others identified throughout this specification and claims, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like. A more comprehensive listing of such rings is found in the Summary of the Invention. The term "heteroaryl" also generically refers to the below-defined term "heteroaryiene".

As used herein, the term "heteroarylene" refers to a five—to seven—membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO—$, where $R_a$ is alkyl, alkenyl or alkynyl.

As used herein, the term "alkylsulfanyl" refers to the group $R_aS—$, where $R_a$ is alkyl, alkenyl, or alkynyl.

As used herein, the term "alkenylsulfanyl" refers to the group $R_aS—$, where $R_a$ is alkenyl or alkynyl.

As used herein, the term "alkylsulfenyl" refers to the group $R_aS(O)—$, where $R_a$ is alkyl, alkenyl or alkynyl.

As used herein, the term "alkylsulfonyl" refers to the group $R_aSO_2—$, where $R_a$ is alkyl, alkenyl or alkynyl.

As used herein, the term "acyl" refers to the group $R_aC(O)—$, where $R_a$ is alkyl, alkenyl, alkynyl, cycloalkyl, cycloalkenyl, or heterocyclyl.

As used herein, the term "aroyl" refers to the group $R_aC(O)—$, where $R_a$ is aryl.

As used herein, the term "heteroaroyl" refers to the group $R_aC(O)—$, where $R_a$ is heteroaryl.

As used herein, the term "alkoxycarbonyl" refers to the group $R_aOC(O)—$, where $R_a$ is alkyl.

As used herein, the term "carbamate" or "carbamoyl" refers to the group $R_aR_bNC(O)—$, where $R_a$ and $R_b$ are hydrogen, alkyl, aryl, heterocyclyl or heteroaryl.

As used herein, the term "alkylcarbonyloxy" refers to the group $R_aC(O)O—$, where $R_a$ is alkyl, alkenyl, alkynyl, cycloalkyl, cycloalkenyl, or heterocyclyl.

As used herein, the term "aroyloxy" refers to the group $R_aC(O)O—$, where $R_a$ is aryl.

As used herein, the term "heteroaroyloxy" refers to the group $R_aC(O)O—$, where $R_a$ is heteroaryl.

As used herein, the term "optionally" means that the subsequently described event(s) may or may not occur, and includes both situations where the event has or has not occurred.

As used herein, the term "substituted" refers to substitution with the named substituent or substituents, multiple degrees of substitution being allowed.

As used herein, the terms "contain" or "containing" can refer to in-line substitutions at any position along the above-defined alkyl, alkenyl, alkynyl or cycloalkyl substituents with one or more of any of O, S, SO, $SO_2$, N, or N-alkyl, including, for example, $—CH_2—O—CH_2—$, $—CH_2—SO_2—CH_2—$, $—CH_2—NH—CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

As used herein, the terms "biohydrolyzable carbamate", "biohydrolyzable carbonate" and "biohydrolyzable ureide" is a carbamate, carbonate or ureide, respectively, of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable carbamate is orally absorbed from the gut and is transformed to (I) in plasma. Many examples of such are known in the art, and include by way of example carbamates of lower alkylamines, substituted ethylenediamines, aminoacids, hydroxyalkylamines, heterocyclic and heteroaromatic amines, polyether amines, and the like. An example of such a biohydrolyzable carbamate applied to the general formula (I) is illustrated below in general formula (A):

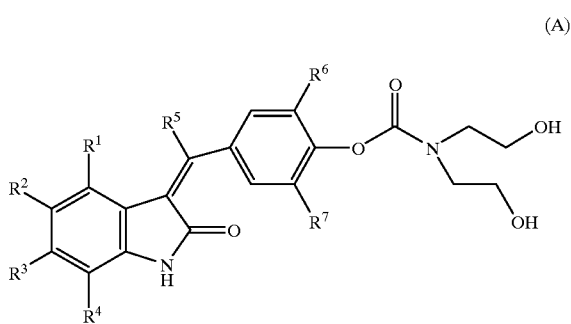

(A)

Other examples of biohydrolyzable carbamates include those situations in which $R^8$ is an OH moiety and said OH is conjugated with a carbamoyl conjugate to yield a biohydrolyzable carbamate wherein said carbamoyl conjugate is selected from the group consisting of diethylaminocarbonyl, N-(2-hydroxyethyl)aminocarbonyl, N,N,-bis(2-hydroxyethyl)aminocarbonyl, 4-morpholinocarbonyl and 4-methyl-1-piperazinylcarbonyl.

As used herein, the term "biohydrolyzable ester" is an ester of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters, lower acyloxy-alkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and biohydrolyzable carbamates, carbonates, and ureides, and also encompasses a) compounds in which the biohydrolyzable functionality in such a prodrug is encompassed in the compound of formula (I): for example, the lactam formed by a carboxylic group in $R^1$ and an amine in $R^2$, and b) compounds which may be oxidized or reduced biologically at a given functional group to yield drug substances of formula (1). Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or linked with a spacer of one to 50 atoms selected from the group consisting of C, H, O, N, S, or P in any combination. An example of an affinity reagent according to a) above would be fluorescein, either directly attached to (I) or linked with a spacer of one to 50 atoms selected from the group consisting of C, H, O, N, S, or P in any combination.

The term "pharmacologically effective amount" shall mean that amount of a drug or pharmaceutical agent that will elicit the biological or medical response of a tissue, system, animal or human that is being sought by a researcher or clinician.

Whenever the terms "alkyl" or "aryl" or either of their prefix roots appear in a name of a substituent (e.g. arylalkoxyaryloxy) they shall be interpreted as including those limitations given above for "aliphatic" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an aliphatic or cycloaliphatic moiety or to the aliphatic portion of a larger substituent.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

Preparation

The compounds of formula (I) can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:
g=grams
mg=milligrams
L=liters
mL=milliliters
mL=microliters
M=molar
N=normal
mM=millimolar
i.v.=intravenous
p.o.=per oral
s.c.=subcutaneous
Hz=hertz
mol=moles
mmol=millimoles
mbar=millibar
psi=pounds per square inch
rt=room temperature
min=minutes
hr=hours
mp=melting point
TLC=thin layer chromatography
$R_f$=relative TLC mobility
MS=mass spectrometry
NMR=nuclear magnetic resonance spectroscopy
APCI=atmospheric pressure chemical ionization
ESI=electrospray ionization
m/z=mass to charge ratio
HPLC=high pressure liquid chromatography
$t_r$=retention time
Pd/C=palladium on activated carbon
ether=diethyl ether
MeOH=methanol
EtOAc=ethyl acetate
TEA=triethylamine
DIEA=diisopropylethylamine
THF=tetrahydrofuran
DMF=N, N-dimethylformamide
DMSO=dimethylsulfoxide
DDQ=2,3-dichloro-5,6-dicyano-1,4-benzoquinone
LAH=lithium aluminum hydride
TFA=trifluoroacetic acid
HCl=hydrochloric acid
LDA=lithium diisopropylamide
THP=tetrahydropyranyl
NMM=N-methylmorpholine, 4-methylmorpholine
HMPA=hexamethylphosphoric triamide
DMPU=1,3-dimethylpropylene urea
d=days
ppm=parts per million
kD=kiloDalton
LPS=lipopolysaccharide
PMA=phorbol myristate acetate
SPA=scintillation proximity assay
EDTA=ethylenediamine tetraacetic acid
FBS=fetal bovine serum
PBS=phosphate buffered saline solution Several of the following examples represent single E isomers, single Z isomers and mixtures of E/Z isomers. Determination of the E and Z isomers can be done by analytical methods such as x-ray crystallography, $^1$H NMR and $^{13}$C NMR.

GENERAL REACTION SCHEMES

Compounds of the invention may be prepared by methods known in the art, where such a method is shown in Reaction Scheme 1.

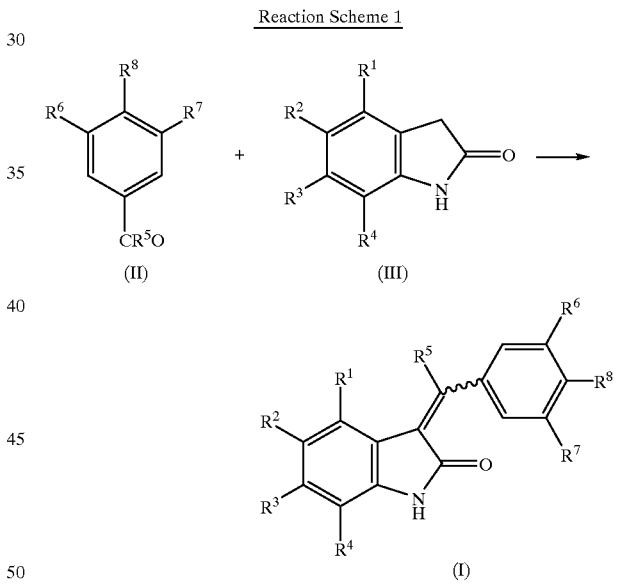

$R^1$, $R^2$, $R^3$, $R^4$, $R^5$, $R^6$, $R^7$, $R^8$ are defined as in formula (I).

The conversion of II and III to I involves methods known as the aldol condensation followed by elimination which is well described in "Advanced Organic Chemistry," Carey and Sundberg, 3rd edition, Plenum Press, 1990, principally contained in chapter 2 of part B. The reaction may be conducted using acid (for example concentrated HCl) in combination with a suitable solvent, such as acetic acid. Alternatively, catalytic acid conditions may be used such as using a catalytic amount of para-toluenesulfonic acid in a suitable solvent such as toluene.

Benzaldehydes of formula (II) are commercially available, or may be prepared by published procedures or variations of published procedures. Reaction Scheme 2 depicts two routes to readily synthesize substituted benzaldehydes that are not commercially available.

Reaction Scheme 2

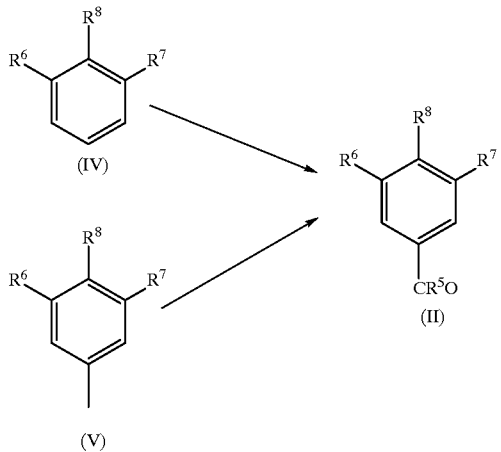

Generation of the substituted compounds of formula (II) may be obtained by a variety of methods by those skilled in the art. For example, the conversion of (IV) to (II) may be conducted by treating (IV) in a suitable solvent such as acetic acid with hexamethylenetetramine at a temperature of 90° C. to 130° C. Alternatively, (V) can be converted to (II) by treating (V) in a suitable solvent such as dioxane with a small amount of water with DDQ at a temperature of 0° C. to 140° C. In addition to the above, one compound of formula (II) can be converted to another compound of formula (II) by a chemical transformation of the appropriate substituent or substituents. For example, when $R^8$ is hydroxyl in (II), the conversion to a carbamate, carbonate, and ether is conducted by treating (II) in a suitable solvent such as THF with an alkylating agent such as chloromethyl-R, or an acylating agent such as alkylchloroformates and alkylcarbamoylchlorides in a suitable solvent such as dichloromethane.

Oxindoles of formula (III) are commercially available, or may be prepared by published procedures or variations of published procedures. Reaction Scheme 3 depicts several routes to synthesize compounds of formula (III).

Reaction Scheme 3:

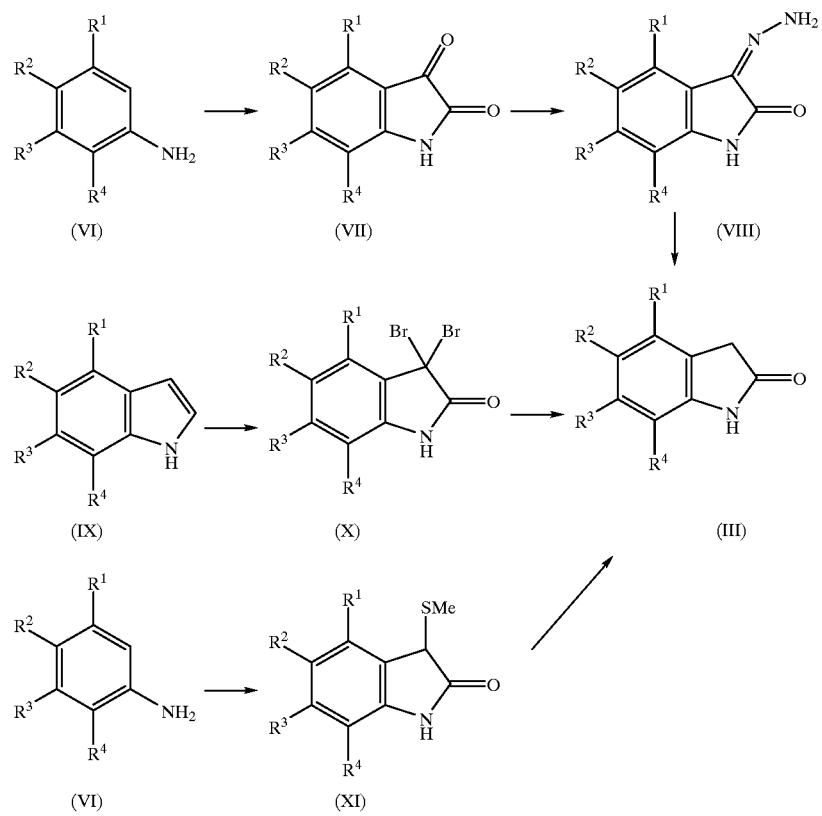

$R^1$, $R^2$, $R^3$, $R^4$, are defined as in formula (I).

The aniline of formula (VI) can be converted to the isatin of formula (VII) utilizing a known transformation called the Sandmeyer Isonitrosoacetanilide Isatin synthesis (T.

Sandmeyer, *Helv. Chim. Acta* 2, 234 (1919)) where (VI) may be condensed with chloral hydrate and hydroxylamine followed by cyclization with concentrated sulfuric acid and quantitative hydrolysis to a substituted isatin of formula (VII) on dilution with water. The conversion of (VII) to (III) may be conducted utilizing a known transformation called the Wolf-Kishner Reduction by treatment with hydrazine hydrate in a suitable solvent such as ethanol at a temperature of 20° C. to 80° C. to form (VIII). The conversion of (VIII) to (III) may be conducted by treatment with sodium ethoxide in a suitable solvent such as ethanol at a temperature of 0° C. to 80° C.

Alternatively, a substituted aniline of formula (VI) can be converted to a compound of formula (III) utilizing known chemistry. (P. G. Gassman and T. J. van Bergen, Journal of the American Chemical Society, 1974, 96(17), pages 5508–5512). The amine of formula (VI) may be converted to a compound of formula (XI) by treatment with t-butylhypochlorite, followed by treatment with ethyl methylthioacetate, followed by treatment with triethylamine in a suitable solvent such as anhydrous dichloromethane at a temperature of 78° C to 22 ° C. The conversion of (XI) to (III) may be conducted by treatment of (XI) with W-2 Raney Nickel in a suitable solvent such as ethanol or treatment with a saturated solution of ammonium chloride followed by treatment with activated zinc in a suitable solvent such as THF.

An indole of formula (IX) may be converted to (X) utilizing a method well described in the literature (A. Marfat and M. Carta, *Tetrahedron letters*, 28(35) pp 4027–4030, 1987) by treatment with pyridinium perbromide in a suitable solvent such as t-butyl alcohol at a temperature of 25° C. A compound of formula (X) may be converted to (III) by treatment with 10% Pd/C in a suitable solvent such as anhydrous ethanol at 30 to 50 psi of hydrogen or by treatment with a saturated solution of ammonium chloride followed by treatment with activated zinc in a suitable solvent such as THF.

Reaction Scheme 4

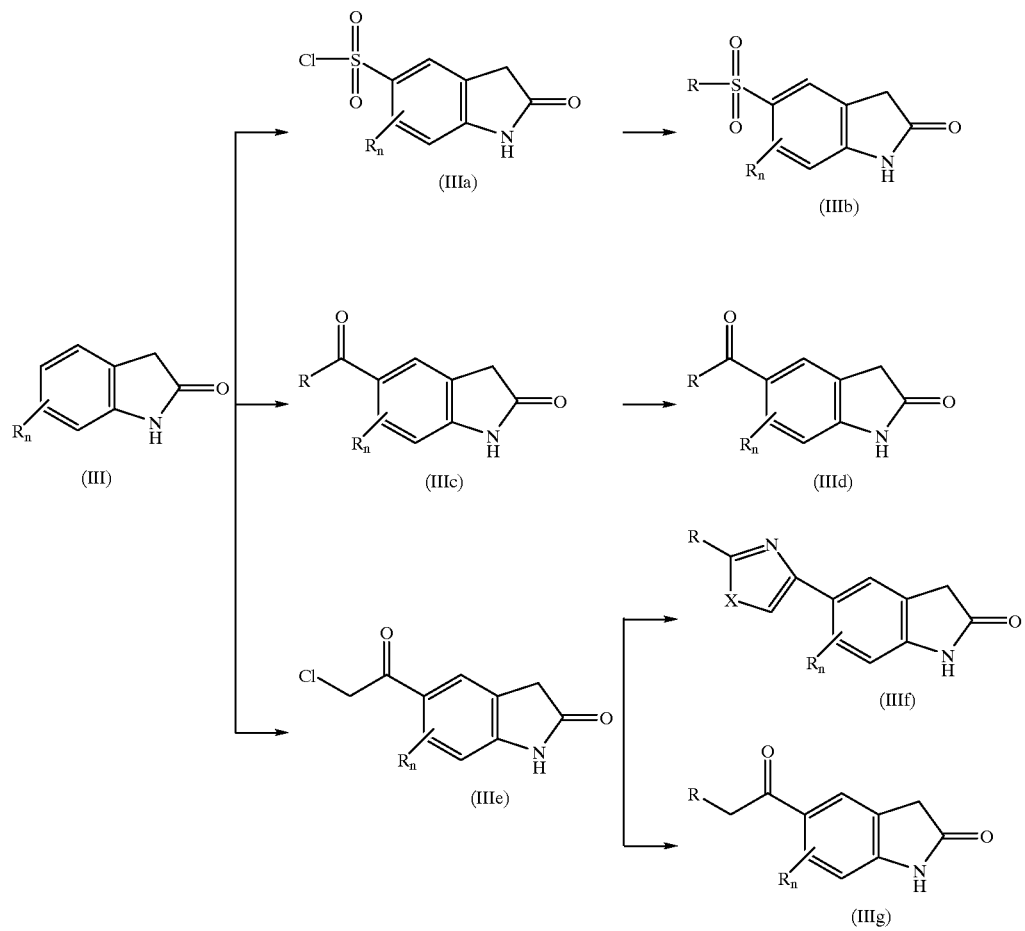

In addition to incorporating substitutions into the initial stages of the synthesis, one compound of formula (III) can be converted to another compound of formula (III) by a chemical transformation to the appropriate substituent or substituents. For example, Reaction Scheme 4 demonstrates several well established transformations for functionalizing an oxindole of formula (III). Oxindole may be converted to a sulfonic acid derivative (IIIa) by treatment of (II) with chlorosulfonic acid at a temperature of 0° C. to 60° C. A compound of formula (IIIa) may be converted to (IIIb) where R is substituted or unsubstituted amino, by treatment with a diverse set of amines. By way of example, (IIIa) may be treated with ammonium hydroxide to provide a sulfonamide derivative of formula (IIIb). Compound (III) may be converted to (IIIc) by treatment with an acid chloride in the presence of aluminum chloride in a suitable solvent such as dichloromethane or carbon disulfide at a temperature of 0° C. to 45° C. When R is OH in (IIIc) which is synthesized according to scheme 3, the conversion of carboxylic acid (IIIc) to esters and amides of formula (IIId) involves methods known in peptide chemistry, for example the reaction my be conducted using HOBt in combination with a dehydrating agent such as dicyclohexylcarbodiimide in a suitable solvent such as DMF. (III) may be converted to (IIIe) by treating (III) with chloroacetyl chloride in the presence of aluminum chloride in a suitable solvent such as dichloromethane or carbon disulfide at a temperature of 0° C. to 45° C. Further functionalization to various heterocyclic groups may be achieved through treatment of (IIIe) with diversely substituted amidines, thioamides, ureas and substituted aminopyridines. For example, (IIIe) may be converted to (IIIf) by treating (IIIe) with thioacetamide in a suitable solvent such as acetic acid at a temperature of 22° C. to 100° C. Compounds of formula (IIIg), where R is, for example an alkyl or cyclic amine, may be obtained by treating (IIIe) with diverse nucleophiles such as amines in a suitable solvent such as THF at a temperature of 22° C. to 80° C.

Reaction Scheme 5

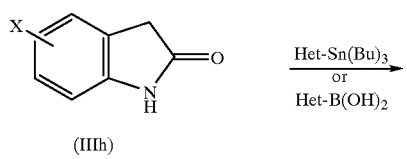

(IIIh)

-continued

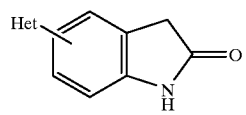

(IIIj)

A chemical transformation of a halogenated oxindole of formula III to another compound of formula III is described in Reaction Scheme 5. For example, a compound of formula (IIIh) where X is bromo or iodo may be treated with a tributyltin heterocycle, for example 3-pyridyltributyltin, in the presence of a palladium catalyst, for example bistriphenylphosphine dichloropalladium, in a suitable solvent, such as acetonitrile, to form (IIIj). Alternately, (IIIh) may be converted to (IIIj) by treatment with a heterocyclic or aromatic boronic acid, for example thiophene-3-boronic acid, in the presence of base, for example tetrakis-triphenyl phosphine palladium, in a suitable solvent, such as toluene, at a temperature of 22° C. to 125° C.

Reaction Scheme 6

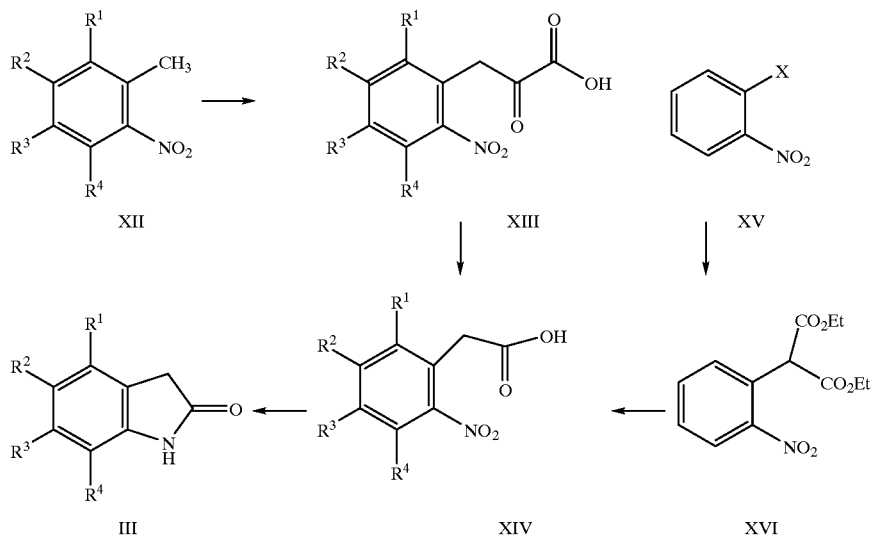

$R^1$, $R^2$, $R^3$, $R^4$, are defined as in formula (I).

A compound of formula (III) may also be synthesized using a method described by Reaction Scheme 6. A substituted 2-nitrotoluene (XII) may be converted to a compound of formula (XIII) by treatment with diethyl oxalate and sodium ethoxide in a suitable solvent such as ethanol. The product of this reaction can be directly treated with water to form (XIII) which could be converted to a compound of formula (XIV) by treatment with a hydrogen peroxide solution and sodium hydroxide in water at temperatures between 0° C. and 100° C. Treatment of (XIV) with zinc in sulfuric acid and a suitable solvent such as ethanol can provide a compound of formula (III). Alternately, a compound of formula XIV may be synthesized from a compound of formula XV where X is a halogen. Compound XV may be treated with a solution containing diethyl malonate and sodium ethoxide in a suitable solvent such as, ethanol, at a temperature from 0° C. to 78° C. to provide a compound of formula XVI. This compound of formula XVI may be hydrolyzed and decarboxylated to provide XIV using standard conditions such as treatment of XVI with aqueous sodium hydroxide, followed by the treatment of XVI with aqueous hydrochloric acid.

PHARMACEUTICAL FORMULATION AND DOSES

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

A therapeutically effective amount of a compound or salt of the present invention will depend upon a number of factors including, for example, the age and weight of the animal or patient, the precise condition requiring treatment and its severity, the nature of the formulation, and the route of administration, and will ultimately be at the discretion of the attendant physician or veterinarian.

Oral dosages of the present invention, when used for the indicated effects, will range between about 0.1 to 300 mg/kg of body weight per day, and particularly 1 to 100 mg/kg of body weight per day. Oral dosage units will generally be administered in the range of from 1 to about 250 mg and more preferably from about 25 to 250 mg. The daily dosage for a 70 kg mammal will generally be in the range of about 10 mg to 5 grams of a compound of formula 1. An effective amount of a salt of the present invention may be determined as a proportion of the effective amount of the compound per se.

Topical application similarly may be once or more than once per day depending upon the usual medical considerations. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paRaffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidytcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with paimitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl paimitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetRafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

SYNTHESIS EXAMPLES

We now set forth a selected number of synthesis examples which illustrate the techniques used to obtain the compounds of the invention. It is believed that one of ordinary skill in the art will, in view of the synthesis schemes set forth above, be able follow these procedures or modify them accordingly without undue experimentation in order to obtain any of the substitutions disclosed above. The following examples are illustrative embodiments of the invention, not limiting the scope of the invention in any way. Reagents are commercially available or are prepared according to procedures in the literature. Example numbers refer to those compounds listed in the tables above. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

Example

1; 3-(3,5-Dibromo-4-hydroxy-benzylidine)-2-oxo-2,3-dihydro-1H-indole-5-carbonitrile

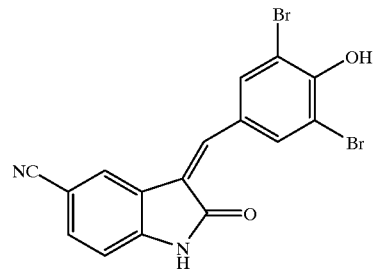

Example 1a 5-cyano-3-methylthiooxindole

A solution of 4-cyanoaniline (5.0 g, 42 mmol) in dry dichloromethane (100 mL) under $N_2$ was cooled to about −78° C. To this stirred solution was added a solution of tert-butylhypochlorite (4.6 g, 42 mmol) in dry dichloromethane (10 mL) over 5 min. and the resulting solution stirred for 10 minutes. A solution of ethyl methylthioacetate (5.45 mL, 5.69 g, 42 mmol) in dry dichloromethane (10 mL)

was than added dropwise and the mixture stirred for 1 hour. Triethylamine (5.9 mL, 4.28, 42 mmol) was added dropwise and the solution allowed to warm to room temperature over 1 hour. The reaction solution was washed with water (3×20 mL) and brine (1×20 mL), dried over anhydrous $MgSO_4$ and the solvent evaporated under vacuum to leave an orange oil. This oil was dissolved in diethyl ether (100 mL) and 2N aqueous hydrochloric acid (5 mL) was added and the mixture stirred vigorously at room temperature for 18 hours. The resulting tan solid was collected by filtration and washed with diethyl ether and dried under vacuum to give 5-cyano-3-methylthiooxindole as a white solid, (6.4 g, 76%). $^1H$ NMR ($CDCl_3$) δ9.04 (br s, 1H) 7.64 (s, 1H), 7.57 (d, 1H, J=8.4 Hz), 6.99 (d, 1H, J=8.4 Hz), 4.28 (s, 1H), 2.04 (s, 3H). MS (−ve ES) 203 (100), (M−H).

Example 1b

5-Cyanooxindole

A solution of 5-cyano-3-methylthiooxindole (6.0 g, 29 mmol) in THF (100 mL) was stirred at room temperature and a saturated aqueous solution of $NH_4Cl$ (100 mL) added followed by activated zinc (25 g, 0.38 mol). The resulting mixture was stirred for 18 hours. The mixture was filtered through a pad of diatomaceous earth and the pad washed with THF (20 mL). The organic phase was separated, dried over anhydrous $MgSO_4$ and the solvent evaporated to leave a tan solid. Trituration of this solid with diethyl ether gave 5-cyanooxindole a white solid, (4.1 g, 88%). $^1H$ NMR (DMSO-d6) δ7.63 (d, 1H, J=8.4 Hz), 7.62 (s, 1H), 6.93 (d, 1H, J=8.4 Hz), 3.55 (s, 2H). MS (−ve ES) 157 (100), (M−H)

Example 1

3-(3,5-Dibromo-4-hydroxy-benzylidine)-2-oxo-2,3-dihydro-1H-indole-5-carbonitrile The title compound was synthesized in an identical manner to example 2 except 5-cyano-oxindole was used in place of 5-(2-methyl-thiazol4-yl)-1,3-dihydro-indol-2-one hydrochloride. $^1H$ NMR (DMSO-d6) δ11.17 (s, 1H), 8.75 (s, 2H), 8.11 (s, 1H), 7.91 (s, 1H), 7.64 (d, 1H, J=8.4 Hz), 6.96 (d, 1H), J=8.4 Hz). MS (AP−ve) 419 (20) (M−H).

Example 2

3-(3,5-Dibromo-4-hydroxy-benzylidene)-5-(2-methyl-thiazol4-yl)-1,3-dihydro-indol-2-one

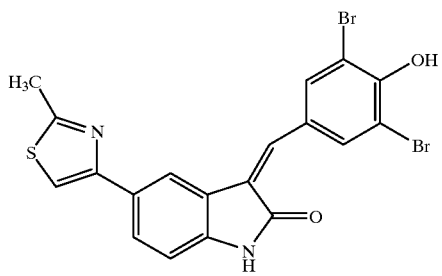

Example 2a 5-(2-Chloro-acetyl)-1,3-dihydro-indol-2-one

The following reagents were combined in the order listed under nitrogen at room temperature: aluminum chloride (17 g, 0.130 moles), carbon disulfide (40 mL), chloroacetyl chloride (3.01 g, 0.027 moles), and oxindole (2.73 g, 0.021 moles). The reaction mixture was warmed to reflux and stirring continued at this temperature for 3 h. The reaction was cooled to room temperature and the liquid was carefully decanted off. Ice water was added dropwise to the remaining residue under nitrogen (slowly and carefully). Addition of water was ceased when a total of 50 mL had been added and the reaction was stirred for 1 h at room temperature. The tan solid was collected by filtration, washed 3 times with water and dried in vacuo at 72° C. to give a light tan solid (3.4 g, 79% yield). $^1H$ NMR (DMSO-d6) δ3.62 (s, 2H); 5.15 (s, 2H); 6.96 (d, 1H); 7.84 (s, 1H); 7.91 (d, 2H); 10.84 (bs, 1H). APCI-MS m/z 208 (M−H).

Example 2b 5-(2-Methyl-thiazol4-yl)-1,3-dihydro-indol-2-one hydrochloride

Thioacetamide (90 mg, 1.2 mmol) was added to a slurry of 5-(2-chloro-acetyl)-1,3-dihydro-indol-2-one (250 mg,1.2 mmol) in acetic acid (3 mL). The reaction temperature was increased to 80° C. and stirred at this temperature for 16 h. The reaction mixture was cooled to room temperature and the resultant precipitate was collected by filtration. The solid was washed with EtOAc (2×20 mL) and ether (2×20 mL) and dried in vacuo to afford a cream colored solid (300 mg, 94% yield). $^1H$ NMR (DMSO-d6) δ2.74 (s, 3H); 3.58 (s, 2H); 6.87 (d, 1H); 7.79 (m, 3H); 10.57 (s, 1H). APCI-MS (−ve) m/z 229 (M−H), APCI-MS (+ve) m/z 231 (M+H) .Analytical calculated for $C_{12}H_{10}N_2OS.HCl$: C, 54.02; H, 4.16; N, 10.50; S, 12.02. Found: C, 53.73; H, 4.16; N, 10.17; S, 11.63.

Example 2

3-(3,5-Dibromo-4-hydroxy-benzylidene)-5-(2-methyl-thiazol4-yl)-1,3-dihydro-indol-2-one 5-(2-Methyl-thiazol4-yl)-1,3-dihydro-indol-2-one hydrochloride (0.030 g, 0.13 mmol) and 3,5-dibromo-4-hydroxy-benzaldehyde (0.037 g, 0.13 mmol) were combined and slurried in acetic acid (1.0 mL). Concentrated hydrochloric acid (0.25 mL) was added to the reaction mixture which caused the solids to dissolve. A yellow precipitate was collected by filtration after the reaction stirred for 4 h. The solid was washed with EtOAc (2×20 mL) and ether (2×20 mL) and dried in vacuo to afford a bright yellow solid (0.045 mg, 64% yield). $^1H$ NMR (DMSO-d6) δ2.80 (s, 3H); 6.89 (d, 1H); 7.77 (s, 1H); 7.82 (d, 1H); 7.86 (s, 1H); 8.27 (s, 1H); 8.87 (s, 2H); 10.82 (s, 1H). Electrospray MS m/z (−ve) 491. Analytical calculated for $C_{19}H_{12}N_2O_2Br_2S.HCl$: C, 43.17; H, 2.48; N, 5.30. Found: C, 42.82; H, 2.66; N, 5.14.

Example 8

5-Benzoyl-3-(3-bromo-5-ethoxy4-hydroxy-benzylidene)-1,3-dihydro-indol-2-one

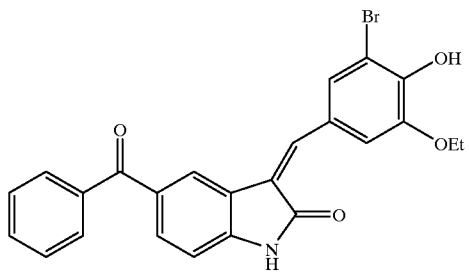

The title compound was synthesized in an identical manner to example 2 except 5-benzoyl oxindole was used in place of 5-(2-methyl-thiazol4-yl)-1,3-dihydro-indol-2-one hydrochloride and 3-bromo-5-ethoxy4-hydroxy-benzaldehyde was used in place of 3,5-dibromo-4-hydroxy-benzaldehyde. $^1$H NMR (DMSO-d6) δ1.38 (t, J=7 Hz, 3H), 4.14 (q, J=7 Hz, 2H), 6.94 (d, J=8.2 Hz, 1H), 7.50–7.68 (m, 4H), 7.69–7.72 (m, 2H), 7.90 (s, 1H), 8.14 (s, 1H), 8.34 (d, J=1.7 Hz, 1H), 8.48 (d, J=1.7 Hz, 1H), 10.15 (s, 1H), 11.02 (s, 1H); APCI-MS: m/z 464 (m−H)$^-$. Anal. Calcd for $C_{24}H_{18}NO_4Br$: C, 62.08; H, 3.91; N, 3.02; Br, 17.21. Found: C, 61.98; H, 3.88; N, 3.08; Br, 17.28.

Example 9

3-(3,5-Dichloro4-hydroxy-benzylidene)-5-(3-methyl-butanoyl)-1,3-dihydro-indol-2-one

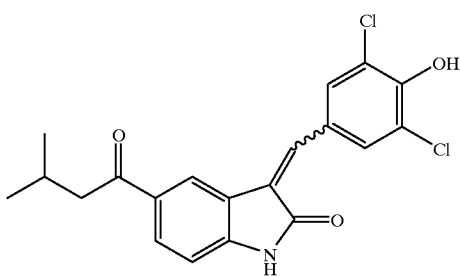

Example 9a 5-(3-methyl-butanoyl)-1,3-dihydro-indol-2-one

Aluminum trichloride (10.7 g, 7.5 mmole) was placed in a round bottom flask under nitrogen at room temperature. Dimethylformamide (1.7 mL) was added dropwise, which produced an exothermic reaction. The reaction stood for 15 minutes before the addition of oxindole (1 g, 7.5 mmole) followed by 3-methyl-butanoyl chloride (0.96 g, 8 mmole). The reaction was heated to 70° C. for 60 minutes. The reaction was poured onto crushed ice (100 g) with concentrated hydrochloric acid added (10 mL). The aqueous layer was extracted with EtOAc (100 mL). The organic layer was washed with a saturated NaCl (aqueous) solution, dried over $MgSO_4$. The volatiles were removed in vacuo to afford the desired compound (1.38 g, 85%). $^1$H NMR (DMSO-d$_6$): d 10.71 (s, 1H); 7.82 (d, J=8, 1H); 7.77 (s, 1H); 6.86 (d, J=8, 1H); 3.51 (s, 2H); 2.76 (d, J=7, 2H); 2.13–2.05 (m, 1H ); 0.88 (d, J=7, 6H) ESI-MS: m/z 216 (m−H)$^-$.

Example 9

3-(3,5-Dichloro4-hydroxy-benzylidene)-5-(3-methyl-butanoyl)-1,3-dihydro-indol-2-one The title compound was synthesized in an identical manner to example 2 except 5-(3-methyl-butanoyl)-1,3-dihydro-indol-2-one was used in place of 5-(2methyl-thiazol4-yl)-1,3-dihydro-indol-2-one and 3,5-dichloro-4-hydroxy-benzaldehyde was used in place of 3,5-bromo-4-hydroxy-benzaldehyde. $^1$H NMR (DMSO-d$_6$): δ11.05 (s, 1H); 10.99 (s, 1H1); 8.63 (s, 1H); 8.28 (s, 1H); 7.92 (s, 1H); 7.85 (d, J=8.2, 1H); 7.77 (s, 1H); 6.89 (d, J=8.2, 1H); 2.84 (d, J=6.8, 2H); 2.21–2.08 (m, 1H); 0.92 (d, J=6.8, 6H). ESI-MS: m/z 388 (m−H)$^-$.

Example 24

5-Cyclopropanecarbonyl-3-(3,5-Dibromo-4-hydroxy-benzylidene)-1,3-dihydro-indol-2-one

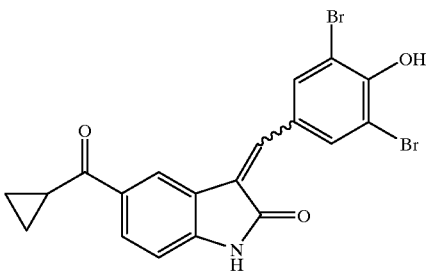

Example 24a

5-Cyclopropanecarbonyl-1,3-dihydro-indol-2-one

This compound was prepared in an identical manner to example 9a except that cyclopropane carbonyl chloride was used in place of 3-methyl-butanoyl chloride. $^1$H NMR (DMSO-d$_6$): δ10.73 (s, 1H); 7.93 (d, J=8.2, 1H); 7.85 (s, 1H); 6.88 (d, J=8.2, 1H); 3.53 (s, 2H); 2.79 (t, J=6.2, 1H); 0.94 (d, J=6.2, 4H) ESI-MS: m/z 200 (m−H)$^-$.

Example 24

5-Cyclopropanecarbonyl-3-(3,5-Dibromo-4-hydroxy-benzylidene)-1,3-dihydro-indol-2-one This compound was prepared in an identical manner to example 179 except that 5-cyclopropanecarbonyl-1,3-dihydro-indol-2-one was used in place of 6-cyano-1,3-dihydro-indol-2-one. $^1$H NMR (DMSO-d$_6$): δ11.11 (s, 1H); 10.80 (bs, 1H); 8.86 (s, 2H); 8.46 (s, 1H); 8.02–7.98 (m, 2H); 6.98 (d, J=8.1, 1H); 3.0–2.9 (m, 1H); 1.05 (d, J=6, 4H) ESI-MS: m/z 462 (m−H)$^-$.

Example 25

5-Aminomethyl-3-(3,5-dibromo-4-hydroxy-benzylidene)-1,3-dihydro-indol-2-one

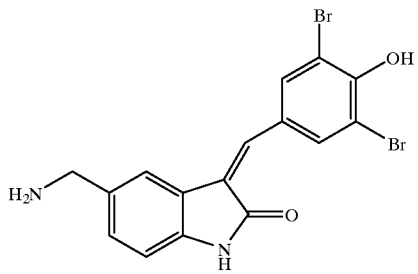

Example 25a

5-Aminomethyloxindole

A slurry of 5-cyanooxindole (1.0 g, 6.3 mmol) and 10 palladium on carbon (0.05 g) in glacial acetic acid (50 mL) at room temperature was hydrogenated under 40 psi pressure for 24 hours. The catalyst was removed by filtration through a pad of diatomaceous earth and the solvent evaporated from the filtrate to leave an orange oil of 5-aminomethyloxindole as an acetate salt (1.16 g). $^1$H NMR (DMSO-d6) δ7.21 (s, 1H), 7.14 (d, 1H, J=7.6 Hz), 6.75 (d, 1H, J=7.6 Hz), 3.74 (s, 2H), 3.44 (s, 2H). MS (+ve ES) 146 (100), (M–NH$_2$).

Example 25

5-Aminomethyl-3-(3,5-dibromo-4-hydroxy-benzylidene)-1,3-dihydro-indol-2-one

The title compound was synthesized in an identical manner to example 2 except 5-aminomethyl-oxindole acetate was used in place of 5-(2-methyl-thiazol-4-yl)-1,3-dihydro-indol-2-one hydrochloride. $^1$H NMR (DMSO-d6) δ10.80 (s, 1H), 8.76 (s, 2H), 8.14 (br s, 3H), 7.71 (s, 1H), 7.65 (s, 1H), 7.31 (d, 1H, J=7.6 Hz), 6.88 (d, 1H, J=7.6 Hz), 3.96 (br q, 2H, J=6 Hz). MS(AP+ve) 408 (100) (M–NH$_2$).

Example 119

1-(3,5-Dibromo-4-hydroxy-benzylidene)-1,3-dihydro-pyrrolo[3,2-f]quinolin-2-one

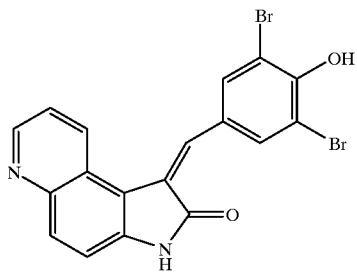

Example 119a

2-Hydroxyimino-N-(6-quinolinyl)acetamide hydrochloride

To a stirred solution of 10.0 g (60.0 mmol) of chloral hydrate in 250 mL of water was added 70.0 g (220 mmol) of sodium sulfate decahydrate, followed by a solution of 11.8 g (170 mmol) of hydroxylamine hydrochloride in 100 mL of water. A solution of 7.8 g (54 mmol) of 6-aminoquinoline in 200 mL of 1.0 N HCl was then added with stirring. The resulting suspension was warmed, and 400 mL of 95% EtOH was added to dissolve the suspension. The solution was refluxed for 0.75 h and then cooled to ambient temperature. The solution was neutralized with addition of solid sodium bicarbonate, and the resulting solid was collected by vacuum filtration and air dried to afford 8.1 g (60%) of 2-hydroxyimino-N-(6-quinolinyl)acetamide as a solid: $^1$H NMR (DMSO-d$_6$): 7.76 (s, 1H); 7.80 (dd, 1H, J=3.7, 8.4 Hz); 8.14 (s, 2H); 8.68 (s, 1H); 8.77 (d, 1H, J=8.4 Hz); 9.02 (d, 1H, J=3.7 Hz); 10.73 (s, 1H); 12.34 (s, 1H). Mass spectrum (negative ion chemical ionization): m/z=214 (60%).

Example 119b

3-H-Pyrrolo[3,2-f]quinoline-1,2-dione

2-Hydroxyimino-N-(6-quinolinyl)acetamide (7.00 g, 32.5 mmol) was combined with 70 mL of concentrated sulfuric acid with stirring and heated to a reaction temperature of 120° C. for 20 min, followed by an hour at 95° C. The reaction was allowed to cool to room temperature and was added dropwise to a mixture of 155 g (1.25 mole) of sodium carbonate monohydrate and 200 g of ice. After the addition was complete, water (600 mL) was added gradually to the mixture with stirring until all inorganic white solid was dissolved. The aqueous mixture was neutralized to pH 7 with 1 M hydrochloric acid and the product was collected by filtration. The collected solid was added to 200 mL of water and dissolved by dropwise addition of 1 M hydrochloric acid to free entrapped salts. The product was then precipitated by addition of saturated aqueous sodium bicarbonate to pH 7. The product was collected by filtration and dried under vacuum at 55° C. to give 3.89 g (60%) of 3-H-pyrrolo[3,2-f]quinoline-1,2-dione as a red-brown solid. Mass spectrum (negative ion chemical ionization): m/z=197 (30%). NMR (DMSO-d$_6$): δ7.43 (d, 1H, J=8.8 Hz), 7.66 (dd, 1H, J=4.1, 8.4 Hz); 8.29 (d, 1H, J=8.8 Hz); 8.72 (d, 1H, J=8.4 Hz); 8.82 (d, 1H, J=3.3 Hz); 11.2 (s, 1H).

Example 119c

1-Hydrazono-1,3-dihydropyrrolo[3,2-f]quinoline-2-one

3-H-Pyrrolo[3,2-f]quinoline-1,2-dione (3.89 g, 19.6 mmol) was combined with 12.0 mL of anhydrous hydrazine and 10.25 mL of water and heated at 100° C. under a condenser and nitrogen atmosphere, with stirring, for 1 hr. The reaction occasionally foamed into the condenser and heat was removed as needed to allow foaming to subside. The reaction was cooled and poured into 200 mL of water. The product was collected by filtration and dried under vacuum at 55° C. to give 2.86 g (69%) of 1-hydrazono-1,3-dihydropyrrolo[3,2-f]quinoline-2-one as a brown solid. Mass spectrum (positive ion electrospray): m/z=213. NMR (DMSO-d$_6$): δ7.37 (d, J=8.8 Hz, 1H), 7.47 (dd, J=8.4, 4.2 Hz, 1H), 7.81 (d, J=8.8 Hz, 1H), 8.71 (dd, J=4.2, 1.6 Hz, 1H), 8.80 (d, J=8.4 Hz, 1H), 9.90 (br d, J=14.7 Hz, 1H), 10.89 (br d, J=14.7 Hz, 1H), 10.95 (br s, 1H).

Example 119d

6-aminoquinoline-5-carboxylic acid hydrazide

1-Hydrazono-1,3-dihydro-pyrrolo[3,2-f]quinoline-2-one (1.07 g, 5.05 mmol) was combined with 6.0 mL of anhydrous hydrazine and 5.0 mL of water in a 100 mL flask (oversize to allow for foaming) and heated at reflux (145° C. oil bath) under a condenser and nitrogen atmosphere, with stirring. After 4.5 hr, analytical HPLC showed that all of the hydrazone had been consumed. The reaction was cooled, diluted with 75 mL of water, and filtered to give 0.45 g (air dried) of 6-aminoquinoline-5-carboxylic acid hydrazide as an olive brown solid. Mass spectrum (negative ion electrospray): m/z=215 (100%). NMR (DMSO-$d_6$): δ3.64 (s, 2H), 4.22 (s, 2H), 5.66 (s, 2H), 7.25 (d, 1H, J=9.1 Hz), 7.34 (m, 1H), 7.65 (d, 1H, J=9 Hz), 8.34 (d, 1H, J=8.5 Hz), 8.50 (s, 1H), 9.27 (s, 1H).

Example 119e 1,3-dihydro-pyrrolo[3,2-f]quinoline-2-one

6-Aminoquinoline-5-carboxylic acid hydrazide was dissolved in 10 mL of 2 M hydrochloric acid and heated briefly on a hot plate. The reaction was neutralized by gradual addition of solid sodium bicarbonate and filtered. The collected product was dried under vacuum at 55° C. to give 416 mg (45%) of 1,3-dihydro-pyrrolo[3,2-f]quinoline-2-one as a brown solid. Mass spectrum (negative ion chemical ionization): m/z=183 (60%). $^1$H NMR (DMSO-$d_6$): δ3.80 (s, 2H), 7.35 (d, J=8.8 Hz, 1H), 7.44 (dd, J=8.4, 4.2 Hz, 1H), 7.88 (d, J=8.8 Hz, 1H), 8.08 (d, J=8.4 Hz, 1H), 8.70 (dd, J=4.2, 1.6 Hz, 1H), 10.57 (br s, 1H).

Example 119

1-(3,5-Dibromo-4-hydroxy-benzylidene)-1,3-dihydro-pyrrolo[3,2-f]quinolin-2-one 1,3-Dihydro-pyrrolo[3,2-f]quinoline-2-one (552 mg, 3.00 mmol) was combined with 855 mg (3.05 mmol) of 3,5-dibromo-4-hydroxybenzaldehyde (TCl Chemicals) in 6 mL of glacial acetic acid with 1 mL of concentrated hydrochloric acid. The reaction was stirred at 115° C. for 8 hr, cooled and filtered, washing with ethyl acetate, to give 1.32 g of 1-(3,5-Dibromo-4-hydroxy-benzylidene)-1,3-dihydro-pyrrolo[3,2-f]quinolin-2-one hydrochloride as a brown solid which consisted of a 9/1 mixture of Z/E isomers. Mass spectrum (negative ion chemical ionization): m/z=443 (40%), 445 (100%), 447 (40%). $^1$H NMR (DMSO-$d_6$): δ7.69 (d, J=8.8 Hz, 1H); 7.93 (dd, J=8.7, 4.9 Hz, 1H); 8.24 (d, J=8.8 Hz, 1H); 8.27 (s, 1H); 8.80 (s, 1H); 9.04 (d, J=4.7 Hz, 1H); 9.51 (d, J=8.6 Hz, 1H); 11.3 (s, 1H).

Example 130

3-(3,5-Dinitro-4-hydroxy-benzylidene)-5-(2-methyl-thiazol-4-yl)-1,3-dihydro-indol-2-one

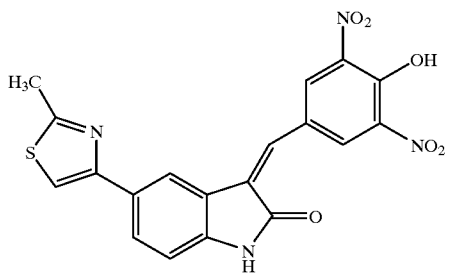

The title compound was synthesized in an identical manner to example 2 except 3,5-dinitro-4-hydroxy-benzaldehyde was used in place of 3,5-dibromo-4-hydroxy-benzaldehyde. $^1$H NMR (DMSO-d6) δ2.79 (s, 3H); 6.90 (d, 1H); 7.78 (s, 1H); 7.82 (d, 1H); 7.97 (s, 1H); 8.29 (s, 1H); 9.39 (s, 2H); 10.80 (bs, 1H). MS (+ve ES) 425 (MH+).

Example 133

6-Bromo-3-(3,5-dichloro-4-hydroxy-benzylidene)-1,3-dihydro-indol-2-one

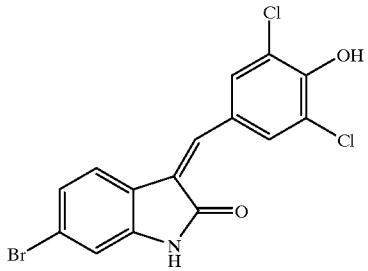

Example 133a

4-Bromo-2-nitrophenylpyruvic acid

Diethyl oxalate (29.2 g, 0.2 mol) and 4-bromo-2-nitrotoluene (21.6 g, 0.1 mol, Lancaster) were poured into a cooled sodium ethoxide solution, prepared from sodium (4.6 g, 0.2 mol) and absolute ethanol (90 mL). The mixture was stirred overnight at room temperature and then refluxed for 10 minutes at the end of the reaction. Water (30 mL) was added and the reaction refluxed for 2.5 h. The reaction mixture was cooled and concentrated to remove excess ethanol. The precipitate was collected by filtration, washed with ether and dried. The crude sodium salt was dissolved in water and acidified with conc. HCl. The solid precipitated and was collected by filtration. The crude product was recrystallized from hexane and ethyl acetate to give 12.5 g (43%) as a feathery putty-colored solid; $^1$H-NMR (CDCl$_3$): δ8.40 (d, 1H, J=1.9 Hz). 7,84 (dd, 1H, J=8.0, 2.0 Hz), 7.30 (d, 1H, J=2 Hz) 4.65 (s, 2H).

Example 133b 4-bromo-2-nitrophenylacetic acid

A 30% hydrogen peroxide solution (4.95 mL, 0.04 mol) was added dropwise to a solution of 4-bromo-2-nitrophenylpyruvic acid (0.04 mol) and sodium hydroxide (5.3 g 0.1 mol) in water (175 mL) stirring at 0° C. The reaction solution was stirred for 1 h at 5° C. and then acidified with dilute HCl. The yellow precipitate was filtered and the crude product recrystallized from hexane and ethyl acetate to yield 8.4 g (75%) as a light beige solid; $^1$H-NMR (DMSO-d6): δ12.67 (br s, 1H), 8.28 (d, J=2.0 Hz), 7.97 (dd, 1H, J=9.0 Hz, 2.0 Hz), 7.55 (d, 1H, J=8.0 Hz 4.00 (s, 3H). MS (−ve) m/z: 259 (M−H).

Example 133c

6-Bromooxindole

Zinc dust (8.5 g, 0.13 mol) was added slowly to a solution of 4-bromo-2-nitrophenylacetic acid (8.4 g, 0.03 mol) in 50% sulfuric acid (200 mL) and absolute ethanol (300 mL) at 90° C. over 0.75 h. The mixture was heated at this temperature for 2 h with stirring. The excess ethanol was removed by evaporation in vacuo and the mixture was filtered. The filtrate was extracted with diethyl ether. The combined organic portions were washed with saturated sodium bicarbonate, saturated sodium chloride, filtered with Whatman 1 PS Phase Separator paper and evaporated in vacuo to give 3.8 g (56%) a pale peach solid. $^1$H-NMR (DMSO-d6): δ10.57 (brs, 1H), 7.14 (m, 2H), 6.98 (s, 1H), 3.47 (s, 2H).

Example 133

6-Bromo-3-(3,5-dichloro-4-hydroxy-benzylidene)-1, 3-dihydro-indol-2-one

The title compound is synthesized in an identical manner to example 2 except 6-bromo-oxindole was used in place of 5-(2-methyl-thiazol4-yl)-1,3-dihydro-indol-2-one hydrochloride and 3,5-dichloro-4-hydroxy-benzaldehyde was used in place of 3,5-dibromo-4a-hydroxy-benzaldehyde. $^1$H NMR (DMSO-d6) δ7.05 (s, 1H); 7.12 (d, 1H); 7.43 (d, 1H); 7.56 (s, 1H); 7.76 (s, 2H); 10.78 (bs, 1H); 10.91 (bs, 1H). Electrospray MS (−ve) 384.

Example 138

3-(3,5-Dibromo-4-hydroxy-benzylidene)-5-pyrid-3-yl-1,3-dihydro-indol-2-one

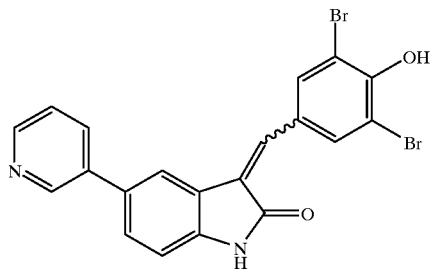

Example 138a 5-pyrid-3-yl- 1,3-dihydro-indol-2-one

A mixture of 0.736 g (2 mmol) of 3-tributyltin pyridine, 0.259 g (1 mmol) of 5-iodo-oxindole, 0.497 g (3 mmol) of tetraethyl ammonium chloride, and 0.035 g (0.05 mmol) of bis(triphenylphospine) palladium (II) chloride in 4 ml of acetonitrile was heated to reflux for 24 hrs. After cooling to ambient temperature the mixture was diluted with 20 ml of CHCl$_3$ and 50 ml of 10% potassium fluoride solution (aq) was added. Filtered the mixture through a 1 inch pad of celite and separated the layers. The organic layer was concentrated in vacuo, and the residue was chromatographed on silica gel (EtOAc/MeOH 5%) to afford 5-pyrid-3-yl-1,3-dihydro-indol-2-one as white solid (0.033 g, 16%): $^1$H NMR (DMSO-d$_6$): δ10.51 (s, 1H); 8.83 (d, J=2.2, 1H); 8.51 (dd, J$_1$=1.3, J$_2$=4.6, 1H); 8.02–7.97 (m, 1H); 7.59 (s, 1H); 7.54 (d, J=8.1, 1H); 7.44 (dd, J$_1$=4.7, J$_2$=7.9, 1H); 6.93 (d, J=8.1, 1H); 3.55 (s, 2H). APCI-MS: m/z 211 (m+H)$^+$.

Example 138

3-(3,5-Dibromo-4-hydroxy-benzylidene)-5-pyrid-3-yl-1,3-dihydro-indol-2-one

The title compound was prepared in an identical manner to example 2 except that 5-pyrid-3-yl-1,3-dihydro-indol-2-one was used in place of 5-(2-methyl-thiazol-4-yl)-1,3-dihydro-indol-2-one. $^1$H NMR (DMSO-d$_6$): δ10.93 (s, 1H); 9.13 (s, 1H); 8.81 (s, 2H); 8.8–8.7 (m, 1H); 8.6–8.5 (m, 1H); 8.23 (s, 1H); 7.94 (s, 1H); 7.9–7.8 (m, 1H); 7.72 (d, J=8, 1H); 7.02 (d, J=8, 1H). APCI-MS: m/z 471 (M−H)$^−$.

Example 144

N[bis(2-Hydroxyethyl)]-carbamic acid 2,6 dibromo-4-[5-(2-methyl-thiazol4-yl)-2-oxo-1,2-dihydro-indol-3-ylidenemethyl]-phenyl ester

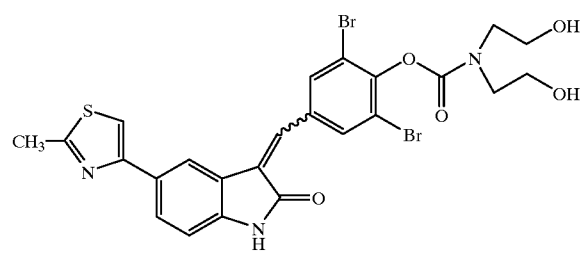

3-(3, 5-Dibromo-4-hydroxy-benzylidene)-5-(2-methyl-thiazol-4-yl)-1,3-dihydro-indol-2-one (0.50 g, 0.95 mmol) was slurried in 10 mL of anhydrous THF under nitrogen with 4A molecular sieves for 4 hrs. Diisopropylethylamine (0.33 mL, 1.9 mmol) was added to give a yellow-orange solution. In a separate flask, 0.50 ml of a phosgene solution (1.9 M in toluene, 0.95 mmol) and 5 mL of anhydrous THF was cooled in an ice bath under a pressure-equalizing dropping funnel and nitrogen atmosphere. The yellow-orange solution of the phenoxide anion was transferred to the dropping funnel via syringe, and the solution was added dropwise to the phosgene solution over 30 min. The reaction was allowed to warm to room temperature over 1 hr. The reaction was cooled again in an ice bath, and a solution of 135 mg (1.28 mmol) of diethanolamine and 0.165 mL of diisopropylethylamine (0.95 mmol) in 2 mL of anhydrous THF was added in one portion. The reaction was allowed to warm to room temperature and stir overnight. The orange reaction solution was diluted with 100 mL of ethyl acetate, washed with 50 mL of 0.2 M aqueous sodium bicarbonate, and dried over sodium sulfate. Evaporation of solvent gave 0.6 g of the crude product as an orange solid. The product was purified by chromatography on silica gel using 1:1 hexane/ethyl acetate followed by ethyl acetate to give 209 mg of 3-(3,5-dibromo-4-hydroxy-benzylidene)-5-(2-methyl-thiazol4-yl)-1,3-dihydro-indol-2-one as an orange solid. Mass spectrum (positive ion chemical ionization): m/z=644 (M+23) for $^{79}$Br with isotope peaks.

NMR (DMSO-d$_6$): (mix of E/Z isomers in ~2:1 ratio) δ2.70 and 2.76 (2s, 3H); 3.47 (m, 2H); 3.62 (m, 4H); 3.8 (m, 2H); 4.88 (m, 1H); 4.96 (m, 1H); 6.92 and 6.96 (2d, 1H, J=8 Hz); 7.62 (d, 1.3H, J=8 Hz); 7.76–7.96 (m, 2H); 8.15–8.33 (m, 2H); 8.87 (s, 0.7H); 10.81 and 10.88 (2s, 1H).

Example 147

3-(3,5-Dibromo-4-ethoxycarbonate-benzylidene)-2-oxo-2,3dihydro-5-chloro-1H-indole

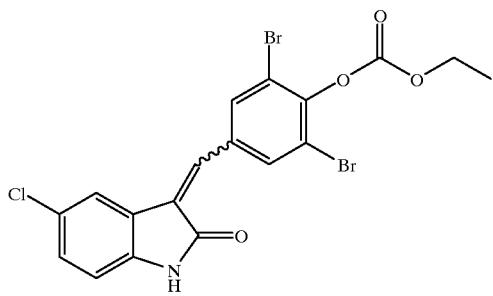

A heterogeneous mixture of 3-(3,5-dibromo-4-hydroxy-benzylidene)-2-oxo-2,3-dihydro-5-chloro-1H-indole (0.41 g, 1.0 mmol) in dry dichloromethane (15 mL) under nitrogen was treated with diisopropylethylamine (0.70 mL, 4.0 mmol) at room temperature. To the resulting homogeneous solution was added ethyl chloroformate (0.19 mL, 2.0 mmol) in a dropwise manner and the mixture stirred for three hours. The reaction was first washed with a saturated sodium bicarbonate solution, then with a saturated ammonium chloride solution. The organic layer was dried over magnesium sulfate, filtered and concentrated. The residue was dissolved in dichloromethane, cooled in an ice bath and the product was precipitated with hexanes. The solids were collected on a filter, washed with hexanes and air-dried to provide the title compound (0.34 g, 68%). $^1$H NMR (DMSO-d6): δ10.90 (s, 1H), 8.12 (s, 2H), 7.70 (s, 1H), 7.35–7.40 (m, 2H), 6.96 (d, 1H), 4.43 (q, 2H), 1.40 (t, 3H). Anal. Cald for $C_{18}H_{12}NO_4Br_2Cl$: C, 43.11; H 2.41; N, 2.79. Found: C, 43.01; H, 2.47; N, 2.73. MS (API+): 502(5) (M+1).

Example 150

3-(3,5-Dibromo-4-pivaloyloxymethoxy-benzylidene)-2-oxo-2,3-dihydro-5-chloro-1H-indole

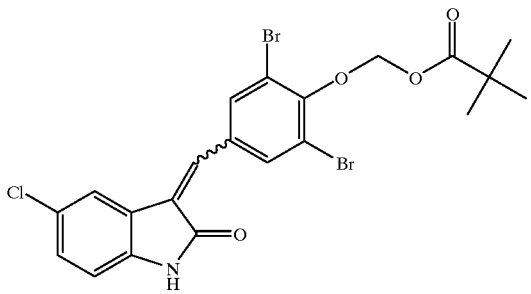

A solution of 3-(3,5-dibromo-4-hydroxy-benzylidene)-2-oxo-2,3-dihydro-5-chloro-1 H-indole (0.43 g, 1.0 mmol) in dry acetonitrile (20 mL) under nitrogen was treated with potassium tert-butoxide (0.12 g, 1.1 mmol) at room temperature. The resulting orange heterogenous mixture was treated with 18-crown-6 (0.053 g, 0.20 mmol) and stirred for 15 minutes before adding chloromethylpivalate (0.40 mL, 2.8 mmol). The reaction was heated to seventy degrees celsius, stirred for three hours then filtered while hot. The filtrate was allowed to cool to room temperature and stirred overnight. The resulting solids were collected on a filter, washed with acetonitrile and dried under vacuum to provide the title compound (0.24 g, 44%) as a mixture of E/Z isomers. $^1$H NMR (DMSO-d6): (mixture of E/Z isomers) δ10.93 (s, 1H), 10.87(s, 1H), 8.85 (s, 2H), 8.09 (s, 2H), 7.94 (s, 1H), 7.84 (d, 1H), 7.67 (s, 1H), 7.32–7.39 (m, 3H), 6.96 (d, 1H), 6.91 (d, 1H), 5.91 (s, 2H), 5.88 (s, 2H), 1.23 (s, 9H), 1.22 (s, 9H). MS (ES-): 542 (60) (M−1). Anal. Calcd for $C_{21}H_{18}NO_4ClBr_2$: C, 46.40; H, 3.34; N, 2.58. Found: C, 46.33; H, 3.30; N, 2.55.

Example 152

2,6-Dibromo-4-[(5-iodo-2-oxo-1,2-dihydro-3H-indol-3-ylidene) methyl]phenyl N-[2-(2-hydroxyethoxy)ethyl]carbamate

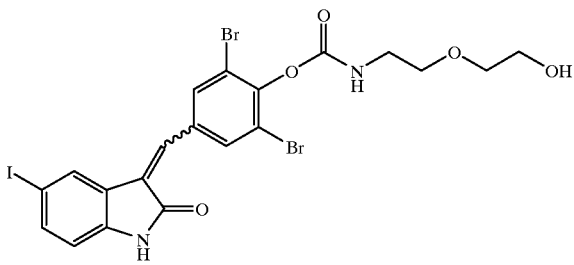

To a solution of 3-(3,5-Dibromo-4-hydroxy-benzylidene)-5-iodo-1,3-dihydro-indol-2-one (210 mg, 0.40 mmol) in 20 ml of THF under nitrogen was added 1M potassium t-butoxide in THF (0.40 ml, 0.40 mmol) dropwise via syringe. The solution was cooled to 0° C. and 1.97M phosgene in toluene (0.21 ml, 0.41 mmol) was added dropwise via syringe and the reaction mixture was stirred 10 minutes. 2-(2-Aminoethoxy)ethanol (40 μl, 0.40 mmol) was then added via syringe followed by N-methyl morpholine (~45 mg, ~45 mmol). The reaction mixture was stirred 10 minutes at 0° C. and then allowed to warm to room temperature. The solution was diluted with an equal volume of ether, filtered through a fine frit to clarify, and further diluted with 10 ml of ether. The product was then precipitated by the addition of ~80 ml of hexanes and was filtered and washed with more hexanes to give 0.21 g (79%) of the title compound as a yellow solid. $^1$H NMR (400 MHz, DMSO-$d_6$) 6: 10.77 (s, 1H), 8.24 (t, J=5.6 Hz, 1H), 8.02 (s, 2H), 7.6 (s, 1H), 7.57 (s, 1H), 7.55 (dd, J=8.2, 1.6 Hz, 1H), 6.71 (d, J=8.2 Hz, 1H), 4.58 (br t, 1H), 3.52–3.42 (m, 6H), 3.27–3.20 (m, 2H). ESI-MS m/z 673, 675, 677 (M+23). Anal. Calcd. for $C_{20}H_{17}Br_2IN_2O_5$: C, 36.84; H, 2.63; N, 4.30. Found: C, 36.75; H, 2.60; N, 4.22.

Example 156

3-(3,5-Dibromo-4-hydroxy-benzylidene)-2-oxo-2,3-dihydro-1H-indol-5-carboxylic acid 3-(3,5-Dibromo-4-hydroxy-benzylidene)-2-oxo-2,3-dihydro-1H-indol-5-carboxylic acid was prepared from 5-carboxylic acid oxindole and 3,5-dibromo-4-hydroxybenzaldehyde following the identical procedure as in example 2 except 3-(3,5-Dibromo-4-hydroxy-benzylidene)-2-oxo-2,3-dihydro-1H-indol-5-carboxylic acid was used in place of 5-(2-Methyl-thiazol-4-yl)-1,3-dihydro-indol-2-one hydrochloride. Yield 79%. $^1$H-NMR (DMSO-d6): δ12.6 (bs, 1H), 10.96 (s, 1H), 10.61 (bs, 1H), 8.17 (s, 1H), 7.93 (s, 2H), 7.84 (d, J=8.2 Hz, 1H), 7.54 (s, 1H), 6.93 (d, J=8.2 Hz, 1H). Mass spectrum (negative ion APCI): m/z=436 (M−1, 5%), 438 (M−1, 10%), 440 (M−1, 8%).

Example 159

N[3-(3,5-Dibromo-4-hydroxy-benzylidine)]-2-oxo-2,3-dihydro-1H-indol-5-yl)-acetamide

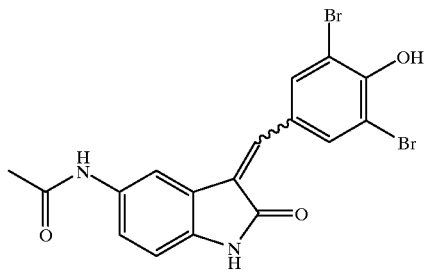

Example 159a 5-nitro-1,3-dihydro-indol-2-one

A solution of 5 g (37.6 mmol) of oxindole in 75 ml of conc. $H_2SO_4$ was chilled to −5° C. in an ice/EtOH bath. A solution of 3.83 g (45.1 mmol) of $NaNO_3$ in 25 ml of conc. $H_2SO_4$ was added dropwise over 30 min. The mixture was stirred at −5° C. for 1 hr. The ice bath was then removed and the mixture was allowed to slowly warm to ambient temperature. The mixture was poured onto 500 g of crushed ice. The solid was collected by vacuum filtration and air-dried. The solid was stirred in warm methanol and collected by vacuum filtration to yield 5-nitro-1,3-dihydro-indol-2-one (1.7 g, 25%): $^1$H NMR (DMSO-$d_6$): δ3.6 (s, 2H), 6.95 (d, J=8.5 Hz, 1H), 8.1 (s, 1H), 8.12 (d, J=8.7 Hz, 1H), 11.01 (s, 1H). APCI-MS: m/z 177 (m−H)$^−$.

Example 159b 5-amino 1,3-dihydro-indol-2-one

A mixture of 1.5 g (8.4 mmol) of 5-nitro-1,3-dihydro-indol-2-one, 150 mg of Pd/C 10%, and 50 ml MeOH in 100 ml of EtOAc was placed on Parr® hydrogenator and charged with 45 psi of Hydrogen gas. The mixture was shaken for 2 hrs. The mixture was filtered and the solvent was removed in vacuo to yield 5-amino 1,3-dihydro-indol-2-one (1.22 g, 98%): $^1$H NMR (DMSO-$d_6$): δ3.27 (s, 2H), 4.6 (s, 2H), 6.34 (dd, $J_1$=2 Hz, $J_2$=8.1 Hz, 1H), 6.45 (m, 2H), 9.88 (s, 1 H). APCI-MS: m/z 147 (m−H)$^−$.

Example 159c

N-(2-oxo-2,3-dihydro-1H-indol-5-yl)-acetamide

A mixture of 200 mg (1.35 mmol) of 5-amino 1,3-dihydro-indol-2-one in 6 ml of acetic anhydride was refluxed for 30 minutes. The reaction mixture was poured onto 50 g of crushed ice. The mixture was stirred well and the solid was collected by vacuum filtration. The solid was washed with 200 ml of $H_2O$ and air dried to yield N-(2-oxo-2,3-dihydro-1H-indol-5-yl)-acetamide (119 mg, 46%): $^1$H NMR (DMSO-$d_6$): δ1.97 (s, 3H), 3.41 (s, 2H), 6.68 (d, J=8.4 Hz, 1H), ), 7.26 (dd, $J_1$=2 Hz, $J_2$=8.4 Hz, 1H), 7.46 (d, J=2 Hz, 1H), 9.73 (s, 1H). 10.23 (s, 1H), ESI-MS: m/z 189 (m−H)$^−$.

N[3-(3,5-Dibromo-4-hydroxy-benzylidine)]-2-oxo-2,3-dihydro-1H-indol-5-yl)-acetamide.

A mixture of 0.050 g (0.26 mmol) of N-(2-oxo-2,3-dihydro-1H-indol-5-yl)-acetamide and 0.081 g (0.29 mmol) of 3,5-dibromo-4-hydroxybenzaldehyde was stirred in 2 ml of HOAc. 100 ?l of concentrated HCl was added and the mixture was heated to 80$^?$ C. for 3 hrs. After cooling to ambient temperature, the solid was collected by vacuum filtration and washed with EtOAc and $Et_2O$ and dried in a vacuum oven to yield N-[3-(3,5-dibromo-4-hydroxy-benzylidine)]-2-oxo-2,3-dihydro-1H-indol-5-yl)-acetamide as a yellow solid (0.76 g, 65%): $^1$H NMR (DMSO-$d_6$): δ1.99 (s, 3H), 6.72 (d, J=8.3 Hz, 1H), 7.17 (dd, $J_1$=1.8 Hz, $J_2$=8.3 Hz, 1H), 7.54 (s, 1H), 7.86 (d, J=1.5 Hz, 1H), 8.79 (s, 2H), 9.74 (s, 1H), 10.54(s, 1H). APCI-MS: m/z 475 (m+Na)$^+$

Example 172

3-(3,5-Dibromo-4-hydroxy-benzylidene)-2-oxo-2,3-dihydro-1H-indol-5-carboxylic acid (2-hydroxyethyl)amide

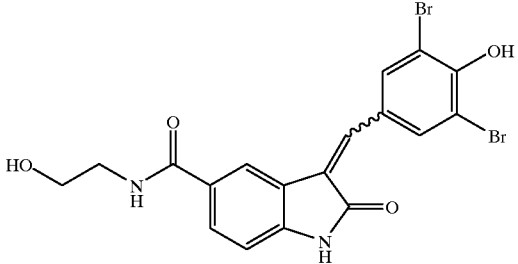

Example 172a

5-Carboxylic acid-1,3-dihydro-indol-2-one

5-Carboxylic acid-1,3-dihydro-indol-2-one methyl ester (5.6 g, 29.3 mmol) was dissolved in hot acetonitrile (500 mL) and aluminium iodide (25 g, 61.3 mmol) added slowly. Reaction refluxed for 0.5 h and then poured onto ice-water and extracted twice with ethyl actetate (200 mL). Material insoluble in both phases was filtered off and washed with aqueous sodium thiosulfate solution, followed by water and dried. Yield of 5-Carboxylic acid-1,3-dihydro-indol-2-one: 1.9 g. The ethyl acetate solution was washed with aqueous sodium thiosulfate solution and concentrated to dryness. Yield of 5-Carboxylic acid-1,3-dihydro-indol-2-one: 0.2 g. The aqueous phase was treated with sodium thiosulfate solution and on standing deposited more product as a precipitate. This was filtered off, washed with water and dried. Yield of 5-Carboxylic acid-1,3-dihydro-indol-2-one: 2.8 g; $^1$H-NMR (DMSO-d6): δ12.60 (bs, 1H), 10.73 (bs, 1H), 7.84 (d, J=8.1 Hz, 1H), 7.77 (s, 1H), 6.90 (d, J=8.1 Hz, 1H), 3.56 (s, 2H). Mass spectrum (negative ion electrospray): m/z=176 (M−1, 6%).

Example 172

3-(3,5-Dibromo-4-hydroxy-benzylidene)-2-oxo-2,3-dihydro-1H-indol-5-carboxylic acid (2-hydroxyethyl)amide 3-(3,5-Dibromo-4-hydroxy-benzylidene)-2-oxo-2,3-dihydro-1H-indol-5-carboxylic acid (0.34 9, 0.77 mmol) (Example 156) and ethanofamine (0.08 g, 1.3 mmol) were dissolved in DMF (2 mL) and cooled with stirring to 5° C.

Diethyl cyanophosphonate (0.172 g, 1 mmol), followed by triethylamine (0.25 g, 2.5 mmol) were added and stirring continued for 0.5 h at 50° C. and then the reaction allowed to warm to room temperature. After 1.5 h the reaction was quenched with water (10 mL) and extracted four times with a 4/1 mixture of chloroform/isopropanol (25 mL). The organic phases were combined, dried over magnesium sulfate and concentrated to dryness. Recrystalization from ethanol gave 22 mg of 3-(3,5-dibromo-4-hydroxy-benzylidene)-2-oxo-2,3-dihydro-1H-indol-5-carboxylic acid (2-hydroxyethyl)amide; $^1$H-NMR (DMSO-d6): δ10.9 (s, 1H), 10. 7 (bs, 1H), 8.81 (s, 2H), 8.25 (t, J=5.6 Hz, 1H), 8.19 (s, 1H), 7.77 (s, 1H), 7.72 (d, J=8.0 Hz, 1 H), 6.86 (d, J=8.0 Hz, 1 H), 4.73 (bs, 1H), 3.52 (m, 2H), 3.37 (m, 2H). Mass spectrum (negative ion electrospray): m/z=479 (M−1, 22%), 481 (M−1, 35%), 483 (M−1, 30%).

Example 179

6-Cyano-3-(3,5-dibromo-4-hydroxy-benzylidlene)-1, 3-dihydro-indol-2-one

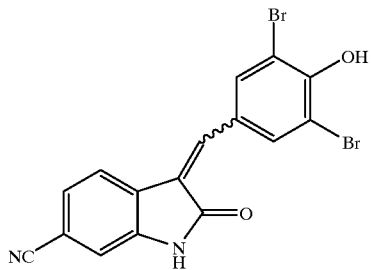

Example 179a 6-cyano-1,3-dihydro-indol-2-one

6-Bromo-1,3-dihydro-indol-2-one (0.621 g, 2.93 mmol), tributyltin cyanide 1.11 g, 3.5 mmol), tetraammonium chloride hydrate (0.97 g, 5.9 mmol), dichlorobis (triphenylphosphine)palladium(II) (0.21 g, 0.3 mmol) and tetrakis (triphenylphosphine)palladium(0) (0.342 g, 0.3 mmol) were treated with dichloroethane (100 mL) and the reaction refluxed for 16 h under nitrogen with stirring. A further addition of tetrakis (triphenylphosphine)palladium (0) (0.23 g, 0.2 mmol) was made and reflux continued a further 6 h. A third addition of tetrakis (triphenylphosphine) palladium(0) (0.345 9, 0.3 mmol) was made and the reaction returned to reflux for 16 h. On cooling the reaction solution was washed twice with an aqueous solution of potassium fluoride (50 mL) and the organic phase dried over magnesium sulfate, filtered and evaporated to dryness. The product was subjected to chromatography on silica gel using dichloromethane to give 140 mg of 6-cyano-1,3-dihydro-indol-2-one contaminated with triphenylphosphine oxide. A second chromatographic purification chromatography on silica gel using dichloromethane gave 61 mg of pure 6-cyano-1,3-dihydro-indol-2-one; $^1$H-NMR (DMSO-d6): δ10.64 (bs, 1H), 7.37 (s, 2H), 7.10 (s, 1H), 3.56 (s, 2H). Mass spectrum (negative ion electrospray): m/z=157 (M−1, 100%).

Example 179

6-Cyano-3-(3,5-dibromo-4-hydroxy-benzylidene)-1, 3-dihydro-indol-2-one 6-cyano-1,3-dihydro-indol-2-one (46.3 mg, 0.29 mmol) and 3,5-dibromo-4-hydroxybenzaldehyde (80 mg, 0.39 mmol) and p-toluenesulfonic acid monohydrate (1 mg, 0.005 mmol) were treated with toluene (30 mL) and the reaction refluxed with stirring with a Dean-Stark water trap attached for 1.5 h. During this time an orange solid deposited, which, on cooling, was filtered off, washed with toluene and dried in vacuo at 125° C. for 3 days to give 80 mg of 6-cyano-3-(3,5-dibromo-4-hydroxy-benzylidene)-1, 3-dihydro-indol-2-one; $^1$H-NMR (DMSO-d6): δ11.05 (bs, 1H), 8.86 (s, 2H), 7.97 (s, 1H), 7.85 (d, J=7.9 Hz, 1 H), 7.50 (d, J=7.9 Hz, 1 H), 7.20 (s, 1H). Mass spectrum (negative ion electrospray): m/z=417 (M−1, 48%), 419 (M−1, 100%), 421 (M−1, 48%).

UTILITY

Kinase signal transduction results, in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma; psoriasis, arteriosclerosis, arthritis and diabetic retinopathy or other disorders related to uncontrolled angiogenesis and or vasculogenesis.

The efficacy of compounds of the present invention as inhibitors of Raf kinase activity can be evaluated and measured using pharmacological methods known in the art or as described in detail below based on similarly established methodologies.

The potency of cRaf1 dependent kinase activity was measured using one of two assay formats. The first measured cRaf1 catalyzed phosphorylation of MEK1, the natural substrate for cRaf1. This assay is referred to as the cRaf1 assay. The second measured the ability of cRaf1 to phosphorylate and activate MEK1. This assay is referred to as the Raf/MEK cascade assay. The Raf/MEK cascade assay format was employed as the primary screen, since a greater signal was achieved with less enzyme. The cRaf1 assay format was used to confirm that cRaf1 was the enzyme affected by the compounds of the present invention.

A. cRaf1 Assay

Human cRaf1 tagged with poly histidine at the carboxy-terminus was expressed in a baculovirus expression system and purfied by Ni chelate affinity chromatography. Human MEK1 was expressed in E. coli as a fusion protein with Glutathione-S-transferase, and purified by glutathione sepharose affinity chromatography. Typically assays were performed in a final volume of 40–100 mL with and without inhibitors. Reactions contained cRaf1 (20 nM), MEK1 (100–500 nM), [γ-$^{32}$P]ATP (10–20 mM), Mg$^{2+}$ (10 mM), MOPS (50 mM, pH 7.5). Reactions were incubated at room temperature for periods of time ranging from 20–120 minutes. Inhibitors were diluted in 100% DMSO prior to addition to the assay. Reactions were terminated with an equal volume of 0.5% phosphoric acid. MEK1 phosphorylation was detected by scintillation counting following collection of protein onto phosphocellulose filters.

B. Raf/MEK Cascade Assay

Human cRaf1 and MEK1 were purified as described above. A peptide substrate phosphorylated by MEK1 was used as the final phosphoryl group acceptor. The sequence of the peptide HTGFLTEYVATRWKK-OH was derived from the site in ERK2 that is phosphorylated by MEK1. Assay conditions were the same as those described above except for the following modifications. Reactions contained cRaf1 (1–5 nM), MEK1 (60 nM), and peptide (250 mM).

C. CDK1 and CDK2

Cyclin dependent protein kinase assays utilized the peptides Biotin-aminohexyl-AAKAKKTPKKAKK and Biotin-aminohexyl-ARRPMSPKKKA-NH$_2$ as phosphoryl group acceptors. CDK1 and CDK2 were both expressed utilizing a baculovirus expression system and were partially purified to comprise 20–80% of total protein, with no detectable competing reactions present. Typically, assays were performed by incubating either enzyme (0.2–10 nM), with and without inhibitor, one of the two peptide substrates (1–10 uM), [γ-$^{32}$P]ATP (1–20 uM), and 10–20 mM Mg$^{2+}$ for periods of time generally within the range 10–120 minutes. Reactions were terminated with 0.2–2 volumes of either 20% acetic acid or 50–100 mM EDTA buffered to pH 7 (substrate consumption<20%). The buffer employed in enzyme assays was either 30 mM HEPES 7.4 containing 0.15M NaCl and 5% DMSO, the buffer 50 mM MOPS 7.0 containing 0.15M NaCl and 5% DMSO, or the buffer 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=$V_{max}$*(1-([I]/(K+[I])))+nsb, or –pIC50s were determined by a fit to the equation CPM=nsb+($V_{max}$–nsb)/(1+(x/10$^x$–pIC50)), where nsb are the background counts.

D. UL97

UL97 was produced as a GST fusion protein from a baculovirus vector expressed in sf9 cells as described by He (He et al., 1997). UL97 was assayed as a protein kinase using $^{32}$p transfer from ATP to histone H2B with detection of radiolabeled histone bound to phosphocellulose. Assay mixes for testing inhibitors of UL97 activity contained 2 mM [γ$^{32}$P]-ATP, 15 mM histone H2B, 50 mM sodiumCHES, pH 9.5, 1 M NaCl, 2 mM dithiothreitol and 10 mM MgCl$_2$. Inhibitors were dissolved in diluted DMSO to give a final DMSO concentration in the reaction of 1% DMSO. After incubation at 20° C., the reactions were terminated by addition of 10 volumes of 75 mM phosphoric acid, 30 mM ATP, 1 mM EDTA, then were spotted onto phosphocellulose filters and washed four times with 75 mM phosphoric acid. Radioactivity was determined by liquid scintillation counting.

E. SRC/lck Enzyme Assay

The peptide substrates used in Src and Lck assays were biotin-aminohexyl EEIYGEF-NH$_2$ (Src) and biotin-aminohexyl-EAIYGVLFAKKK-NH$_2$ (Lck). The src and lck proteins were purified to homogeneity from a baculovirus expression system and preactivated before adding to assay mixtures. The maximum activation was achieved by incubating concentrated enzyme (10–30 uM) on ice for 40 min in the presence of 1 uM ATP and 10 mM MgCl$_2$ in 100 mM HEPES, pH 7.5. The activated enzyme was diluted to 2 nM into an 50 mL reaction mixture containing 100 mM HEPES, pH 7.5, 5 uM ATP, 10 mM MgCl$_2$, 2 uM peptide, 0.05 mg/mL BSA, and an inhibitor at varying concentrations and with or without 8 mCi/mL [γ-$^{33}$P]ATP dependent upon the method of analysis for the extent of reaction. The controls were reactions in the presence (negative controls) or absence (positive controls) of 50 mM EDTA. Reactions were allowed to proceed for 30 min at room temperature and quenched with addition of EDTA to 50 mM in 220 uL. The extent of reactions was analyzed in one of the two ways: an Elisa-based and a radioactive isotope-based. The quenched samples (200 uL) were transferred to a neutravidin coated plate (Perice) and incubated at room temperature for 40 min to allow biotinylated peptide to bind to neutravidin. The unbound peptide and the rest of the solution was washed away using a plate washer. In the Elisa format, a 200 uL HRP-PY20 anti phosphotyrosine antibody conjugate solution was added. After incubation for about 30 min, the plated was washed to remove unbound antibody-HRP conjugate. An Elisa substrate, K-blue (Neogen), was added and the Elisa reaction quenched with Red-stop (Neogen) after 15 min. The plate was read at Ar25 in a plate reader. In the isotope-based format, the reactions had been performed in the presence of [γ-$^{33}$P]ATP. 200 mL Scintiverce DB was added to each well of the plate with bound biotin-peptide. The plate was sealed and counted in a micro-b-counter (Wallac). IC$_{50}$ values were obtained by fitting raw data to A$_{625}$ (cpm)=$V_{max}$*(1-([I]/(IC$_{50}$+[I])))+b, where b is background.

F. VEGFR-2

The peptide substrate used in the VEGFR-2 assay was biotin-aminohexyl-EEEEYFELVAKKKK-NH$_2$. The kinase domain of the enzyme was purified to homogeneity from a baculovirus expression system. The activated enzyme was diluted to 0.4 nM into a 60 μl reaction containing 100 mM HEPES, pH 7.5, 5 μM ATP, 10 mM MgCl$_2$, 5 μM peptide, 0.1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by the addition of EDTA to 60 mM in 210 μl. The quenched samples (190 μl) were transferred to a neutravidin-coated plate (Pierce) and incubated at room temperature for 40 min to allow biotinylated peptide to bind to the neutravidin. The unbound components of the reaction were removed by washing with a plate washer, then 200 μl HRP-PY20 anti-phosphotyrosine antibody conjugate was added to each well. After incubation for 40 minutes, the plate was washed to remove any unbound anitbody.

A HRP substrate, K-blue (Neogen) was added and the reaction was quenched with Red Stop (Neogen) after 20 min. The absorbance of the wells was read at A$_{650}$ in a plate reader.

IC$_{50}$ values were obtained by fitting raw data to A$_{650}$=$V_{MAX}$*(1-[I]/IC$_{50}$+[I])))+b, where b is background.

Representative data are summarized in Table 3. Table 3 illustrates the inhibitory activity of compounds of the present invention against a representative kinase (raf).

TABLE 3

| Example | Raf Kinase activity |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | ++ |
| 26 | + |
| 27 | + |
| 28 | ++ |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | ++ |
| 48 | ++ |
| 49 | ++ |
| 50 | ++ |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |

TABLE 3-continued

| Example | Raf Kinase activity |
|---|---|
| 77 | + |
| 78 | + |
| 79 | + |
| 80 | +++ |
| 81 | + |
| 82 | + |
| 83 | + |
| 84 | + |
| 85 | + |
| 86 | + |
| 87 | +++ |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | ++ |
| 102 | ++ |
| 103 | +++ |
| 104 | + |
| 105 | + |
| 106 | +++ |
| 107 | + |
| 108 | + |
| 109 | + |
| 110 | + |
| 111 | + |
| 112 | ++ |
| 113 | ++ |
| 114 | + |
| 115 | + |
| 116 | + |
| 117 | +++ |
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | ++ |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | +++ |
| 145 | + |
| 146 | +++ |
| 147 | +++ |
| 148 | +++ |
| 149 | +++ |
| 150 | +++ |
| 151 | +++ |
| 152 | + |
| 153 | +++ |
| 154 | +++ |
| 155 | +++ |

TABLE 3-continued

| | |
|---|---|
| 156 | + |
| 157 | + |
| 158 | + |
| 159 | + |
| 160 | + |
| 161 | + |
| 162 | + |
| 163 | + |
| 164 | ++ |
| 165 | + |
| 166 | + |
| 167 | +++ |
| 168 | + |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | + |
| 181 | + |

Key:
| Range | Symbol |
|---|---|
| <0.010–1.00 μM | + |
| 1.00–10.00 μM | ++ |
| 10.00–100 μM | +++ |

Cell Based Efficacy (MTT Assay)

The potency of compounds of the invention are tested for their ability to inhibit cell proliferation and cell viability. The metabolic conversion of 3-(4,5-dimethylthiazol-2-yl)-2,5-diphenyltetrazolium bromide (MTT, Sigma #M2128) to a reduced form is a commonly used measure of cellular viability. Following is the procedure:

Cells are maintained in 75 cm² tissue culture flasks until ready for use. The cells are grown and plated for the assay in Dulbecco's modified Eagle's media containing 10% fetal bovine serum. For example, the following cell lines can be used: a) human foreskin fibroblasts (HFF), b) HT29 (human colon carcinoma cell line), c) MDA-MB-468 (human breast carcinoma cell line), d) RKO (human colon adenocarcinoma cell line), e) SW620 (human colon carcinoma cell line), f) A549 (human lung carcinoma cell line), and g) MIA PACA (human pancreatic carcinoma cell line). Cells are maintained at 37° C. in 10% $CO_2$, 90% humidified air. Cells are plated in 96-well tissue culture plates at the densities listed below. 100 μL of cell suspension is added to each well of the 96-well plate except the top row of the plate which contains no cells and serves as a reference for the spectrophotometer.

| Cell line | Density |
|---|---|
| HFF | 2500 cells/well |
| HT29 cell lines | 2500 cells/well |
| MDA-MB-468 cell line | 5000 cells/well |
| SW620 | 4000 cells/well |
| MIA PACA | 3000 cells/well |
| PC-3 | 4500 cells/well |

Cells are incubated overnight in Dulbecco's modified Eagle's media containing 10% fetal bovine serum at 37° C. in 10% $CO_2$, 90% humidified air prior to dosing. Cells are dosed in 10 sequential 3-fold dilutions starting at 30 uM depending upon the solubility of the compound. Compounds with solubilities of less than 30 uM are dosed at the highest soluble concentration. Stock solutions of compounds are made in 100% dimethyl sulfoxide (DMSO). Stock solutions are diluted in Dulbecco's modified Eagle's media containing 100 ug/mL gentamicin and 0.3 to 0.6% DMSO at the twice the highest concentration to be placed on the cells. If compounds have been dissolved in DMSO the final concentration of DMSO on the cells is kept below 0.3%. 3-fold serial dilutions are performed on each compound to prepare 10 concentrations of the compound for dosing. 100 μL of diluted compound is added to the 100 μL of media currently on the dish. For each concentration of compound, 2–4 replicate wells are prepared.

Cells are returned to incubator and allowed to proliferate in the presence of compound for 72 hours before addition of MTT. MTT is prepared in phosphate buffered saline (Irvine Scientific #9240) at a concentration of 2mg/mL. 50 μL per well of MTT solution is added to the 200 μL of media to yield a final concentration of 0.4 mg/mL and plates are returned to the incubator for 4 hours. After 4 hours incubation the media, compound and MTT mixture is aspirated from the plates and 100 μL of 100% DMSO is added to each well in addition to 25 μL of Sorenson's Buffer (0.1M glycine, 0.1M NaCl, pH 10.5). Quantitation of metabolic reduction of MTT in each plate is performed by reading optical density at 570 nm wavelength on a Molecular Devices UVmax microplate reader. Growth inhibition curves and 50% inhibitory concentrations are determined using Microsoft Excel.

Representative data are summarized in Table 4. Table 4 illustrates the inhibitory activity of compounds of the present invention against a representative kinase (raf) and the cytotoxicity of compounds of the present invention against a broad range of human tumor cell lines.

TABLE 4

| Example | Raf | MTT SW620 (colon) | MTT MIA Paca (pancreatic) | MTT MDA 468 (breast) | MTT PC- (prostate) | MTT HT-29 (colon) |
|---|---|---|---|---|---|---|
| 2 | + | ++ | ++ | ++ | +++ | ++ |
| 133 | + | +++ | +++ | ++ | +++ | ++ |
| 25 | ++ | +++ | +++ | +++ | +++ | +++ |
| 1 | + | +++ | +++ | +++ | +++ | +++ |
| 119 | + | ++ | ++ | ++ | ++ | ++ |
| 130 | + | +++ | +++ | +++ | ++++ | ++++ |
| 8 | + | +++ | +++ | +++ | +++ | +++ |
| 121 | + | ++ | +++ | ++ | ND | ++ |
| 117 | +++ | + | ND | + | ND | ++ |
| 143 | + | ++ | ND | ++ | ND | ++ |

Key
| Symbol | Range |
|---|---|
| + | <0.50 μM |
| ++ | 0.50–5 μM |
| +++ | 5–50 μM |
| ++++ | >50 μM |
| ND | no data |

IN VIVO ASSAYS

Anti-Tumor Studies: Animals

Mice are acquired from Taconic Farms and are maintained in Microisolator cages at 72±2° F. with a 12 hour light/dark cycle. Animals are housed at 4 mice per cage (28×17×12 cm) and are given food and water ad libitum. Animals are numbered through the use of an ear punch or tail tattoo. All animal handling is done in a laminar flow hood.

Cell Growth

SW620, available from the American Type Culture Collection, are grown in media consisting of RPMI 1640 with fetal bovine serum (10%), sodium pyruvate (1.0 mM) and glutamine (2.0 mM). Cells are incubated at 37° C. in 5% $CO_2$. Cells are harvested with trypsin (0.05%), centrifuged, and resuspended in PBS:matrigel (1:1) at $1 \times 10^7$ cell/ml.

Tumor Implantation

One of the tumor cell lines used is the colon line SW620. Tumors are initiated by subcutaneous injection of a cell suspension into the right flank of each mouse. The inoculum consists of $2 \times 10^6$ cells/mouse/ 0.2 ml in PBS:matrigel (1:1).

Tumor Measurement

Solid tumors are measured by caliper measurement through the skin. Caliper measurements are typically made twice weekly. Tumor weight is calculated using the equation (length×width²/2)=mg tumor weight.

Body Weight Measurement

Mice are weighed twice weekly at the time of tumor measurement.

Compound Preparation

Compounds are prepared in a vehicle consisting of DMSO, Cremophore and PBS.

Experimental Therapy

Drug therapy begins when the average tumor size is approximately 40–50 mg, which usually is day 7 after implant. The dose schedule consists of one dose/day for 5 consecutive days. Drugs are administered at 3 or 4 dose-levels based upon the previously-determined maximally tolerated dose. A vehicle control group is also included. Drugs may be administered by either i.v., i.p., s.c., or oral (p.o.) transdermal routes or other alternative routes. Drugs may be administered via tail vein infusion. The injection volume administered for each mouse is usually 0.01–0.02 mL/g of body weight. In the case of i.v. injections and tail vein infusion animals are restrained in a Broome restrainer during handling. Animal are fasted overnight prior to p.o. dosing. The duration of each experiment is typically 28 days from tumor implant.

Representative results are listed in Table 5.

TABLE 5 in vivo data

| Example | Xenograft | Tumor Response % Inhibition @ mg/kg |
|---|---|---|
| 2 | HT-29 | 50% @ 5 mg/kg |
| 85 | SW620 | 40% @ 50 mg/kg |
| 84 | HT-29 | 50% @ 25 mg/kg |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention indicated above. Likewise, the specific pharmacologic responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of formula (I)

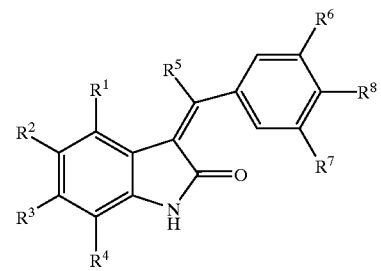

(I)

wherein $R^1$ is H or is optionally joined with $R^2$ to form a fused ring selected from the group consisting of five to ten membered aryl, heteroaryl or heterocyclyl rings, said heteroaryl or said heterocyclyl rings having one to three heteroatoms where zero to three of said heteroatoms are N and zero to 1 of said heteroatoms are O or S and where said fused ring is optionally substituted by one to three of $R^9$, where $R^2$ and $R^9$ are as defined below;

$R^2$ and $R^3$ are independently H, HET, aryl, $C_{1-12}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^{11}$ where said $C_{1-12}$ aliphatic optionally bears one or two insertions of one to two groups selected from C(O), O, S, S(O), $SO_2$ or $NR^{12}$; with said HET, aryl or $C_{1-12}$ aliphatic being optionally substituted by one to three of $R^{10}$; and where $R^2$ is optionally joined with $R^3$ to form a fused ring selected from the group consisting of five to ten membered aryl, heteroaryl or heterocyclyl rings, said heteroaryl or said heterocyclyl rings having zero to three heteroatoms where zero to three of said heteroatoms are N and zero to one of said heteroatoms are O or S and where said fused ring is optionally substituted by one to three of $R^9$; where HET, $R^9$, $R^{10}$, $R^{11}$ and $R^{12}$ are as defined below;

or $R^2$ and $R^3$ are independently $-R^{12}NH_2$, $-R^{12}$-halogen, $-COR^{11}NR^{12}R^{11}$, $-C(NH)R^{11}$, where $R^{11}$ is as defined below, and $R^{12}$ is H, $C_{1-6}$ aliphatic, $NO_2$, $C_{1-6}$ alkoxy, halogen, aryl or HET, said $C_{1-6}$ aliphatic optionally substituted by one to three of halogen or OH, where HET is as defined below;

$R^4$ is H, halogen, $NO_2$ or CN;

$R^5$ is H or $C_{1-12}$ aliphatic optionally substituted by one to three of halo, hydroxyl, or aryl;

$R^6$ and $R^7$ are independently bromo or chloro;

$R^8$ is OH;

each $R^9$ is independently halogen, $C_{1-12}$ aliphatic, CN, $-NO_2$, $R^{10}$, $-OR^{11}$, $-SR^{11}$, $-S(O)R^{10}$, $-SO_2R^{10}$, $-NR^{10}R^{11}$, $-N^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-CO_2R^{11}$, $-CONR^{12}R^{11}$, $-SO_2NR^{12}R^{11}$, $-OCONR^{12}R^{11}$ or $C(NR^{12})NR^{12}R^{11}$, where $R^{10}$, $R^{11}$ and $R^{12}$ are as defined below;

each $R^{10}$ is independently H, halogen, $C_{1-12}$ aliphatic, aryl or HET, where said $C_{1-12}$ aliphatic optionally bears an inserted one to two groups selected from O, S, S(O), $SO_2$ or $NR^{12}$, where said $C_{1-12}$ aliphatic, aryl or HET is optionally substituted by one to three of halo, another HET, aryl, CN, $-SR^{12}$, $-OR^{12}$, $-N(R^2)_2$, $-S(O)R^{12}$, $-SO_2R^{12}$, $SO_2N(R^{12})_2$, $-NR^{12}COR^{12}$, $-NR^{12}CO_2R^{12}$, $-NR^{12}CON(R^{12})_2$, $-NR^{12}(NR^{12})NHR^{12}$, $-CO_2R^{12}$, $-CON(R^{12})_2$, $-NR^{12}SO_2R^{12}$, $-OCON(R^{12})_2$, where HET and $R^{12}$ are as defined below;

or each $R^{10}$ is independently $C_{1-6}$ aliphatic, aryl or HET optionally substituted by one to three of $NO_2$, $R^{12}$, $-R^{12}N(R^{12})_2$ or trifluoro, where $R^{12}$ is H, $C_{1-6}$ aliphatic, $NO_2$, $C_{1-6}$ alkoxy, halogen, aryl or HET, said $C_{1-6}$ aliphatic optionally substituted by one to three of halogen or OH, where HET is as defined below;

or each $R^{10}$ is oxo, cyano or amino;

or each $R^9$ is $-COR^{10}$, where $R^{10}$ is H, $C_{1-6}$ aliphatic or amino;

$R^{11}$ is H or $R^{10}$;

$R^{12}$ is H, $C_{1-12}$ aliphatic or HET, said $C_{1-12}$ aliphatic optionally substituted by one to three of halogen or OH where HET is as defined below; or $R^{12}$ is $NO_2$, $C_{1-6}$ alkoxy, halogen or aryl;

HET is a five to ten-membered saturated or unsaturated heterocyclic ring selected from the group consisting of benzofuran, benzoxazole, dioxin, dioxane, dioxolane, dithiane, dithiazine, dithiazole, dithiolane, furan, imidazole, indole, indazole, morpholine, oxazole, oxadiazole, oxathiazole, oxathiazolidine, oxazine, oxiadiazine, piperazine, piperidine, pyran, pyrazine, pyrazole, pyridine, pyrimidine, pyrrole, pyrrolidine, quinoline, quinazoline, tetrahydrofuran, tetrazine, tetrazole, thiophene, thiadiazine, thiadiazole, thiatriazole, thiazine, thiazole, thiomorpholine, thianaphthalene, thiopyran, triazine, and triazole;

or $R^{12}$ is $(R^{11})_2N-C_{1-6}$ aliphatic, where $R^{11}$ is H, $C_{1-6}$ aliphatic, hydroxy-$C_{1-6}$ aliphatic, phenyl, phenyl-C, aliphatic or HET, where HET is oxazole, pyridine, tetrazole or thiazole; and and the pharmaceutically acceptable salts or solvates thereof.

2. A compound of formula (I) as claimed in claim 1 wherein $R^2$ and $R^3$ are independently H, HET, aryl, $C_{1-12}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^{11}$ where said $C_{1-12}$ aliphatic optionally bears one or two insertions of one to two groups selected from C(O), O, S, S(O), $SO_2$ or $NR^{12}$; with said HET, aryl or $C_{1-12}$ aliphatic being optionally substituted by one to three of $R^{10}$; and where $R^2$ is optionally joined with $R^3$ to form a fused ring selected from the group consisting of five to ten membered aryl, heteroaryl or heterocyclyl rings, said heteroaryl or said heterocyclyl rings having zero to three heteroatoms where zero to three of said heteroatoms are N and zero to one of said heteroatoms are O or S and where said fused ring is optionally substituted by one to three of $R^9$; where HET, $R^9$, $R^{10}$, $R^{11}$ and $R^{12}$ are as defined below;

each $R^{10}$ is independently H, halogen, $C_{1-12}$ aliphatic, aryl or HET, where said $C_{1-12}$ aliphatic optionally bears an inserted one to two groups selected from O, S, S(O), $SO_2$ or $NR^{12}$, where said $C_{1-12}$ aliphatic, aryl or HET is optionally substituted by one to three of halo, another HET, aryl, CN, $-SR^{12}$, $-OR^{12}$, $-N(R^{12})_2$, $-S(O)R^{12}$, $-SO_2R^{12}$, $-SO_2N(R^{12})_2$, $-NR^{12}COR^{12}$, $-NR^{12}CO_2R^{12}$, $-NR^{12}CON(R^{12})_2$, $-NR^{12}(NR^{12})NHR^{12}$, $-CO_2R^{12}$, $-CON(R^{12})_2$, $-NR^{12}SO_2R^{12}$, $-OCON(R^{12})_2$, where HET and $R^{12}$ are as defined below;

$R^{12}$ is H, $C_{1-12}$ aliphatic or HET, said $C_{1-12}$ aliphatic optionally substituted by one to three of halogen or OH where HET is as defined below; and HET, $R^1$, $R^4$, $R^5$, $R^6$, $R^7$, $R^8$ $R^9$ and $R^{11}$ are as defined in claim 1;

and the pharmaceutically acceptable salts or solvates thereof.

3. A compound of formula (I) as claimed in claim 2 wherein $R^1$ is H or is optionally joined with $R^2$ to form a fused ring selected from the group as defined for HET below, and where said fused ring is optionally substituted by one to three of $R^9$, where $R^2$ and $R^9$ are as defined below;

$R^2$ and $R^3$ are independently H, HET, aryl, $C_{1-6}$ aliphatic, CN, $NO_2$, halogen, $R^{10}$, $-OR^{10}$, $-SR^{10}$, $-S(O)R^{10}$, $-SO_2R^{10}$, $-NR^{10}R^{11}$, $-NR^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-COR^{11}$, $-CO_2R^{11}$, $-CONR^{12}R^{11}$, $-SO_2NR^{12}R^{11}$, $-OCONR^{12}R^{11}$, $C(NR^{12})NR^{12}R^{11}$ where said $C_{1-6}$ aliphatic optionally bears one or two insertions of one to two groups selected from C(O), O, S, S(O), $SO_2$ or $NR^{12}$; with said HET, aryl or $C_{1-6}$ aliphatic being optionally substituted by one to three of $R^{10}$; and where $R^2$ is optionally joined with $R^3$ to form a fused ring selected from the group as defined for HET below and where said fused ring is optionally substituted by one to three of $R^9$, where HET, $R^9$, $R^{10}$, $R^{11}$ and $R^{12}$ are as defined below;

$R^5$ is H or $C_{1-6}$ aliphatic optionally substituted by one to three of halo, OH, or aryl;

each $R^9$ is independently halo, $C_{1-6}$ aliphatic, CN, $-NO_2$, $R^{10}$, $-OR^{11}$, $-SR^{11}$, $-S(O)R^{10}$, $-SO_2R^{10}$, $-NR^{10}R^{11}$, $-N^{11}R^{12}$, $-NR^{12}COR^{11}$, $-NR^{12}CO_2R^{11}$, $-NR^{12}CONR^{11}R^{12}$, $-NR^{12}SO_2R^{11}$, $-NR^{12}C(NR^{12})NHR^{11}$, $-CO_2R^{11}$, $-CONR^{12}R^{11}$, $-SO_2NR^{12}R^{11}$, $-OCONR^{12}R^{11}$ or $C(NR^{12})NR^{12}R^{11}$, where $R^{10}$, $R^{11}$ and $R^{12}$ are as defined below;

each $R^{10}$ is independently H, halogen, $C_{1-6}$ aliphatic, aryl or HET, where said $C_{1-6}$ aliphatic optionally bears an inserted one to two groups selected from O, S, S(O), $SO_2$ or $NR^{12}$, where said $C_{1-6}$ aliphatic, aryl or HET is optionally substituted by one to three of halo, another HET, aryl, CN, —$SR^{12}$, —$OR^{12}$, —$N(R^{12})_2$, —$S(O)R^{12}$, —$SO_2R^{12}$, —$SO_2N(R^{12})_2$, —$NR^{12}COR^{12}$, —$NR^{12}CO_2R^{12}$, —$NR^{12}CON(R^{12})_2$, —$NR^{12}(NR^{12})NHR^{12}$, —$CO_2R^{12}$, —$CON(R^{12})_2$, —$NR^{12}SO_2R^{12}$, —$OCON(R^{12})_2$, where HET and $R^{12}$ are as defined below;

$R^{12}$ is H, $C_{1-6}$ aliphatic or HET, said $C_{1-6}$ aliphatic optionally substituted by one to three of halogen or OH where HET is as defined below; and HET, $R^4$, $R^6$, $R^7$, $R^8$ and $R^{11}$ are as defined in claim 1;
and the pharmaceutically acceptable salts or solvates thereof.

4. A compound of formula (I) as claimed in claim 1 wherein $R^1$ is H or is optionally joined with $R^2$ to form a fused ring selected from the group consisting of fused pyridine, fused triazole, fused thiazole or fused amino-substituted thiazole; or $R^1$ and $R^2$ comprise a fused ring which is methyl substituted fused pyridine.

HET is a five or six-membered saturated or unsaturated heteroaryl ring selected from the group consisting of dioxin, dioxane dioxolane, dithiane, dithiazine, dithiazole, dithiolane, furan, imidazole, imidazopyridinyl, morpholine, oxazole, oxadiazoie, oxathiazole, oxathiazolidine, oxazine, oxiadiazine, piperazine, piperidine, pyran, pyrazine, pyrazole, pyridine, pyrimidine, pyrrole, pyrrolidine, tetrahydrofuran, tetrazine, thiophene, thiadiazine, thiadiazole, thiatriazole, thiazine, thiazole, thiomorpholine, thiopyran, thioxotriazine, triazine, and triazole;

$R^2$, $R^3$, $R^{10}$ and $R^{12}$ are as defined in claim 1;
$R^4$, $R^6$, $R^7$, $R^8$ and $R^{11}$ are as defined in claim 1; and
$R^5$ and $R^9$ are as defined in claim 3;
and the pharmaceutically acceptable salts or solvates thereof.

5. A compound of formula (I) as claimed in claim 1 wherein $R^1$ is H or is optionally joined with $R^2$ to form a fused ring selected from the group consisting of five to six membered heteroaryl rings, said heteroaryl ring having one to two heteroatoms where zero to two of said heteroatoms are N and zero to two of said heteroatoms are O or S and where said fused ring is optionally substituted by one to three of $R^9$, where $R^2$ and $R^9$ are as defined below;

$R^2$ and $R^3$ are independently H, HET, phenyl, $C_{1-6}$ aliphatic, —$NR^{10}R^{11}$, —$COR^{11}$, —$CO_2R^{11}$, —$CONR^{12}R^{11}$, —$SO_2NR^{12}R^{11}$, with said HET, phenyl or $C_{1-6}$ aliphatic being optionally substituted by $R^{10}$; and where $R^2$ is optionally joined with $R^3$ to form a fused five membered heterocyclyl ring, said heterocyclyl ring having zero to 1 heteroatoms where said heteroatom is N and zero to 1 heteroatoms where said heteroatoms are O or S and where said fused ring is optionally substituted by $R^9$, where HET, $R^9$, $R^{10}$, $R^{11}$ and $R^{12}$ are as defined below;

$R^4$ is H;
$R^5$ is H;
$R^6$, $R^7$ and $R^8$ are as defined in claim 1;
$R^9$ is $C_{1-6}$ aliphatic or —$COR^{10}$, where $R^{10}$ is as defined below;
$R^{10}$ is H, $C_{1-6}$ aliphatic or amino;
$R^{11}$ is H, $C_{1-6}$ aliphatic, hydroxy-$C_{1-6}$ aliphatic, phenyl, phenyl-$C_{1-6}$ aliphatic or HET;

$R^{12}$ is H, $C_{1-6}$ aliphatic, hydroxy-$C_{1-6}$ aliphatic or $(R^{11})_2$N—$C_{1-6}$ aliphatic; and HET is a heterocyclic ring selected from the group consisting of oxazole, pyridine, tetrazole and thiazole;
and the pharmaceutically acceptable salts or solvates thereof.

6. A compound of formula (I) as claimed in claim 1 wherein $R^1$ is H;

$R^2$ and $R^3$ are independently H, HET, phenyl, $C_{1-6}$ aliphatic, cyano, halogen, —$COR^{11}$, or —$CONR^{12}R^{11}$, with said HET, phenyl or $C_{1-6}$ aliphatic being optionally substituted by $R^{10}$, where HET, $R^{10}$, $R^{11}$ and $R^{12}$ are as defined below;

$R^4$ is H;
$R^5$ is H;
$R^6$, $R^7$ and $R^8$ are as defined in claim 1;
$R^{10}$ is H, $C_{1-6}$ aliphatic, oxo or cyano;
$R^{11}$ is H, $C_{1-6}$ aliphatic, trihalo-$C_{1-6}$ aliphatic, phenyl or nitro-substituted phenyl;
$R^{12}$ is H, $C_{1-6}$ aliphatic, hydroxy-$C_{1-6}$ aliphatic; and
HET is thiophene or pyridine;
and the pharmaceutically acceptable salts or solvates thereof.

7. A compound as claimed in claim 1, selected from the group consisting of

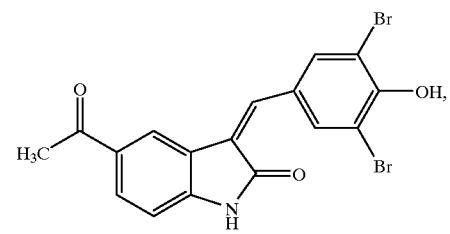

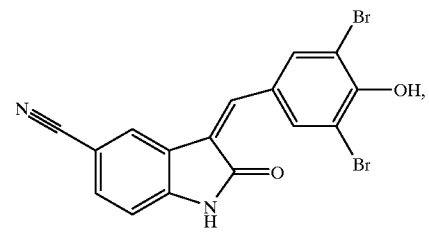

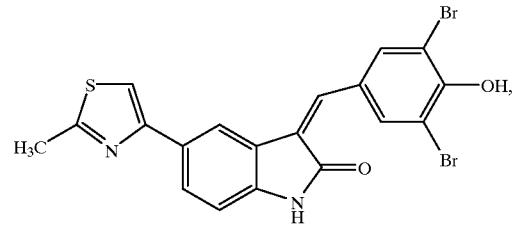

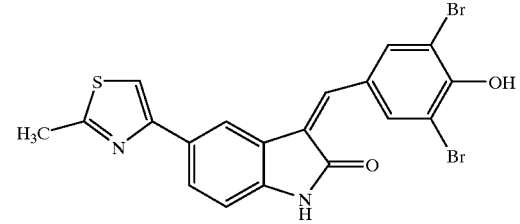

HCl,

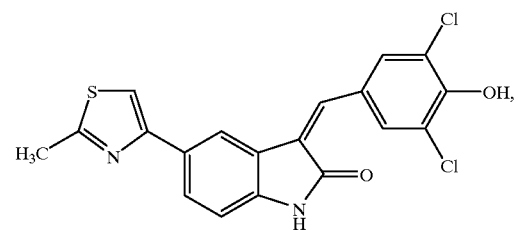
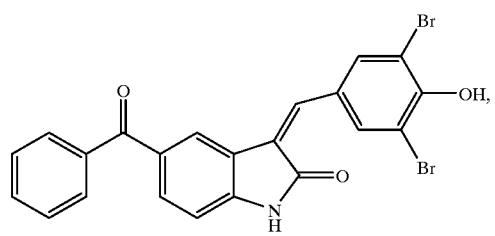
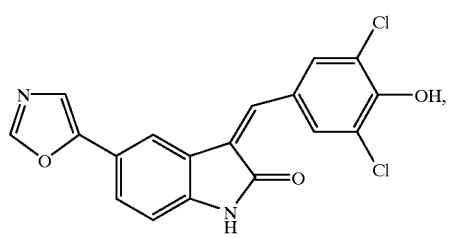
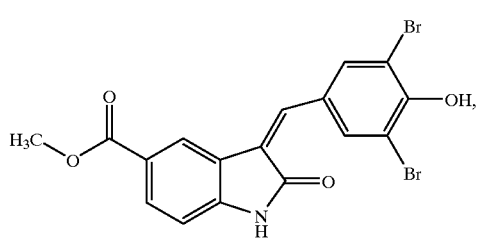
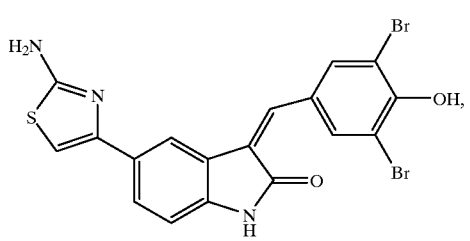
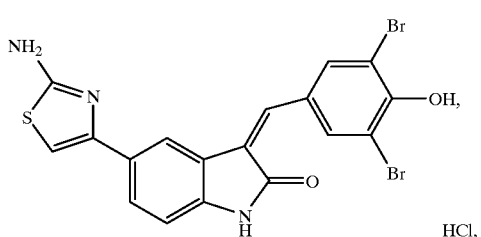
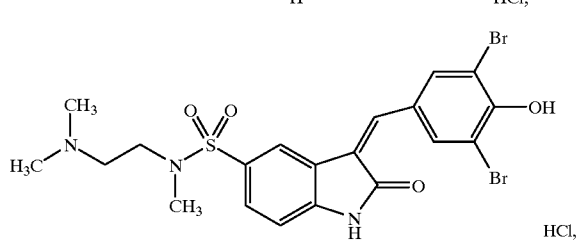
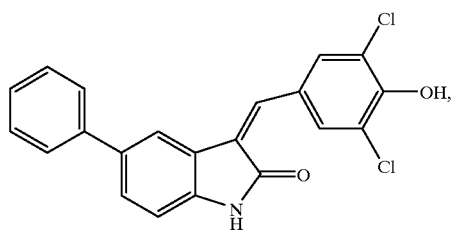
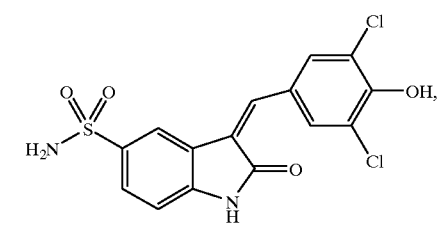
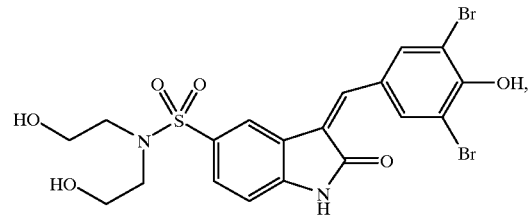
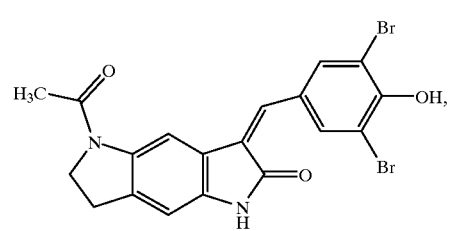
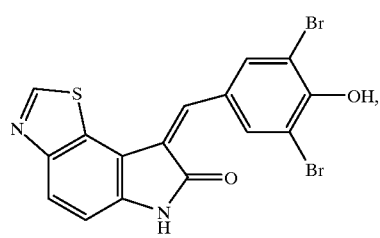
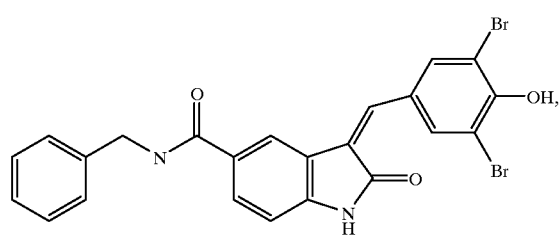
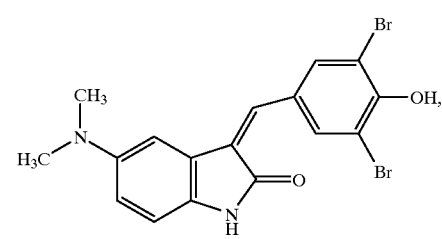

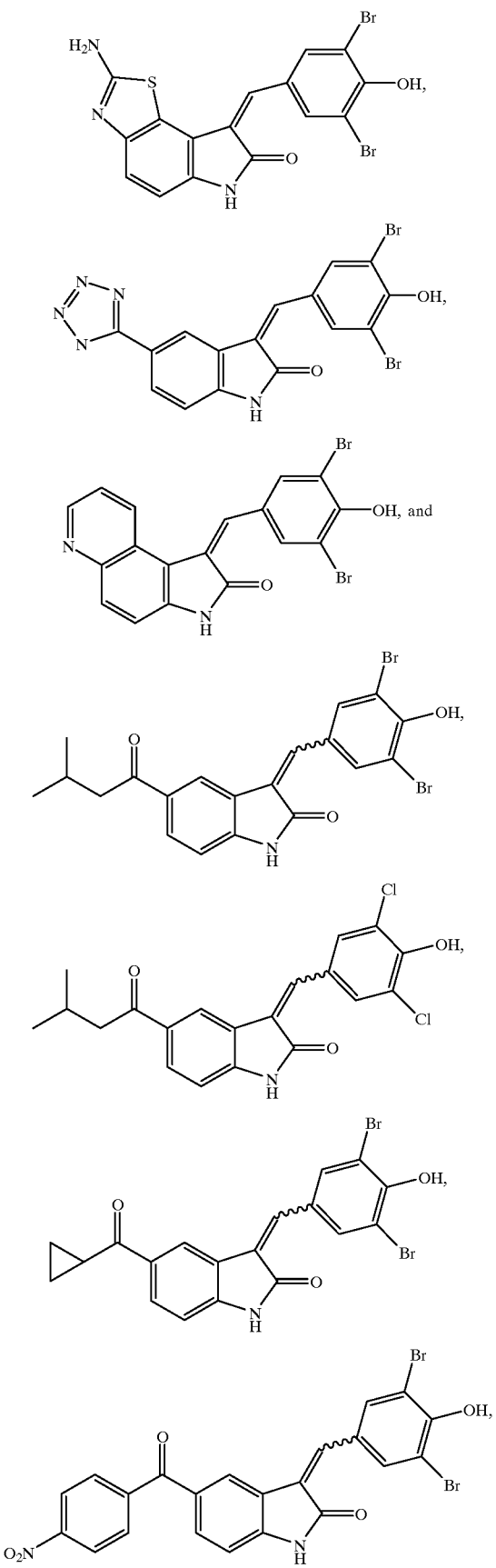
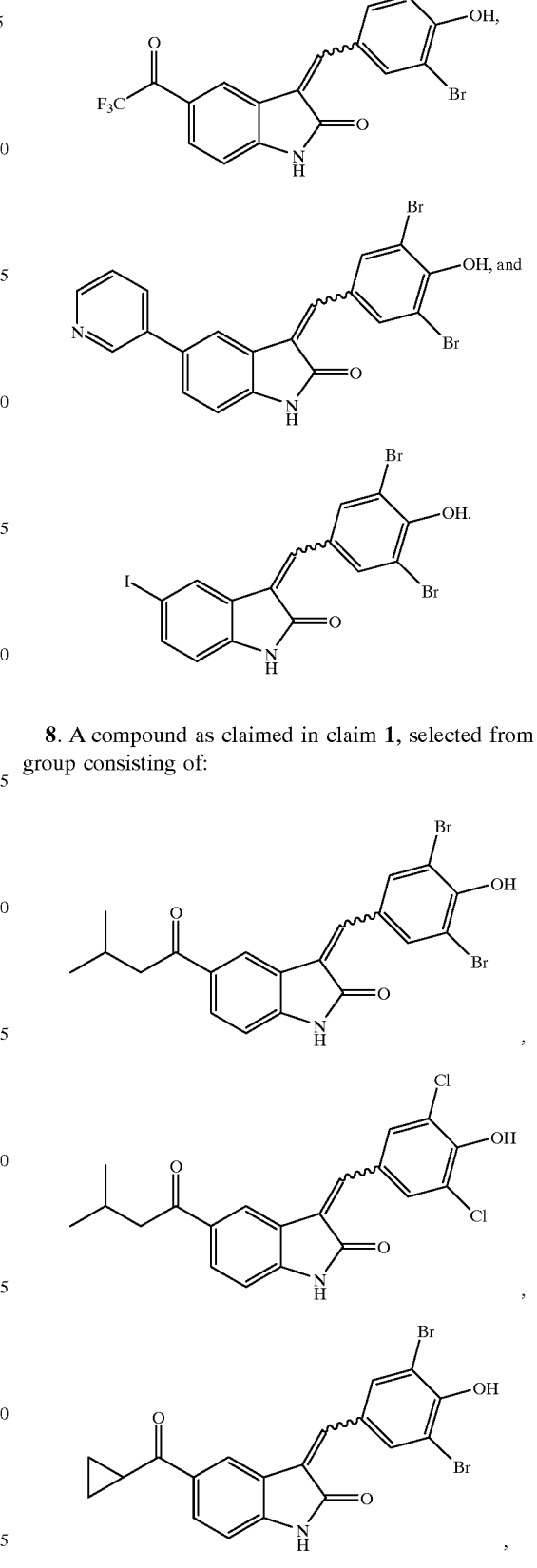
8. A compound as claimed in claim 1, selected from the group consisting of:

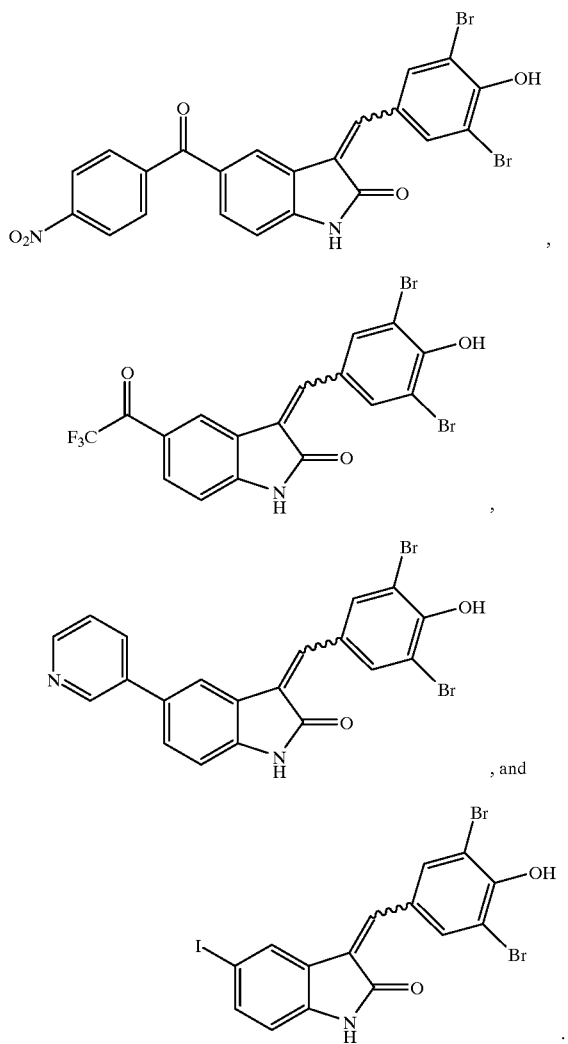

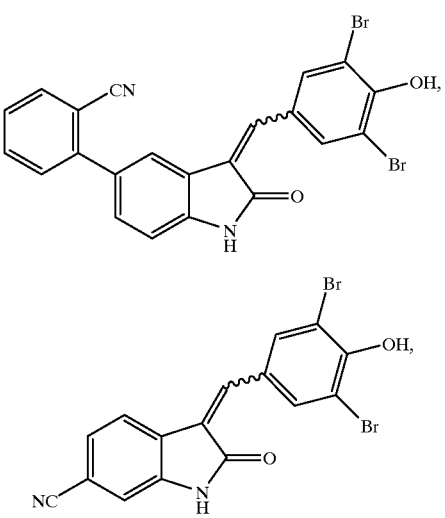

9. A compound as claimed in claim 1, selected from the group consisting of:

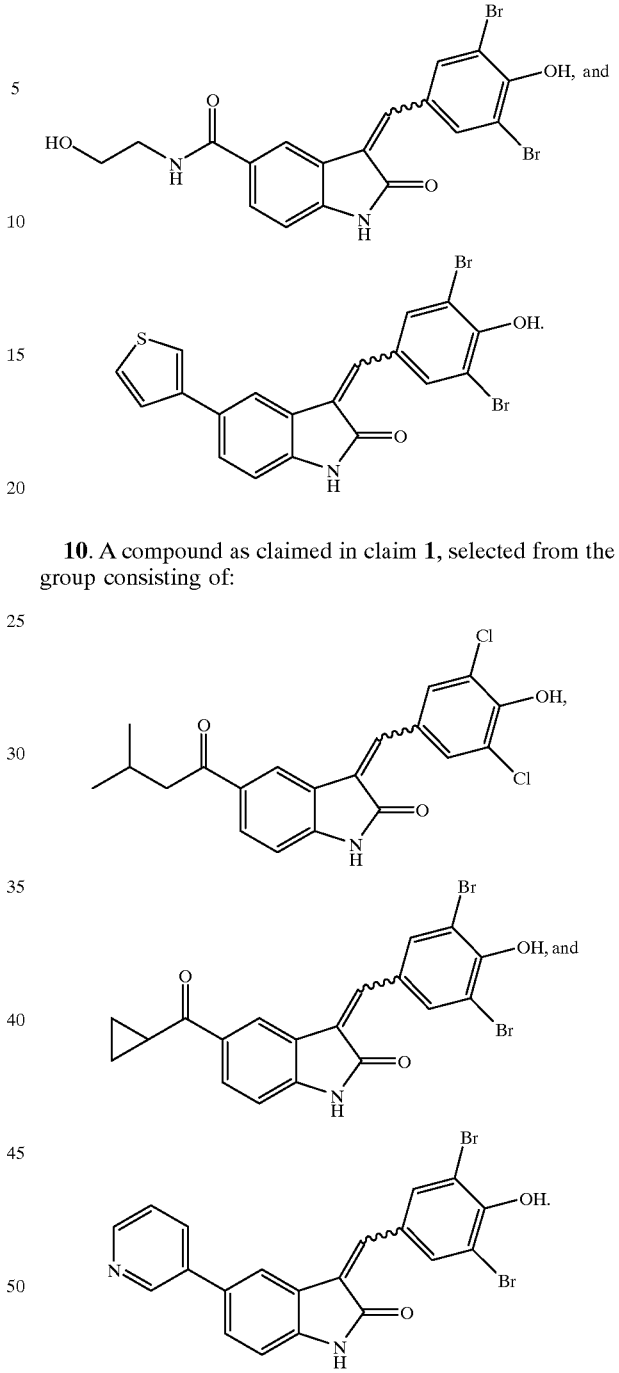

10. A compound as claimed in claim 1, selected from the group consisting of:

11. The compound 3-(3,5-Dibromo-4-hydroxy-benzylidene)-5-pyrid-3-yl-1,3-dihydro-indol-2-one; and pharmaceutically acceptable salts and solates thereof.

12. A compound as claimed in claim 1, wherein said compound is in the E geometric isomer form.

13. A compound as claimed in claim 1, wherein said compound is in the Z geometric isomer form.

14. A compound as claimed in claim 1, wherein said compound is a mixture of the Z geometric isomer form and the E geometric isomer form.

15. A compound as claimed in claim 1, having a chiral carbon atom and which compound is dextrorotatory.

16. A compound as claimed in claim 1, having a chiral carbon atom and which compound is levorotatory.

17. A compound as claimed in claim 1, having a chiral carbon atom and which is a mixture of dextrorotatory and levorotatory.

18. A prodrug of a compound as claimed in claim 1 which is a biohydrolyzable ester, biohydrolyzable amide, biohydrolyzable carbamate, biohydrolyzable carbonate or biohydrolyzable ureide, said biohydrolyzable functionality being linked to the OH group representing $R^8$ in the compound of formula (I).

19. A prodrug as claimed in claim 18 wherein said OH group is conjugated with a carbamoyl conjugate to yield a biohydrolyzable carbamate wherein said carbamoyl conjugate is selected from the group consisting of diethylaminocarbonyl, N-(2-hydroxyethyl)aminocarbonyl, N,N,-bis(2-hydroxyethyl)aminocarbonyl, hydroxyethyloxyethylaminocarbonyl, 4-morpholinocarbonyl and 4-methyl-i-piperazinylcarbonyl.

20. A prodrug as claimed in claim 19 selected from

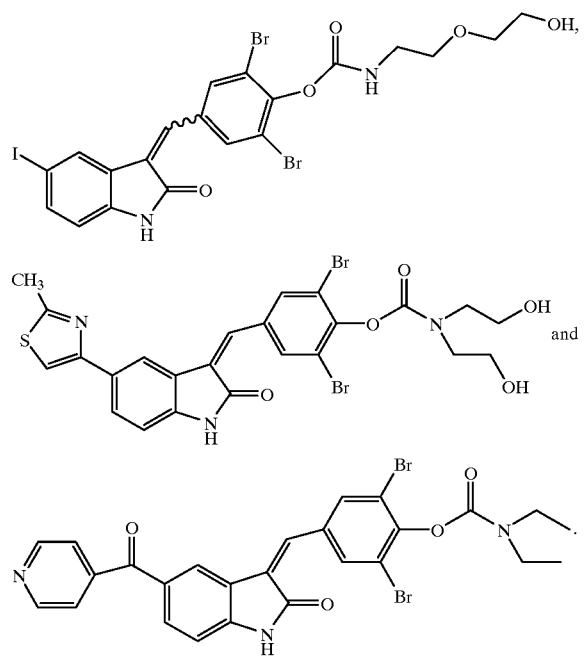

21. A prodrug as claimed in claim 18 wherein said OH group is conjugated with a carbonate conjugate to yield a biohydrolyzable carbonate wherein said carbonyl conjugate is selected from the group consisting of phenylmethyloxycarbonyl, ethyloxycarbonyl, isobutyloxycarbonyl, and pyridinemethyloxycarbonyl.

22. A prodrug as claimed in claim 18 wherein said OH group is conjugated with an ester conjugate to yield a biohydrolyzable ester wherein said ester conjugate is t-butylcarbonyloxymethyl.

23. A pharmaceutical composition comprising a pharmaceutically acceptable carrier and a pharmacologically effective amount of a compound as claimed in claim 1.

24. A process for the preparation of a compound of formula (I) as claimed in claim 1, which process comprises the reaction of a compound of formula (II)

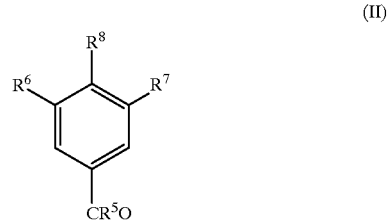

wherein $R^5$, $R^6$, $R^7$ and $R^8$ are as defined in claim 1, with a compound of formula (III)

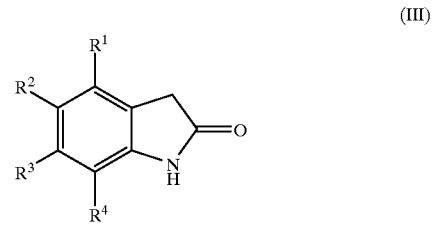

wherein $R^1$, $R^2$, $R^3$ and $R^4$ are as defined in claim 1.

25. A method of treating a disease mediated by cRaf1 kinase, said method comprising the step of administering to a mammal in need thereof a pharmacologically effective amount of a compound as claimed in claim 1.

26. A method of inhibiting tumor growth, comprising the step of administering to a patient in need thereof a pharmacologically effective amount of a compound as claimed in claim 1.

* * * * *